(12) United States Patent
Stanley et al.

(10) Patent No.: US 8,470,323 B2
(45) Date of Patent: Jun. 25, 2013

(54) DRUG DELIVERY TO HUMAN TISSUES BY SINGLE CHAIN VARIABLE REGION ANTIBODY FRAGMENTS CLONED BY PHAGE DISPLAY

(75) Inventors: John R. Stanley, Gladwyne, PA (US); Donald L. Siegel, Lansdale, PA (US); Amagai Masayuki, Tokyo (JP)

(73) Assignees: The Trustees of the University of Pennsylvania, Philadelphia, PA (US); Keio University, Tokyo (JP)

( * ) Notice: Subject to any disclaimer, the term of this patent is extended or adjusted under 35 U.S.C. 154(b) by 102 days.

(21) Appl. No.: 12/522,526

(22) PCT Filed: Jan. 9, 2008

(86) PCT No.: PCT/US2008/000288
§ 371 (c)(1),
(2), (4) Date: Mar. 28, 2011

(87) PCT Pub. No.: WO2008/085987
PCT Pub. Date: Jul. 17, 2008

(65) Prior Publication Data
US 2011/0200601 A1      Aug. 18, 2011

Related U.S. Application Data

(60) Provisional application No. 60/879,700, filed on Jan. 9, 2007, provisional application No. 60/903,394, filed on Feb. 26, 2007.

(51) Int. Cl.
*A61K 39/395*      (2006.01)

(52) U.S. Cl.
USPC .................................................. 424/134.1

(58) Field of Classification Search
None
See application file for complete search history.

(56) References Cited

U.S. PATENT DOCUMENTS

| | | | |
|---|---|---|---|
| 7,235,641 B2 | 6/2007 | Kufer et al. | |
| 2006/0223142 A1 | 10/2006 | Dumas et al. | |
| 2007/0014788 A1* | 1/2007 | Mathiasen et al. | 424/133.1 |
| 2007/0065447 A1* | 3/2007 | Tryggvason et al. | 424/155.1 |
| 2009/0269850 A1* | 10/2009 | Kaneda et al. | 435/456 |
| 2010/0092457 A1* | 4/2010 | Aburatani et al. | 424/130.1 |

OTHER PUBLICATIONS

Muratani et al., Cell, 2005, 120: 887-889.*
Ishii et al., 2005, J Invest Dermatol 124:939-46.
Li et al., 2003, J Exp. Med., 197:1501-1510.
Payne et al., 2004, Curr. Opin. Cell Biol. 16:536-543.
Sekiguchi et al 2001, J Immunol 167:5439-5448.
Siegel et al., 1997, J Immunol Methods 206:73-85.
Tsunoda et al., 2003, J. Immunol 170:2170-2178.

* cited by examiner

*Primary Examiner* — Ilia Ouspenski
(74) *Attorney, Agent, or Firm* — Riverside Law LLP

(57) ABSTRACT

The present invention relates to the use of non-pathogenic antibodies to deliver biologically-active proteins to specific cellular and sub-cellular sites. The invention also relates to the use of non-pathogenic antibodies to deliver biologically-active, non-protein molecules to specific cellular and sub-cellular sites.

18 Claims, 31 Drawing Sheets

| scFv Name(s) | Desmoglein Specificity | Heavy Chain Identifier | Light Chain Identifier |
|---|---|---|---|
|  |  |  |  |
| D(3)4-6, D(3)3-7, D(3)1b/3a, PV4B6 | Dsg-3 | 1b | 3a |
| D(3)4-7, D(3)3-4, D(3)2-7, D(3)1d/2c | Dsg-3 | 1d | 2c |
| D(3)3-9, D(3)1h/2b | Dsg-3 | 1g | 2e |
| D(3)2-4, D(3)1i/4d | Dsg-3 | 1i | 4d |
|  |  |  |  |
| D(31)4-2, D(31)3-1, D(31)3-7, D(31)12a/5, PX4-2 | Dsg-1 and Dsg-3 | 12a | 5 |
| D(31)4-4, D(31)4-5, D(31)4-7, D(31)3-4, D(31)3-6, D(31)12b/6, PX4-4 | Dsg-1 and Dsg-3 | 12b | 6 |

Figure 17A

| Chain Identifier | Nucleotide Sequence | Amino Acid Sequence |
|---|---|---|
|  |  |  |
| Heavy Chains |  |  |
| 1b | SEQ ID NO1 | SEQ ID NO 13 |
| 1d | SEQ ID NO 2 | SEQ ID NO 14 |
| 1g | SEQ ID NO 3 | SEQ ID NO 15 |
| 1i | SEQ ID NO 4 | SEQ ID NO 16 |
| 12a | SEQ ID NO 5 | SEQ ID NO 17 |
| 12b | SEQ ID NO 6 | SEQ ID NO 18 |
|  |  |  |
| Light Chains |  |  |
| 2c | SEQ ID NO 7 | SEQ ID NO 19 |
| 2e | SEQ ID NO 8 | SEQ ID NO 20 |
| 3a | SEQ ID NO 9 | SEQ ID NO 21 |
| 4d | SEQ ID NO 10 | SEQ ID NO 22 |
| 5 | SEQ ID NO 11 | SEQ ID NO 23 |
| 6 | SEQ ID NO 12 | SEQ ID NO 24 |

Figure 17B

SEQ ID NO 1:
CAGGTGCAGCTGGTGCAGTCTGGGGCTGAGATGAAGAAGCCTGGGTCC
TCGGTGAGGGTCTCCTGCAAGGCTTCTGGAGGCACCTTCGACAAATATG
CTGTCAGTTGGGTGCGACAGGCCCCAGGACGAGGGCTTGAGTGGGTGG
GAGGGATCATCCCTATGCTTGGTGCTCCACACTACGCACAGAAGTTCCA
GGGCAGAGTCACGATCACCGCGGACAAATCCACGAGCACAGTCTACATG
GAACTGAGCAGCCTGGGATCTGAGGACACAGCCGTGTATTACTGTGCGA
GAGATAAAGCGGCTTACTATGAAAGTGGTTATTACTATATCGGTGACTTC
TGGGGCCAGGGGACCCTGGTCACCGTCTCCTCAGCCTCCACCAAGGGC
CCATCGGTCACTAGTGGCCAGGC

Figure 17C-1

SEQ ID NO 2:
CAGGTGCAGCTGGTGCAGTCTGGGGCTGAGATGAAGAAGCCTGGGTCC
TCGGTGAGGGTCTCCTGCAAGGCTTCTGGAGGCACCTTCGACAAATATG
CTGTCAGCTGGGTGCGACAGGCCCCAGGACGAGGGCTTGAGTGGGTGG
GAGGGATCATCCCTATGCTTGGTGCTCCACACTACGCACAGAAGTTCCA
GGGCAGAGTCACGATCACCGCGGACAAATCCACGAGCACAATCTACATG
GAACTGAGCAGCCTGGGATCTGAGGACACAGCCGTGTATTACTGTGCGA
GAGATAAAGCGGCTTACTATGAAAGTGGTTATTACTATATCGGTGACTTC
TGGGGCCAGGGAACCCTGGTCACCGTCTCCTCAGCTTCCACCAAGGGC
CCATCGGTCACTAGTGGCCAGGC

Figure 17C-2

SEQ ID NO 3:
GAGGTGCAGCTGGTGGAGTCTGGGGCTGAGATGAAGAAGCCTGGGTCC
TCGGTGAGGGTCTCCTGCAAGGCTTCTGGAGGCACCTTCGACAAATATG
GTGTCAGTTGGGTGCGACAGGCCCCAGGACGAGGGCTTGAGTGGGTGG
GAGGGATCATCCCTATGCTTGGTGCTCCACACTACGCACAGAAGTTCCA
GGGCAGAGTCACGATCACCGCGGACAAATCCACGAGCACAGTCTATATG
GAACTGAGCAGCCTGGGATCTGAGGACACAGCCGTGTATTACTGCGCGA
GAGATAAAGCGGCTTACTATGAAAGTGGTTATTACTATATCGGTGACTTC
TGGGGCCAGGGAACCCTGGTCACCGTCTCCTCAGCCTCCACCAAGGGC
CCATCGGTCACTAGTGGCCAGGC

Figure 17C-3

SEQ ID NO 4:
CAGGTGCAGCTGGTGCAGTCTGGGGCTGAGATGAAGAGGCCTGGGTCC
TCGGTGAGGGTCTCCTGCAAGGCTTCTGGAGGCACCTTCGACAAATATG
CTGTCAGTTGGGTGCGACAGGCCCCAGGACGAGGGCTTGAGTGGGTGG
GGGGGATCATCCCTCTGCTTGGTGCTCCACACTACGCACAGAAGTTCCA
GGGCAGAGTCACGATCACCGCGGACAAATCCACGAGCACAGTCTACATG
GAACTGAGCAGCCTGGGATCTGAGGACACAGCCGTGTATTACTGCGCGA
GAGATAAAGCGGCTTACTATGAAAGTGGTTATTACTATATCGGTGACTTC
TGGGGCCAGGGAACCCTGGTCACCGTCTCCTCAGCCTCCACCAAGGGC
CCATCGGTCACTAGTGGCCAGGC

Figure 17C-4

SEQ ID NO 5:
GAGGTGCAGCTGTTGGAGTCTGGCCCAGGACCGGTGAAGCCTTCGGGG
ACCCTGTCCCTCACCTGTGGTGTCTCTGGTGGCTCCATCAGCACTAATC
ACTGGTGGACTTGGGTCCGCCAGCCCCAGGGCAGGGGCTGGAGTGG
ATTGGGGAAATCCATCATAATGGGAGCACCTTCTTCAACCCGTCCCTCAA
GAGTCGAGTCACCATTTCAGTGGACAAGTCCAACAACCAGTTCTCCCTG
AAACTGACCTCTCTGACCGCCGCGGACACGGCCGTGTATTTCTGTGCGA
GAGGGTGGCACCGGACTGGATTTCGTGGCTACCCTTCCCACTGGTACTT
CGATCTCTGGGGCCGTGGCACCCTGGTCACTGTCTCCTCAGCTTCCACC
AAGGGCCCATCGGTCACTAGTGGCCAGGC

Figure 17C-5

SEQ ID NO 6:
CAGGTGCAGCTGCAGGAGTCGGGCCCAGGACCGGTGAAGCCTTCGGG
GACCCTGTCCCTCACCTGCGGTGTCTCTGGTGGCTCCATTAGCAGTAAT
CACTGGTGGACTTGGGTCCGCCAGCCCCAGGGAAGGGGCTGGAGTG
GATTGGAGAAATCTATCATAATGGGAGCACCTTCCTCAACCCGTCCCTCA
AGAGTCGAGTCACCATTTCAGTAGACAAGTCCAACAACCAGTTCTCCCTG
AAACTGACTTCTGTGACCGCCGCGGACACGGCCGTGTATTACTGTGCGA
GAGGGTGGCACCGGACTGGATTTCGTGGCTACCCTTCCCACTGGTACTT
CGATCTCTGGGGCCGTGGCACCCTGGTCTCTGTCTCCTCAGCCTCCACC
AAGGGCCCATCGGTCACTAGTGGCCAGGC

Figure 17C-6

SEQ ID NO 7:
GCCGAGCTCGTGCTGACTCAGCCACCTTCAGCGTCTGAGACCCCGGG
CAGAGGGTCACCATCTCCTGTTCTGGAAGCAGCTCCAACATCGCAGGTA
ATACTGTGTACTGGTACCAGCAGCTCCCAGGAGCGGCCCCAAGCTCCT
CATCTATTACAATGATCAGCGGCCCTCAGGGGTCCCTGACCGATTCTCT
GGCTCCAAGTCTGGCACCTCCTCCTCCTTGGCCATCAGTGGGCTCCAGT
CTGAGGATGAGGCTTATTATTACTGTGCAACATGGGATGAAGATGTGAAT
GGTTGGGTGTTCGGCGGAGGGACCAAGCTGACCGTCCTAG

Figure 17C-7

SEQ ID NO 8:
GCCGAGCTCGAGCTGACTCAGCCACCCTCAGTGTCTGGGACCCCGGG
CAGAGGGTCACCATCTCCTGTTCTGGAAGCAGCTCCAACATCGCAGGTA
ATACTGTGTACTGGTACCAACAGCTCCCAGGAGCGGCCCCAAGCTCCT
CATCTATTACAATGATCAGCGGCCCTCAGGGGTCCCTGACCGATTCTCT
GGCTCCAAGTCTGGCACCTCCTCCTCCTTGACCATCAGTGGGCTCCAGT
CTGAGGATGAGGCTTATTATTACTGTGCAACATGGGATGAAGATGTGAAT
GGTTGGGTGTTCGGCGGAGGCACCAAGCTGACCGTCCTAG

Figure 17C-8

SEQ ID NO 9:
GCCGAGCTCATGCTGACTCAGCCCCACTCAGCGTCTGAGACCCCGGG
CAGAGGGTCACCATCTCCTGTTCTGGAAGCAGCTCCAACATCGCAGGTA
ATACTGTGTACTGGTACCAGCAGCTCCCAGGAGCGGCCCCAAGCTCCT
CATCTATTACAATGATCAGCGGCCCTCAGGGGTCCCTGACCGATTCTCT
GGCTCCAAGTCTGGCACCTCCTCCTCCTTGGCCATCAGTGGGCTCCAGT
CTGAGGATGAGGCTTATTATTACTGTGCAACATGGGATGAAGATGTGAAT
GGTTGGGTGTTCGGCGGAGGGACCGAGCTGACCGTCCTCG

Figure 17C-9

SEQ ID NO 10:
GCCGAGCTCGTGCTGACTCAATCGCCCTCAGCGTCTGAGACCCCGGG
CAGAGGGTCACCATCTCCTGTTCTGGAAGCAGCTCCAACATCGCAGGTA
ATACTGTATACTGGTACCAGCAGCTCCCAGGAGCGGCCCCAAGCTCCT
CATCTATTACAATGATCAGCGGCCCTCAGGGGTCCCTGACCGATTCTCT
GGCTCCAAGTCTGGCACCTCCTCCTCCTTGGCCATCAGTGGGCTCCAGT
CTGAGGATGAGGCTTATTATTACTGTGCGACATGGGATGAAGATGTGAAT
GGTTGGGTGTTCGGCGGAGGGACCAAGGTGACCGTCCTAG

Figure 17C-10

SEQ ID NO 11:
GCCGAGCTCGTGTTGACGCAGCCGCCCTCAGTGTCTGGGACCCCCGGG
CAGAGGGTCACCATCTCTTGTTCTGGAAGCAGCTCCCACATCGGAAATA
ATTATGTATACTGGTACCAGCATCTCCCAGGAACGGCCCCCAAACTCCTC
ATCTACAGTAATGATCAGCGGCCCTCAGGGGTCCCTGACCGATTCTCTG
CCTCCAAGTCTGCCACCTCAGCCTCCCTGGCCATCAGTGGGCTCCGGTC
CGAGGATGAGGCTGATTATTACTGTGCAGCATGGGATGACAGCCAGGG
GGGAGTGTTCGGCGGAGGGACCAAGGTGACCGTCCTAG

Figure 17C-11

SEQ ID NO 12:
GCCGAGCTCGTGCTGACTCAGCCACCTTCAGTGTCTGGGACCCCCGGG
CAGAGGGTCACCATCTCTTGTTCTGGAAGCAGCTCCCACATCGGAAGTA
ATTATGTGTACTGGTACCAGCAGCTCCCAGGAACGGCCCCCAAAATCCT
CATCTACAGTAATGATCAGCGGCCCGCAGGGGTCCCTGACCGATTCTCT
GCCTCCAAGTCTGGCACCTCAGCCTCCCTGGCCATCAGTGGGCTCCGG
TCCGAGGATGAGGCTGATTATTACTGTGCAGCATGGGATGACGGCCAGG
GGGGGGTCTTCGGCGGAGGGACCAAGCTGACCGTCCTAG

Figure 17C-12

SEQ ID NO 13:
QVQLVQSGAEMKKPGSSVRVSCKASGGTFDKYAVSWVRQAPGRGLEWVG
GIIPMLGAPHYAQKFQGRVTITADKSTSTVYMELSSLGSEDTAVYYCARDKA
AYYESGYYYIGDFWGQGTLVTVSSASTKGPSVTSGQ

Figure 17C-13

SEQ ID NO 14:
QVQLVQSGAEMKKPGSSVRVSCKASGGTFDKYAVSWVRQAPGRGLEWVG
GIIPMLGAPHYAQKFQGRVTITADKSTSTIYMELSSLGSEDTAVYYCARDKAA
YYESGYYYIGDFWGQGTLVTVSSASTKGPSVTSGQ

Figure 17C-14

SEQ ID NO 15:
EVQLVESGAEMKKPGSSVRVSCKASGGTFDKYGVSWVRQAPGRGLEWVG
GIIPMLGAPHYAQKFQGRVTITADKSTSTVYMELSSLGSEDTAVYYCARDKA
AYYESGYYYIGDFWGQGTLVTVSSASTKGPSVTSGQ

Figure 17C-15

SEQ ID NO 16:
QVQLVQSGAEMKRPGSSVRVSCKASGGTFDKYAVSWVRQAPGRGLEWVG
GIIPLLGAPHYAQKFQGRVTITADKSTSTVYMELSSLGSEDTAVYYCARDKAA
YYESGYYYIGDFWGQGTLVTVSSASTKGPSVTSGQ

Figure 17C-16

SEQ ID NO 17:
EVQLLESGPGPVKPSGTLSLTCGVSGGSISTNHWWTWVRQPPGQGLEWIG
EIHHNGSTFFNPSLKSRVTISVDKSNNQFSLKLTSLTAADTAVYFCARGWHR
TGFRGYPSHWYFDLWGRGTLVTVSSASTKGPSVTSGQ

Figure 17C-17

SEQ ID NO 18:
QVQLQESGPGPVKPSGTLSLTCGVSGGSISSNHWWTWVRQPPGKGLEWI
GEIYHNGSTFLNPSLKSRVTISVDKSNNQFSLKLTSVTAADTAVYYCARGWH
RTGFRGYPSHWYFDLWGRGTLVSVSSASTKGPSVTSGQ

Figure 17C-18

SEQ ID NO 19:
AELVLTQPPSASETPGQRVTISCSGSSSNIAGNTVYWYQQLPGAAPKLLIYY
NDQRPSGVPDRFSGSKSGTSSSLAISGLQSEDEAYYYCATWDEDVNGWVF
GGGTKLTVL

Figure 17C-19

SEQ ID NO 20:
AELELTQPPSVSGTPGQRVTISCSGSSSNIAGNTVYWYQQLPGAAPKLLIYY
NDQRPSGVPDRFSGSKSGTSSSLTISGLQSEDEAYYYCATWDEDVNGWVF
GGGTKLTVL

Figure 17C-20

SEQ ID NO 21:
AELMLTQPHSASETPGQRVTISCSGSSSNIAGNTVYWYQQLPGAAPKLLIYY
NDQRPSGVPDRFSGSKSGTSSSLAISGLQSEDEAYYYCATWDEDVNGWVF
GGGTELTVL

Figure 17C-21

SEQ ID NO 22:
AELVLTQSPSASETPGQRVTISCSGSSSNIAGNTVYWYQQLPGAAPKLLIYY
NDQRPSGVPDRFSGSKSGTSSSLAISGLQSEDEAYYYCATWDEDVNGWVF
GGGTKVTVL

Figure 17C-22

SEQ ID NO 23:
AELVLTQPPSVSGTPGQRVTISCSGSSSHIGNNYVYWYQHLPGTAPKLLIYS
NDQRPSGVPDRFSASKSATSASLAISGLRSEDEADYYCAAWDDSQGGVFG
GGTKVTVL

Figure 17C-23

SEQ ID NO 24:
AELVLTQPPSVSGTPGQRVTISCSGSSSHIGSNYVYWYQQLPGTAPKILIYS
NDQRPAGVPDRFSASKSGTSASLAISGLRSEDEADYYCAAWDDGQGGVFG
GGTKLTVL

Figure 17C-24

DRUG DELIVERY TO HUMAN TISSUES BY SINGLE CHAIN VARIABLE REGION ANTIBODY FRAGMENTS CLONED BY PHAGE DISPLAY

CROSS-REFERENCE TO RELATED APPLICATIONS

This is a National Stage application of PCT International Application No. PCT/US2008/00288, filed Jan. 9, 2008, which in turn claims the benefit pursuant to 35 U.S.C. §119(e) of U.S. Provisional Application No. 60/879,700, filed on Jan. 9, 2007 and U.S. Provisional Application No. 60/903,394, filed on Feb. 26, 2007, which are hereby incorporated by reference in their entirety herein.

STATEMENT REGARDING FEDERALLY SPONSORED RESEARCH OR DEVELOPMENT

This invention was supported in part by funds obtained from the U.S. Government (National Institutes of Health Grant Numbers RO1AR052672 and RO1AR48223), and the U.S. Government may therefore have certain rights in the invention.

BACKGROUND OF THE INVENTION

Pemphigus vulgaris (PV) and pemphigus foliaceus (PF) are potentially fatal autoimmune blistering skin diseases in which autoantibodies against desmoglein 3 (Dsg3) and Dsg1, cell surface desmosomal adhesion molecules, cause loss of keratinocyte cell adhesion (Payne et al., 2004, Curr. Opin. Cell Biol. 16:536-543). PF is characterized by superficial blistering of only the skin, while PV typically presents with suprabasilar blistering of mucous membranes, which may extend to involve skin. ELISA studies have shown that all PF sera contain autoantibodies against Dsg1, and sera from patients with mucosal-dominant PV react mainly against Dsg3 (Ishii et al., 1997, J. Immunol. 159:2010-2017; Ding et al. 1997. J. Invest. Dermatol. 109:592-596; Amagai et al., 1999, J. Am. Acad. Dermatol. 40:167-170). PV patients who progress from mucosal to mucocutaneous lesions develop anti-Dsg1 in addition to anti-Dsg3 antibodies (Miyagawa et al., 1999, Br. J. Dermatol. 141:1084-1087). The anti-Dsg antibodies in pemphigus sera are pathogenic, since neonatal mouse passive transfer studies have shown that the extracellular domains of Dsg1 and Dsg3 can adsorb out pathogenic antibodies from PF and PV sera, respectively, and affinity-purified anti-Dsg1 or anti-Dsg3 antibodies cause characteristic disease (Amagai et al., 1994, J. Clin. Invest. 94:59-67; Amagai et al., 995, J. Invest. Dermatol. 104:895-901; Ding et al., 1999, J. Invest. Dermato, 112:739-743).

The autoantibody profile in pemphigus patients' sera, together with studies demonstrating the compensatory intercellular adhesive functions of Dsg1 and Dsg3 in normal epidermis (Wu, et al., 2000, N. Engl. J. Med. 343:31-35), accounts for the clinical and histologic sites of blister formation in pemphigus. In mucous membranes, Dsg1 is expressed predominantly in the superficial epithelium, while Dsg3 is expressed throughout (Shirakata et al., 1998, J. Invest. Dermatol., 110:76-78, Mahoney et al., 1999 J. Clin. Invest. 103:461-468). In skin, Dsg1 is expressed throughout the epidermis (predominantly superficially), while Dsg3 is expressed only in the basal and immediate suprabasal layers. Thus, consistent with the concept of "desmoglein compensation" (Wu et al., 2000, N. Engl. J. Med. 343:31-35), in PF, anti-Dsg1 antibodies cause blistering in the superficial epidermis, where Dsg1 but not Dsg3 is expressed, but they do not affect oral mucosa because of compensatory adhesion provided by Dsg3 throughout the epithelium. In mucosal PV, anti-Dsg3 antibodies cause blistering only in the basal layers of the mucosa, where Dsg3 is present without Dsg1 to compensate. The development of anti-Dsg1 in addition to anti-Dsg3 antibodies in mucocutaneous PV results in the extension of suprabasilar blistering to the epidermis.

Currently, therapy for PV is nonspecific and relies on general suppression of the immune system to ultimately lower antibody titers. To develop more targeted therapies for this disease, a finer understanding of both the T cell and the B cell immune response will be needed. A number of studies have examined the role of T lymphocytes in disease, through MHC-linked susceptibility, TCR gene usage patterns, the identification of T cell subsets contributing to disease, and the characterization of T regulatory cells in patients and MHC-matched controls (Wucherpfennig et al., 1995, Proc. Natl. Acad. Sci. U.S.A. 92:11935-11939; Hacker-Foegen et al., 2003, J. Invest. Dermatol., 121:1365-1372; Lin, et al., 1997, J. Clin. Invest. 99:31-40; Veldman et al., 2004, J. Immunol. 172:6468-6475; Nishifuji et al., 2000, J. Invest. Dermatol. 114:88-94).

Many more studies have focused on characterizing pemphigus autoantibodies. The relationship of the valence of autoantibodies to pathogenicity has been examined (Rock et al., 1990, J. Clin. Invest. 85:296-299; Mascaro, et al., 1997, Clin. Immunopathol., 85:90-96). Fab' monovalent fragments, prepared by proteolytic degradation and alkylation/reduction of whole IgG from both PF and PV sera, cause histologically typical disease when passively transferred to neonatal mice. Furthermore, these monovalent antibody fragments may be more potent on a molar basis than bivalent IgG autoantibodies.

A number of anti-desmoglein antibodies have now been characterized and many of them do not appear to result in loss of keratinocyte adherence. Such human-derived, non-pathogenic antibodies may satisfy a need in the art for targeting molecules to specific tissues for the treatment of various non-pemphigus-associated conditions. The present invention meets these needs.

SUMMARY OF THE INVENTION

The invention includes a composition comprising an antibody-protein fusion molecule, wherein the antibody is non-pathogenic to its target tissue, and the protein a therapeutic protein.

The invention also includes a composition comprising an antibody, wherein the antibody is non-pathogenic to its target tissue, and the composition further comprises a non-protein molecule. In one embodiment, non-protein molecule is conjugated with the antibody.

In one embodiment, the antibody binds to a target molecule associated with the epidermis. In another embodiment, the antibody binds to a target molecule associated with the basement membrane. In yet another embodiment, the antibody binds to a target molecule selected from the group consisting of Dsg1, Dsg3, BP180, and any combination thereof. In another embodiment, the antibody is an scFv.

In one embodiment, the antibody is derived from a mammal having an autoimmune disease. The autoimmune disease is selected from the group consisting of pemphigus vulgaris, pemphigus foliaceus, and bullous pemphigoid. In another embodiment, the antibody is derived from a normal or otherwise a healthy mammal.

In one embodiment, the therapeutic protein is an enzyme. In another embodiment, the therapeutic protein is a pro-apoptoic protein.

The invention includes a method of treating an individual in need thereof, comprising administering to the individual a composition comprising an antibody-protein fusion molecule, wherein the antibody is non-pathogenic to its target tissue, and the protein is a therapeutic protein, wherein the antibody and the therapeutic protein bind to different molecules in, or delivered to, the tissue, wherein said composition is capable of delivery of said therapeutic protein to the site targeted by the composition or a site proximal to the site targeted by the composition, thereby treating said individual. Preferably, the antibody binds to a target molecule associated with the basement membrane and/or epidermis.

In another embodiment, the individual has a condition associated with the basement membrane and/or epidermis.

The invention also includes a method of treating an individual in need thereof, comprising administering to the individual a composition comprising an antibody, wherein the antibody is non-pathogenic to its target tissue, and the composition further comprises a non-protein molecule, wherein the antibody and the non-protein molecule bind to different molecules in, or delivered to, the tissue, wherein the composition is capable of delivery of the non-protein molecule to the site targeted by the composition or a site proximal to the site targeted by said composition, thereby treating the individual. Preferably, the antibody binds to a target molecule associated with the basement membrane and/or epidermis.

In another embodiment, the individual has a condition associated with the basement membrane and/or epidermis.

The invention also includes a composition comprising an antibody-laser absorbing molecule (LAM) fusion molecule, wherein the antibody is non-pathogenic to its target tissue, and LAM has the property of absorbing at least one specific type of laser energy.

The invention also includes a method of treating an individual in need thereof, comprising administering to the individual a composition comprising an antibody-laser absorbing molecule (LAM) fusion molecule, wherein the antibody is non-pathogenic to its target tissue, and the LAM has the property of absorbing at least one specific type of laser energy, wherein the composition enables the delivery of said LAM to a site targeted by the composition or a site proximal to the site targeted by the composition, and directing laser energy at the composition, wherein the composition absorbs the laser energy, thereby treating the individual. Preferably, the antibody binds to a target molecule associated with the basement membrane and/or epidermis.

In another embodiment, the individual has a condition associated with the basement membrane and/or epidermis.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A-1C, is a series of images depicting isolation of monovalent scFv mAbs. (FIG. 1A) ScFv nomenclature. (D3), (D1), or (D31) indicates the antigens used to select anti-Dsg mAbs from the scFv phage display library (Dsg3, Dsg1, or both, respectively). This is followed by a unique heavy chain and light chain nucleotide sequence designation. For mAbs that share the same clonal origin (same VDJ rearrangement) but differ in sequence because of somatic hypermutation, lower-case letters indicate unique members of a given clone (see Discussion and legend to FIG. 9). (FIG. 1B) Soluble scFv mAbs were purified by nickel-chelation chromatography (see Methods). Two representative scFvs are shown by Coomassie blue staining after SDS-PAGE. (FIG. 1C) Gel-filtration HPLC demonstrates that scFvs are primarily monomeric in solution. Transferrin (Tf, 75 kDa) and carbonic anhydrase (CA, 30 kDa) served as protein standards, with 0.1 M Mops as a marker of the total volume of the column. The percentage of monomeric protein is shown, calculated from the area under the curve.

FIGS. 2A-2H, is a series of images depicting indirect immunofluorescence (IIF) of scFv mAbs on human and mouse epidermis. The ScFv mAb used as primary antibody for staining human (FIGS. 2A-2E) and mouse (FIG. 2F-2H) epidermis is indicated in each panel. Magnification, ×400.

FIGS. 3A-3B, is a series of images depicting characterization of scFv mAb desmoglein-binding specificity by ELISA. (FIG. 3A) Patterns of the binding of selected scFv mAb clones to Dsg1 and Dsg3. (D3)3c/9 was isolated from a library panned on Dsg3 but showed quantifiable specificity for Dsg1, as shown in FIG. 3B. Similar results were obtained for mAb (D3)3a/9.

FIGS. 4A-4B, is a series of images depicting epitopes recognized by PV scFv mAbs are blocked by sera from multiple pemphigus patients. (FIG. 4A) (D3)3c/9. Left: Inhibition of Dsg3 binding by all 8 PV sera. PVLIB is the plasma of the mucocutaneous PV patient from whom the phage display library was made. Black bars represent PV sera containing anti-Dsg3 antibodies only; gray bars indicate PV sera containing antibodies with both anti-Dsg3 and anti-Dsg1 activity [PV(3+1) sera]. Right: Inhibition of Dsg1 binding by 3 of 5 PV(3+1) sera and 6 of 6 PF sera (white bars). (FIG. 4B) (D31)2/28. Left: Inhibition of Dsg3 binding by 7 of 8 PV sera and 0 of 6 PF sera. Right: Inhibition of Dsg1 binding by 4 of 5 PV(3+1) sera and 5 of 6 PF sera. Inhibition of greater than 20% was considered positive. NHS, normal human sera.

FIGS. 5A-5D, is a series of images depicting anti-Dsg scFv mAbs that are pathogenic in neonatal mice. (FIG. 5A) Injection of (D3)3c/9 alone into neonatal mice does not cause gross blistering; histologic examination (lower panel) supports this result. (FIG. 5B) Injection of (D3)3c/9 with low-dose exfoliative toxin a (ETA) demonstrates suprabasilar blistering. (FIG. 5C) Injection of (D31) 2/28 alone demonstrates superficial blistering in the granular layer of the epidermis. (FIG. 5D) Coinjection of (D3)3c/9 and (D31)2/28 demonstrates suprabasilar blistering. Magnification, ×400.

FIGS. 9A-9B, is a series of images depicting Heavy and light chain restriction of Dsg-panned scFv mAbs. (A) Dendrogram and CDR3 alignment of (D3), (D1), and (D31) heavy chain sequences. Heavy chain (HC) sequence analysis of 63 randomly selected mAbs from the PV autoantibody repertoire identified 12 different VDJ families (indicated as VDJ1-VDJ12). Each VDJ family shares a common B cell precursor, defined by a common CDR3 amino acid sequence. The presence of a letter suffix in the heavy chain indicates the presence of somatic mutations in the variable region outside the CDR3, which reflect genetic diversification of the original parental B cell clone. The VH gene family and gene segment usage is indicated for each of the 31 unique heavy chain sequences. (B) Unique pemphigus mAbs show restricted and nonoverlapping usage of heavy and light chain gene segments. The horizontal axis represents unique heavy chains, and the vertical axis represents the unique λ and κ light chains (based on nucleic acid sequence). The heavy chains are restricted into 12 VDJ groupings, whereas the light chain repertoire comprises 30 groupings, defined by a unique light chain junctional region. Of the 26, 24, and 13 randomly screened D3, D1, and D31 mAbs, 16, 22, and 5 unique heavy and light chain combinations, respectively, were identified (represented within the matrix as magenta, blue, and black boxes, respectively). In most cases, antibodies panned against a particular desmoglein bound only that desmoglein substrate. However, 2 mAbs, (D3)3a/9 and (D3)3c/9, although panned only against Dsg3, also weakly bound Dsg1 (indicated by asterisks).

FIG. 10, comprising FIGS. 10E-10G are images that depict another set of results conducted with scFv Px4-4. FIG. 10E is an image of a mouse and its epidermis following intraperitoneal injection of scFv Px4-4. No pathology is apparent (whereas the pathogenic Px4-1 causes blisters under the same conditions, not shown) FIG. 10F shows histology and immunofluorescence images of normal human skin in organ culture following intradermal injection of scFv Px4-4 or scFv Px4-3. Px4-4 scFv binds the cell surface of human keratinocytes without causing pathology as does Px4-3. FIG. 10G shows immunofluorescence images of mouse skin following intraperitoneal injection of Px4-4 scFv. In sum, FIG. 10 shows one example of an scFv (Px4-4), derived from a PV patient, that binds the cell surface of keratinocytes but does not cause apparent pathology.

FIGS. 12A and 12B, is a series of images depicting SDS-PAGE of baculovirus-produced recombinant scFv 4B3-EGFP protein (which has His tag and HA tag). ScFv 4B3 (also termed D(3)3c/9), derived from a pemphigus vulgaris patient by phage display, binds to Dsg3. FIG. 12A-Coomassie Blue. Lane 1 (on left), scFv 4B3-EGFP protein purified on nickel column; lane 2, 3-day supernatant of High Five cells infected with scFv 4B3-EGFP baculovirus; lane 3, molecular weight standards (indicated in kD). FIG. 12B-Immunoblot with anti-HA antibody. Lane 1,3-day supernatant of High Five cells; lane 2, scFv 4B3-EGFP protein from High Five supernatant purified on a nickel column. Molecular weight standard migrations shown on left.

FIG. 14, comprising FIG. 14A is a schematic of the modular baculovirus transfer vector used to produce the chimeric protein. FIG. 14B is a image of the EGFP fluorescence on the cell surface of epithelial cells after chimeric scFv-EGFP is incubated on a frozen section of monkey esophagus. In this case the scFv was 4B3. Incubation of the chimeric 4B3-EGFP with Dsg3 before incubation on the tissue abolishes the binding to monkey esophagus. FIG. 14C is an image of a Coomassie Blue staining on SDS-PAGE and Western blotting of the 4B3-EGFP chimeric protein $Ni^{2+}$-purified from the insect cell media. FIG. 14D is an image summarizing fluorimetry results of 4B3EGFP chimeric anti-Dsg3 protein before and after nickel adsorption (above) and Dsg3 adsorption (below). FIG. 14E shows EGFP fluorescence of mouse skin sections after injection of chimeric scFv-EGFP: a, b: 4B3EGFP intradermal injection; c, d, e: Px4-4EGFP intravenous injection; a, back; b and c, ear en face; d, tail; e, paw.

FIGS. 16A and 16B is a image depicting vectors used to produce mouse NC16A fusion proteins. FIG. 16A is an image depicting the vector used to produce the mouse NC16A domain of BP180 cloned as a chimeric molecule with maltose binding protein (MBP) which was used to immunize rabbits. FIG. 16B is an image depicting the vector used to produce mouse BP180 NC16A domain linked to glutathione S-transferase (GST), which was used as an ELISA substrate to test the MBP-NC16A-immunized rabbit sera for reactivity against NC16A.

FIG. 17, comprising FIGS. 17A through 17C, is a series of charts showing representative non-pathogenic scFvs. FIG. 17A is a chart depicting the makeup of anti-Dsg say clones, including the desmoglein specificity, heavy chain identifier, and light chain identifier. FIG. 17B is a chart depicting the identification of each heavy chain and light chain to the corresponding sequence identifier. FIG. 17C is a chart depicting the nucleic acid (SEQ ID NOs 1-12) and amino acid (SEQ ID NOs 13-24) sequence of the representative heavy and light chains.

DETAILED DESCRIPTION OF THE INVENTION

Figure 1:
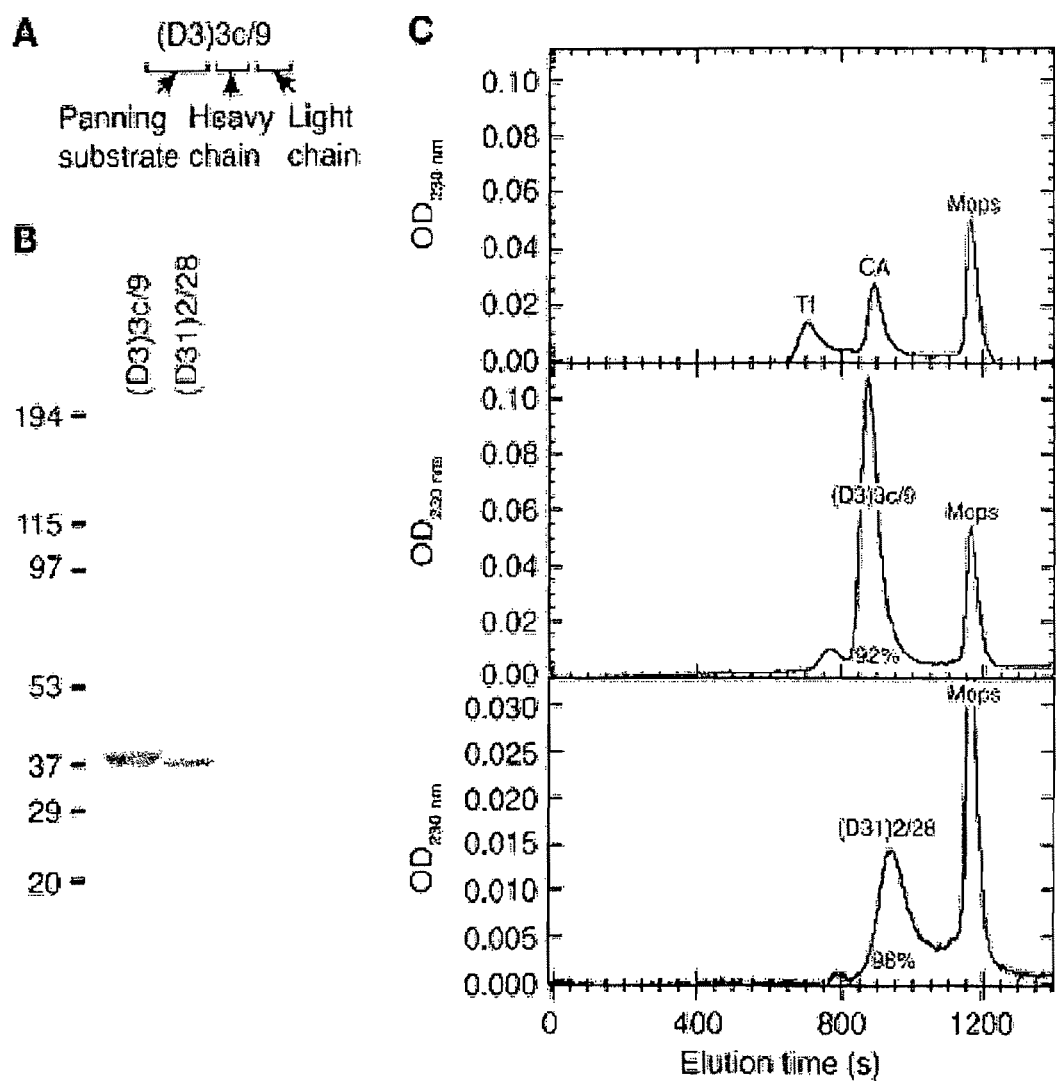
FIG. 1, comprising

To better understand the pathophysiology of pemphigus autoantibodies and to allow development of more specifically targeted therapies for diseases and disorders of all types, human monoclonal anti-Dsg antibodies were isolated from pemphigus patients. In part, the present invention uses antibody phage display to isolate clones of human anti-Dsg mAbs from a patient with active acute mucocutaneous PV, whose sera contained antibodies to both Dsg3 and Dsg1. This approach obviates the need for the immortalization of human B cells, a process that is efficient for the production of murine mAbs, but not for those of human origin (Stein et al., 1983, Cell. Immunol., 79:309-319; Roder et al., 1986, Methods Enzymol. 121:140-167). However, the invention should not be construed to be limited to antibodies derived from a diseased patient. Rather, the invention includes isolating min-pathogenic antibodies from any source. For example, human anti-Dsg autoantibodies can be isolated from naive phage display libraries generated from lymphocytes derived from healthy individuals with no evidence of pemphigus.

Phage display provided a large cohort of anti-Dsg mAbs, which were characterized on a phenotypic level to verify that these recombinant pemphigus mAbs recapitulate both the in vitro and the in vivo desmoglein-binding properties of pemphigus patient sera. Importantly, a number of non-pathogenic antibodies were identified. The non-pathogenic antibodies led to the present discovery that such non-pathogenic antibodies can be used to target therapeutic molecules to a specific site of interest in a mammal. Preferably, the mammal is a human. In an aspect of the invention, such antibodies are non-pathogenic to their target, e.g., target tissue.

The present invention provides, among other things, compositions and methods for treating autoimmune diseases, and for targeting proteins of interest, such as therapeutic proteins, to tissues involved in autoimmune diseases. According to the invention, non-pathogenic antibodies and/or antibody fragments isolated from humans can be used to deliver biologics, enzymes that activate drugs, protease inhibitors, and the like to human patients. In another aspect, scFv derived from various autoimmune patients (e.g. pemphigoid or Goodpasture's Disease) can be used to change the target of the non-pathogenic antibody or antibody fragment.

In one aspect, a condition or disease associated with activated lymphocytes or other inflammatory cells that cross basement membrane to infiltrate epithelia can be treated using a composition comprising a non-pathogenic anti-basement membrane or anti-epithelialscFv linked to a pro-apoptotic protein. Such a composition is capable of forming an "immunological gate or barrier" that regulate lymphocytes as they attempt to migrate through the basement membrane (e.g., into the epidermis). The compositions of the invention can be used to protect a tissue by targeting a desirable pro-apoptotic protein to the basement membrane or epithelia to regulated that trafficking of leukocytes that are capable of migrating through the basement membrane to the epithelia. The composition is useful to alleviate or treat human diseases, including but are not limited to psoriasis, graft versus host disease, vitiligo, and the like. In another embodiment, lung basement membrane can be targeted, for example using scFv cloned from Goodpasture's patients. In any event, agents targeted to basement membrane or epithelia of specific tissues can act as a "gate" or "barrier" to downregulate inflammatory cells such as lymphocytes.

The present invention also provides compositions and methods that alleviate conditions associated with the epidermis. For example, agents can be targeted to the hair follicle to decrease inflammation in inflammatory disease. Similarly, agents such as growth factors which can induce hair growth can be targeted to the hair follicle to induce hair growth. In addition, agents that bind cell surface receptors and decrease hair growth can be targeted to the hair follicle to decrease unwanted hair growth.

Definitions

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and nucleic acid chemistry and hybridization are those well known and commonly employed in the art.

Standard techniques are used for nucleic acid and peptide synthesis. The techniques and procedures are generally performed according to conventional methods in the art and various general references (e.g., Sambrook and Russell, 2001, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The nomenclature used herein and the laboratory procedures used in analytical chemistry and organic syntheses described below are those well known and commonly employed in the art. Standard techniques or modifications thereof, are used for chemical syntheses and chemical analyses.

The articles "a" and "an" are used herein to refer to one or to more than one (i.e., to at least one) of the grammatical object of the article. By way of example, "an element" means one element or more than one element.

As used herein, to "alleviate" a disease, disorder or condition means reducing the severity of one or more symptoms of the disease, disorder or condition.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytidine, "G" refers to guanosine, "T" refers to thymidine, and "U" refers to uridine.

A "polynucleotide" means a single strand or parallel and anti-parallel strands of a nucleic acid. Thus, a polynucleotide may be either a single-stranded or a double-stranded nucleic acid.

The term "nucleic acid" typically refers to large polynucleotides.

The term "oligonucleotide" typically refers to short polynucleotides, generally, no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

A "portion" of a polynucleotide means at least at least about twenty sequential nucleotide residues of the polynucleotide. It is understood that a portion of a polynucleotide may include every nucleotide residue of the polynucleotide.

As used herein, the terms "gene" and "recombinant gene" refer to nucleic acid molecules comprising an open reading frame encoding a polypeptide. Such natural allelic variations can typically result in 1-5% variance in the nucleotide sequence of a given gene. Alternative alleles can be identified by sequencing the gene of interest in a number of different individuals. This can be readily carried out by using hybridization probes to identify the same genetic locus in a variety of individuals. Any and all such nucleotide variations and resulting amino acid polymorphisms or variations that are the result of natural allelic variation and that do not alter the functional activity are intended to be within the scope of the invention.

Moreover, nucleic acid molecules encoding proteins from other species (homologs), which have a nucleotide sequence which differs from that of the human proteins described herein are within the scope of the invention. Nucleic acid molecules corresponding to natural allelic variants and homologs of a cDNA of the invention can be isolated based on their identity to human nucleic acid molecules using the human cDNAs, or a portion thereof, as a hybridization probe according to standard hybridization techniques under stringent hybridization conditions.

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

A "recombinant polypeptide" is one which is produced upon expression of a recombinant nucleic acid.

By the term "specifically binds," as used herein, is meant a compound, e.g., a protein, a nucleic acid, an antibody, and the like, which recognizes and binds a specific molecule, but does not substantially recognize or bind other molecules in a sample.

As used herein, to "treat" means reducing the frequency with which symptoms of a disease, disorder, or adverse condition, and the like, are experienced by a patient. Such non-limiting conditions include bona fide illness as well as cosmetic or other conditions for example removal of unwanted hair or treating baldness where hair growth is desired.

A molecule (e.g., a ligand, a receptor, an antibody, and the like) "specifically binds with" or "is specifically immunoreactive with" another molecule where it binds preferentially with the compound and does not bind in a significant amount to other compounds present in the sample.

The term "antibody," as used herein, refers to an immunoglobulin molecule which is able to specifically bind to a specific epitope on an antigen.

Antibodies can be intact immunoglobulins derived from natural sources or from recombinant sources and can be immunoreactive portions of intact immunoglobulins. Some antibodies are typically tetramers of immunoglobulin molecules. The antibodies in the present invention may exist in a variety of forms including, for example, polyclonal antibodies, monoclonal antibodies, chimeric, hybrid, Fv, Fab and F(ab)$_2$, as well as single chain antibodies, primatized, and humanized antibodies. Antibody fragments refer to antigen-binding immunoglobulin peptides which are at least about 5 to about 15 amino acids or more in length, and which retain the capacity to bind to the antigen. (Harlow et al., 1999, Using Antibodies: A Laboratory Manual, Cold Spring Harbor Laboratory Press, NY; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

By the term "Fab/phage" as used herein, is meant a phage particle which expresses the Fab portion of an antibody. (I now see you added this later).

The term "antibody-protein fusion molecule" as used herein, refers to a fusion or chimeric molecule comprising at least two components, including a targeting moiety and peptide or protein. The fusion molecule can also comprise at least two components, including a targeting moiety and a therapeutic moiety. In other embodiments, the fusion molecule can comprise at least two components, including a targeting moiety and a non-protein molecule.

As used herein, "non-pathogenic" when used in conjunction with the term "antibody" refers to an antibody that does not appreciably alter normal homeostasis of a mammal when introduced into the mammal. Preferably, the non-pathogenic antibody does not have an appreciable adverse effect on the host mammal when present in the host mammal.

By the term "scFv/phage" are used herein, is meant a phage particle which expresses the Fv portion of an antibody as a single chain.

"Phage," or "phage particle," as these terms are used herein, include that contain phage nucleic acid encoding, inter alia, an antibody. This is because, as would be appreciated by the skilled artisan, unlike peptide phage display (where the peptide DNA insert is small and it is actually cloned into the phage DNA), the larger scFv or Fab DNA inserts are actually cloned into, among other things, a plasmid. Thus, the nucleic acid encoding the antibody, e.g., a plasmid such as, but not limited to, pComb3X, not only comprises a plasmid origin of replication, but also a phage (e.g., M13) origin of replication sequence and an M13 packaging sequence, so that when the nucleic acid is produced, a helper phage can be used to provide the required phage (e.g., M13) proteins in trans to make "phage-like" particles. That is, these particles resemble phage on the outside, but on the inside they contain plasmid (also referred to as a "phagemid") DNA. In other words, the phagemid DNA need not encode any M13 phage proteins, except a piece of M13 gene III fused to the DNA for antibody or peptide. Thus, it should be understood that the terms "phage," "phage particle," "phage-like particle" and "phagemid" are used interchangeably herein.

As used herein, the term "washing" refers to removing at least one component from a mixture of at least two components. By way of a series of non-limiting examples, salt can be washed from a protein by dialyzing a protein, an antibody can be removed from the outside of a cell by altering the salt conditions of the cell medium or by removing the salt from the cell medium altogether, and an unbound phage can be removed from a cell suspension by separating the cell from the phage using a gel filtration technique.

As used herein, a "therapeutic protein" refers to a protein, a polypeptide, an antibody, a peptide or fragment or variant thereof, having one or more therapeutic and/or biological activity. Therapeutic proteins encompassed by the invention include but are not limited to, proteins, polypeptides, peptides, antibodies, and biologics. (The terms peptides, proteins, and polypeptides are used interchangeably herein.) Thus a fusion protein of the invention may contain at least a fragment or variant of a therapeutic protein, and/or at least a fragment or variant of an antibody. Additionally, the term "therapeutic protein" may refer to the endogenous or naturally occurring correlate of a therapeutic protein.

By a polypeptide displaying a "therapeutic activity" or a protein that is "therapeutically active" is meant a polypeptide that possesses one or more known biological and/or therapeutic activities associated with a therapeutic protein such as one or more of the therapeutic proteins described herein or otherwise known in the art. As a non-limiting example, a "therapeutic protein" is a protein that is useful to treat, prevent or ameliorate a disease, condition or disorder. For example, a non-exhaustive list of "therapeutic protein" portions which may be comprised by a fusion protein of the invention includes, but is not limited to fas ligand, tumor necrosis factor alpha receptor, CD200, tumor necrosis factor-related apoptosis-inducing ligand (TRAIL), transforming growth factor alpha (TGF alpha), programmed death ligand (PD-L1), and epidermal growth factor. Other useful therapeutic proteins include enzymes, such as those that activate drugs, or those that can act to inhibit an undesirable biological reaction in a mammal.

A "targeting moiety" or a "cell-specific targeting moiety" is used herein to refer to a molecule comprising an antibody to one or more particular soluble protein, tissue marker, cell-surface antigen, cell marker, growth factor, hormone, or cytokine. In one aspect, the targeting moiety of a chimeric composition is an antibody, such as a single chain antibody, an antibody fragment, a Fab, and the likes.

As used herein, "pro-apoptotic molecules" refers to any molecule that is capable of inducing cell death through apoptotic mechanisms. The pro-apoptotic molecules can induce programmed cell death upon entry into the target cell. Apoptosis, or programmed cell death, is a fundamental process controlling normal tissue homeostasis by regulating a balance between cell proliferation and death. Examples of pro-apoptotic molecules include but are not limited to granzymes, Bcl-2 family members (Bax, Bak, Bcl-Xs, Bik, Bok, Bipla, and the like), and caspases.

By "laser absorption molecule," as the term is used herein, is meant a molecule that can absorb laser light radiation. The term is also used to indicate a molecule that can absorb any type of laser energy, including light-based laser energy, but also including any form of electromagnetic or particle-based laser energy.

As used herein, the term "laser absorbing molecule complex" refers to a complex comprising at least one laser absorbing molecule and at least one antibody or scFv of the invention. A complex can have the two or molecules associated by way of a non-covalent interaction, or by way of one or more covalent interactions.

DESCRIPTION OF THE INVENTION

The present invention provides a system for a type of targeted therapy to deliver desirable agents, such as proteins in vivo to a mammal, preferably a human. In one embodiment, the invention provides a system to deliver a biologically active protein to the epidermis of a human. In another embodiment, the invention provides a system to deliver a biologically active protein to the basement membrane of a human. Preferably, the system includes a chimeric molecule comprising at least two components, including a targeting moiety and a therapeutic peptide (e.g., a cytotoxic moiety, an apoptosis-inducing moiety, laser absorbing moiety, and the like). In specific embodiments, the targeting moiety is an antibody fragment. Preferably, the targeting moiety is non-pathogenic.

The invention also provides for any nonpathogenic antibody useful in targeted therapy. In one embodiment, the invention includes any nonpathogenic autoimmune or autoreactive human monoclonal antibodies useful in targeted therapy such as drug delivery.

In one embodiment of the invention, agents can be targeted to a basement membrane or to the surface of epithelial cells to act as a "gate" or "barrier" to downregulate inflammatory cells such as lymphocytes. A composition comprising a non-pathogenic anti-basement membrane or anti-epithelial scFv linked to an agent such as a pro-apoptotic protein can be used to form an "immunological gate" that regulate lymphocytes as the lymphocytes attempt to migrate through the basement membrane and into the epithelia. The compositions of the invention can be used to protect a tissue by targeting a desirable pro-apoptotic protein to the basement membrane and/or cell surface of the epithelia to regulate that trafficking of leukocytes that are capable of migrating through the basement membrane.

In another embodiment, the invention includes a nonpathogenic antibody that alleviates conditions of the epidermis. For example, a nonpathogenic antibody can be used to target the epidermis for cosmetic purposes. Agents such as growth factors which can induce hair growth can be targeted to the hair follicle to induce hair growth. In addition, agents that bind cell surface receptors and decrease hair growth can be targeted to the hair follicle to decrease unwanted hair growth.

Methods and Compositions

The present invention relates, in part, to single chain variable fragments (scFv) isolated from patients having an autoimmune disease. The cloned scFv are themselves non-pathologic, and can be used to deliver biologically active proteins or other molecules to specific tissues. In an embodiment, an scFv binds desmoglein 3 (Dsg3), Dsg 1, or any combination thereof. In another embodiment, non-pathogenic scFv against Dsg1, cloned from pemphigus patients, are featured. In yet another embodiment, non-pathogenic scFv against Dsg3, cloned from pemphigus patients are featured. In yet another embodiment, non-pathogenic scFv that bind both Dsg1 and Dsg3, are included. In other embodiments of the invention, an scFv can be fused to an agent, wherein the agent can specifically bind to another protein, wherein the protein is involved in a disease, disorder or condition.

The present invention also provides for antibodies that target the basement membrane of the epidermis. In one embodiment, the antibody is derived from a bullous pemphigoid patient. The cloned antibody (e.g. an scFv) is useful for delivering a biologically active protein or other molecules to the basement membrane of the epidermis. An exemplary basement membrane target protein is BP180.

The present invention demonstrates for the first time that autoantibodies isolated from a patient's immune system, and in particular, the non-pathogenic monoclonal antibodies, have a unique therapeutic value. Since such scFv are limited to variable regions of immunoglobulins, and because they can be derived from humans, these antibodies would not be expected to generate a significant immune response in the human. Furthermore, the relatively small size of such antibodies, when compared with the 6-fold larger IgG molecule, facilitates tissue penetration and overcomes problems faced with larger antibody molecules.

scFv according to the invention can be cloned by phage display from other types of patients (e.g., those with bullous pemphigoid, cicatricial pemphigoid or epidermolysis bullosa acquisita) with autoimmune diseases against other parts of epidermis, such as basement membrane. Since in these anti-basement membrane diseases it is thought that the effector region of IgG is necessary for pathogenicity, most, if not all, of such scFv according to the invention would be expected to be non-pathogenic. In this embodiment of the invention, scFv are used to bind to an antigenic target for a longer period of time than those scFvs that bind the cell surface of epithelial cells because basement membrane does not turn over rapidly.

In another embodiment, an antibody, such as an scFv, according to the invention can be used to deliver a therapeutic protein or peptide to a patient. As described in detail elsewhere herein, an scFv specific for Dsg3, for example, can be used to deliver a non-native protein to the skin of a mammal. This is because it has been shown herein that an scFv, fused to another protein (e.g., a green-fluorescent protein), can be used to target the protein to Dsg3 in the skin of a mammal. As will be understood by the skilled artisan, when armed with the disclosure set forth herein, the present invention is applicable to other scFvs, and to other antibody molecules with different antigenic specificities, as well as to other fusion proteins, such as any therapeutic protein or peptide.

Autoimmune disease patients suffering from the presence of antibodies specific for other tissues (such as Goodpasture's Disease, which involves lung and kidney basement membranes) can be used to clone non-pathogenic scFv to target those tissues, according to the present invention. Any biologically active protein, of which the cDNA sequence can be determined, can be delivered to a patient, according to the present invention, as described in detail elsewhere herein.

As will be understood by one of skill in the art, when armed with the disclosure set forth herein, there are various types of proteins that can be used as a therapeutic protein according to the invention. By way of a non-limiting example, an enzyme that can activate a drug is a useful therapeutic protein according to the invention. A patient can be administered an inactive pro-drug. A therapeutic protein can be administered to a patient using a targeted delivery composition and method according to the invention, in order to activate the pro-drug at only those specific locations to which the enzyme is targeted. In this way, the present invention is advantageous for reducing non-specific or unwanted effects of drug therapy.

Other therapeutic proteins and uses include, but are not limited to: a) targeting Fas Ligand (FasL) to epidermis or hair follicle epithelium to kill activated lymphocytes causing disease (e.g. psoriasis, inflammatory alopecias); b) targeting TNF-alpha with TNF-alpha receptor in psoriasis or other inflammatory diseases; c) targeting protease inhibitors (e.g., alpha 1 antitrypsin) to lung to reduce damage of proteases causing emphysema, or to other tissues to reduce inflammation amplified by proteases; d) targeting enzymes to tissue that can activate prodrugs (e.g., carboxypeptidase A to activate methotrexate-phenylalanine in psoriasis, or alkaline phosphatase to activate other prodrugs); e) targeting ligands to tissue to cause or inhibit growth (e.g., TGF-alpha, EGF, or other ligands that might induce hair growth or stimulate growth of atrophic epidermis); 0 targeting non-protein drugs that are chemically ligated to a targeting scFv.

Various proteins have been described that under certain circumstances can induce apoptosis and/or inhibit proliferation of activated lymphocytes, and in some cases other leukocytes. Exemplary pro-apoptotic proteins include but are not limited to FasL, PD-L1, and TRAIL. These proteins can be cloned as chimeric proteins in combination with the antibodies of the invention, for example anti-epidermal scFv or anti-basement membrane scFv. These chimeric molecules can be tested in mouse disease models in which activated lymphocytes or other leukocytes infiltrate epidermis.

The prototypic so-called "death receptor" is Fas (CD95), a tumor necrosis factor receptor family member. Its interaction with FasL induces apoptosis of activated lymphocytes in various systems. Like various other TNF family ligands, FasL spontaneously forms a trimer, thus a chimeric scFv-FasL protein would also be expected to form a trimer. Similarly, a chimeric scFv-TNF would also be expected to do so.

In various physiological situations, the FasL provides immunological protection by inactivating invading activated lymphocytes. For example, corneal epithelial cells express FasL that is thought to protect the cornea from inflammation and to maintain it as an immunologically privileged site that allows allogeneic transplantation. FasL is also found in testes, mostly on sperm, and may play a role in making testes an immunologically privileged site or protecting sperm from immune attack. FasL may also play a role in preventing activated lymphocytes from trafficking between mother and fetus.

Similarly to FasL, TRAIL is a member of the TNF family. TRAIL is synthesized as a type II transmembrane protein, and forms a trimeric ligand. The TRAIL trimeric ligand is stabilized by a zinc ion. TRAIL has been shown to mediate apoptotic cell death of activated CD8+ and CD4+ lymphocytes and lymphocyte clones, lymphocyte transformed cell lines, neutrophils and other cells (e.g. tumor cells) expressing appropriate TRAIL receptors. TRAIL has also been shown to decrease autoimmune inflammation in diseases such as experimental autoimmune encephalomyelitis, bacterial meningitis, and autoimmune arthritis, although in some cases it may due so by blocking proliferation of lymphocytes without causing an obvious increase in apoptosis.

PD-L1 is a B7 family member that in most systems causes transduction of a signal that inhibits proliferation of activated T cells, although in some cases causes their proliferation and activation. Similar to mFasL and TRAIL, PD-L1 is able to downregulate the immune response in immunologically privileged sites such as the eye and the placenta where it is expressed on cell surfaces and is thought to be one of the mediators of peripheral T cell tolerance. Also similar to some of the TNF family members, PD-L1 has been shown to decrease the immune reaction in experimental autoimmune encephalomyelitis, to promote allograft survival in some systems, and its genetic deletion leads to autoimmunity in mice. PD-L1 expression is induced on keratinocytes by interferon γ, which is believed to be a mechanism to down-regulate the inflammatory response in epidermis.

In another embodiment, chemical conjugation or other means is used to conjugate scFv to nonproteinaceous moieties, e.g. carbohydrates, inorganic molecules/drugs, among others. Thus, by way of a non-limiting example, for any disease that is caused by inflammation in the epidermis, biologically active proteins that down-modulate the immune response can be targeted to the epidermis, either in the basement membrane or to the epithelial cells. In one aspect, tumor necrosis factor blockers are used to treat psoriasis, which is believed to be rooted in an autoimmune response in the epidermis. Instead of administering anti-inflammatory biological response modifiers throughout a patient's body, the modifiers can be targeted to the epidermis according to the present invention. Additionally, by way of another non-limiting example, agents can be targeted to the hair follicle to decrease inflammation in the instance of inflammatory disease. Similarly, agents such as growth factors which can induce hair growth can be targeted to the hair follicle to induce hair growth. Further still, agents that bind cell surface receptors and decrease hair growth can be targeted to the hair follicle to decrease unwanted hair growth.

In another embodiment of the invention, proteolytic inhibitors (e.g. alpha-1 anti-trypsin) can be targeted to lung basement membrane using scFv which were cloned from Goodpasture's patients. Agents targeted to basement membrane of specific tissues can act as a "gate" to downregulate inflammatory cells such as lymphocytes (e.g. with Fas ligand or CD200 or other molecules thought to downregulate their activity).

The skilled artisan will understand, when armed with the disclosure set forth herein, that antibodies and/or scFvs can be isolated from any autoimmune patient, in order to obtain an antibody or scFv according to the invention. Such antibodies or scFvs which are non-pathogenic are therefore useful in the present invention to target one or more therapeutic molecules to a specific site within the body.

In another embodiment of the present invention, one or more molecules that can absorb laser emissions can be delivered to a target tissue, cell, or location, by use of an antibody or scFv of the invention.

By way of a non-limiting example, anti-desmoglein antibodies derived from a patient afflicted with pemphigus vulgaris can be complexed with one or more laser absorbing molecules. As will be understood by the skilled artisan, when armed with the disclosure set forth herein, the manner in which a laser absorbing molecule is complexed with an antibody or scFv of the invention will vary based on the desired function of the complex, as well as the chemical and physical nature of the laser absorbing molecule (e.g., a protein-based laser absorbing molecule can be chemically bonded to an antibody or scFv of the invention, or in the alternative, can be made as a fusion protein with the antibody or scFv, using molecular biology techniques known in the art).

In this way, in one non-limiting example of the invention, anti-desmoglein antibodies derived from a patient afflicted with pemphigus vulgaris can deliver such a laser absorption molecule to the "bulge" of hair follicles that contain the stem cell of a hair follicle. Because hair follicle bulge cells turn over very slowly (a characteristic of stem cells), the antibody can remain bound to these cells for an extended period of time. Other cells would be turning over more rapidly and the new cells replacing such rapidly-cycling cells would not be exposed to the antibody. The bulge cells can then be destroyed by use of laser energy, which can permanently destroy the hair follicle.

In another aspect of the invention, laser absorption molecules could similarly be used to target epidermal cells and destroy epidermal tumors (e.g. basal cell carcinoma). In this aspect of the invention, a tumor can be destroyed by first administering an scFv-laser absorbing molecule complex to a patient, such that the scFv complex specifically binds to the epidermal cell tumor, and then by directing an appropriate laser energy at the tumor. The skilled artisan will understand that an appropriate laser is selected based on the laser-absorbing characteristics of the laser absorbing molecule used in the complex.

The composition of the invention can be used to treat a skin disorder or condition where the pathology of the skin disorder or condition is associated with lymphocytic infiltration in the epidermis, dermis, and/or mucosa. A consequence of lymphocytic infiltration in the skin is inflammation. Psoriasis is a non-limiting example of a skin disease associated with lymphocytic infiltration. Psoriasis is a chronic skin disease, characterized by scaling and inflammation. The chronic skin inflammation of psoriasis is associated with hyperplastic epidermal keratinocytes and infiltrating mononuclear cells, including T cells, neutrophils and macrophages. The present invention also addresses the underlying T-cell disorder that results in an inflammatory condition of the skin. The invention allows for the targeting of therapeutic proteins such as pro-apoptotic proteins or immuno-regulators to the basement membrane of specific tissues to act as a "gate" to regulate infiltrating inflammatory cells such as lymphocytes. However, the invention should not be limited to a skin disorder as the composition can be used to form an "immunological gate" on the basement membrane of any tissue such as lung or kidney to regulate infiltrating cells to those tissues.

As a non-limiting example, composition of the invention can be used to alleviate or treat a condition or disorder associated with the skin. Preferably, the invention provides a fusion protein comprising a targeting moiety and a therapeutic moiety. In one aspect, the targeting moiety is a scFv that is capable of binding to a cell that naturally is present in healthy skin. An example of such a cell is a keratinocyte. In another aspect, the scFv is capable of binding to a molecule associated with the basement membrane. The targeting moiety serves to target the therapeutic moiety to the target cell (e.g., kerantinocyte) and/or tissue. In this way, the fusion protein can be used to produce an "immunological gate or barrier" where the therapeutic protein can be targeted to the basement membrane and/or keratinocytes to regulate activated lymphocytes or other inflammatory cells that are able to cross the basement membrane to infiltrate epithelia.

In another embodiment of the invention, the targeting moiety of the fusion protein binds to a first molecule and the therapeutic moiety of the fusion protein is delivered to a second molecule. The first and second molecule can be present on the same cell or alternatively, the first and second molecule can be present on different cells. In another aspect, the target moiety binds to a first molecule present on a first cell type and the therapeutic moiety binds to a second molecule present on a second cell type. In yet another aspect, the target moiety binds to a first molecule present on a basement membrane and the therapeutic moiety binds to a second molecule present on a cell, preferably an infiltrating lymphocyte. In some situations, the second molecule does not have to be present on a cell, but rather the second molecule can be a soluble protein. An example of a soluble protein is, a soluble mediator of inflammation that is not associated with any cell (e.g., TNFα).

A non-limiting example of the targeted therapy using the composition of the invention is exemplified by psoriasis. This is because psoriasis is characteristic of T-lymphocyte activation, proliferation, and cytokine release that leads to hyperproliferation of keratinocytes that overproduce Bcl-x (instead of normal Bcl-2). Although a few CD4+T-cells may be present in lesional skin, the majority of the cells are CD8+ lymphocytes that secrete the cytokines interleukin-2 and IFN-gamma. Psoriatic keratinocytes, due to the effect of IFN-gamma, contain Bcl-x, which protects against Fas-mediated apoptotic proteins. Thus, in one aspect, the fusion protein can be used to target the fusion protein to keratinocytes or the basement membrane whereby the therapeutic moiety (e.g., a pro-apoptotic protein) does not have a relatively adverse effect on the psoriatic keratinocytes, but rather has an adverse effect on proximal cells such as infiltrating lymphocytes.

Other conditions that can be addressed using the compositions of the invention include, but are not limited to graft-vs-host disease, baldness, unsightly female mustache hair, vitiligo, and the like. For example, the fusion protein is targeted to a cell or basement membrane where the fusion protein binds, and the therapeutic effect of the fusion protein is exhibited on a proximal cell or neighboring cell. The therapeutic effect of the fusion protein is the result of the delivery of the therapeutic moiety to a neighboring cell proximate to the cell or basement membrane. For example, in the situation of conditions associated with hair growth or hair removal, it is desirable to regulate the proximal melanocytes or hair stem cells that surround neighboring cells that express desmoglein.

Based on the disclosure set forth herein, the skilled artisan will understand that the invention is also useful to administer other antibodies, and other antibody complexes and/or fusions, to a patient in need of a specific treatment. The present disclosure provides guidance to the skilled artisan with respect to the source and properties of such antibodies, antibody fragments, or scFvs, among other things, based on the desired use of such antibody complexes and/or fusions.

Antibodies

As will be understood by one skilled in the art, any antibody that can recognize and bind to an antigen of interest is useful in the present invention. The binding, function, and effect of the binding of an antibody to the antigen can then be characterized further, as described in greater detail elsewhere herein. In an embodiment, an antigen of interest is Dsg3. In another embodiment, an antigen of interest is Dsg1. In yet another embodiment, an antigen of interest is BP180.

In an aspect of the invention, an antibody binds to Dsg3, but not to Dsg1. In another aspect, an antibody binds to Dsg1, but not to Dsg3. In yet another aspect, an antibody binds to both Dsg1 and Dsg3. Other antigenic proteins of the invention include other proteins involved autoimmune disorders. Examples of such proteins include, but are not limited to, proteins associated with skin-related autoimmune disorders such as bullous pemphigoid, cicatricial pemphigoid, or epidermolysis bullosa acquisita, as well as non-skin related autoimmune disorders involving other organs such as lung and kidney, including, but not limited to Goodpasture's disease.

Methods of making and using antibodies are well known in the art. For example, polyclonal antibodies useful in the present invention are generated by immunizing rabbits according to standard immunological techniques well-known in the art (see, e.g., Harlow et al., 1988, In: Antibodies, A Laboratory Manual, Cold Spring Harbor, N.Y.). Such techniques include immunizing an animal with a chimeric protein comprising a portion of another protein such as a maltose binding protein or glutathione (GSH) tag polypeptide portion, and/or a moiety such that the antigenic protein of interest is rendered immunogenic (e.g., an antigen of interest conjugated with keyhole limpet hemocyanin, KLH) and a portion comprising the respective antigenic protein amino acid residues. The chimeric proteins are produced by cloning the appropriate nucleic acids encoding the marker protein into a plasmid vector suitable for this purpose, such as but not limited to, pMAL-2 or pCMX.

However, the invention should not be construed as being limited solely to methods and compositions including these antibodies or to these portions of the antigens. Rather, the invention should be construed to include other antibodies, as that term is defined elsewhere herein, to antigens, or portions thereof. Further, the present invention should be construed to encompass antibodies, inter alfa, bind to the specific antigens of interest, and they are able to bind the antigen present on Western blots, in solution in enzyme linked immunoassays, in fluorescence activated cells sorting (FACS) assays, in magenetic-actived cell sorting (MACS) assays, and in immunofluorescence microscopy of a cell transiently transfected with a nucleic acid encoding at least a portion of the antigenic protein, for example.

One skilled in the art would appreciate, based upon the disclosure provided herein, that the antibody can specifically bind with any portion of the antigen and the full-length protein can be used to generate antibodies specific therefor. However, the present invention is not limited to using the full-length protein as an immunogen. Rather, the present invention includes using an immunogenic portion of the protein to produce an antibody that specifically binds with a specific antigen. That is, the invention includes immunizing an animal using an immunogenic portion, or antigenic determinant, of the antigen.

The antibodies can be produced by immunizing an animal such as, but not limited to, a rabbit, a mouse or a camel, with an antigenic protein of the invention, or a portion thereof, by immunizing an animal using a protein comprising at least a portion of the antigen, or a fusion protein including a tag polypeptide portion comprising, for example, a maltose binding protein tag polypeptide portion, covalently linked with a portion comprising the appropriate amino acid residues. One skilled in the art would appreciate, based upon the disclosure provided herein, that smaller fragments of these proteins can also be used to produce antibodies that specifically bind the antigen of interest.

Once armed with the sequence of a specific antigen of interest and the detailed analysis localizing the various conserved and non-conserved domains of the protein, the skilled artisan would understand, based upon the disclosure provided herein, how to obtain antibodies specific for the various portions of the antigen using methods well-known in the art or to be developed.

Further, the skilled artisan, based upon the disclosure provided herein, would appreciate that using a non-conserved immunogenic portion can produce antibodies specific for the non-conserved region thereby producing antibodies that do not cross-react with other proteins which can share one or more conserved portions. Thus, one skilled in the art would appreciate, based upon the disclosure provided herein, that the non-conserved regions of an antigen of interest (e.g., Dsg1, Dsg3, or BP180) can be used to produce antibodies that are specific only for that antigen and do not cross-react non-specifically with other proteins.

The invention encompasses monoclonal, synthetic antibodies, and the like. One skilled in the art would understand, based upon the disclosure provided herein, that the crucial feature of the antibody of the invention is that the antibody bind specifically with an antigen of interest. That is, the antibody of the invention recognizes an antigen of interest (e.g., Dsg1, Dsg3, or BP180) or a fragment thereof (e.g., an immunogenic portion or antigenic determinant thereof), on Western blots, in immunostaining of cells, and immunoprecipitates the antigen using standard methods well-known in the art.

One skilled in the art would appreciate, based upon the disclosure provided herein, that the antibodies can be used to immunoprecipitate and/or immuno-affinity purify their cognate antigen as described in detail elsewhere herein, and additionally, by using methods well-known in the art.

The skilled artisan would appreciate, based upon the disclosure provided herein, that that present invention includes use of a single antibody recognizing a single antigenic epitope but that the invention is not limited to use of a single antibody. Instead, the invention encompasses use of at least one antibody where the antibodies can be directed to the same or different antigenic protein epitopes.

The generation of polyclonal antibodies is accomplished by inoculating the desired animal with the antigen and isolating antibodies which specifically bind the antigen therefrom using standard antibody production methods such as those described in, for example, Harlow et al. (1988, In: Antibodies, A Laboratory Manual, Cold Spring Harbor, N.Y.).

Monoclonal antibodies directed against full length or peptide fragments of a protein or peptide may be prepared using any well known monoclonal antibody preparation procedures, such as those described, for example, in Harlow et al. (1988, In: Antibodies, A Laboratory Manual, Cold Spring Harbor, N.Y.) and in Tuszynski et al. (1988, Blood, 72:109-115). Quantities of the desired peptide may also be synthesized using chemical synthesis technology. Alternatively, DNA encoding the desired peptide may be cloned and expressed from an appropriate promoter sequence in cells suitable for the generation of large quantities of peptide. Monoclonal antibodies directed against the peptide are generated from mice immunized with the peptide using standard procedures as referenced herein.

Nucleic acid encoding the monoclonal antibody obtained using the procedures described herein may be cloned and sequenced using technology which is available in the art, and is described, for example, in Wright et al. (1992, Critical Rev. Immunol. 12:125-168), and the references cited therein. Further, the antibody of the invention may be "humanized" using the technology described in, for example, Wright et al., and in the references cited therein, and in Gu et al. (1997, Thrombosis and Hematocyst 77:755-759), and other methods of humanizing antibodies well-known in the art or to be developed.

The present invention also includes the use of humanized antibodies specifically reactive with epitopes of an antigen of interest. The humanized antibodies of the invention have a human framework and have one or more complementarity determining regions (CDRs) from an antibody, typically a mouse antibody, specifically reactive with an antigen of interest. When the antibody used in the invention is humanized, the antibody may be generated as described in Queen, et al. (U.S. Pat. No. 6,180,370), Wright et al., (supra) and in the references cited therein, or in Gu et al. (1997, Thrombosis and Hematocyst 77(4):755-759). The method disclosed in Queen et al. is directed in part toward designing humanized immunoglobulins that are produced by expressing recombinant DNA segments encoding the heavy and light chain complementarity determining regions (CDRs) from a donor immunoglobulin capable of binding to a desired antigen, such as an epitope on an antigen of interest, attached to DNA segments encoding acceptor human framework regions. Generally speaking, the invention in the Queen patent has applicability toward the design of substantially any humanized immunoglobulin. Queen explains that the DNA segments will typically include an expression control DNA sequence operably linked to the humanized immunoglobulin coding sequences, including naturally-associated or heterologous promoter regions. The expression control sequences can be eukaryotic promoter systems in vectors capable of transforming or transfecting eukaryotic host cells or the expression control sequences can be prokaryotic promoter systems in vectors capable of transforming or transfecting prokaryotic host cells. Once the vector has been incorporated into the appropriate host, the host is maintained under conditions suitable for high level expression of the introduced nucleotide sequences and as desired the collection and purification of the humanized light chains, heavy chains, light/heavy chain dimers or intact antibodies, binding fragments or other immunoglobulin forms may follow (Beychok, Cells of Immunoglobulin Synthesis, Academic Press, New York, (1979), which is incorporated herein by reference).

One of skill in the art will further appreciate that the present invention encompasses the use of antibodies derived from camelid species. That is, the present invention includes, but is not limited to, the use of antibodies derived from species of the camelid family. As is well known in the art, camelid antibodies differ from those of most other mammals in that they lack a light chain, and thus comprise only heavy chains with complete and diverse antigen binding capabilities (Hamers-Casterman et al., 1993, Nature, 363:446-448). Such heavy-chain antibodies are useful in that they are smaller than conventional mammalian antibodies, they are more soluble than conventional antibodies, and further demonstrate an increased stability compared to some other antibodies.

Camelid species include, but are not limited to Old World camelids, such as two-humped camels (*C. bactrianus*) and one humped camels (*C. dromedarius*). The camelid family further comprises New World camelids including, but not limited to llamas, alpacas, vicuna and guanaco. The use of Old World and New World camelids for the production of antibodies is contemplated in the present invention, as are other methods for the production of camelid antibodies set forth herein.

The production of polyclonal sera from camelid species is substantively similar to the production of polyclonal sera from other animals such as sheep, donkeys, goats, horses, mice, chickens, rats, and the like. The skilled artisan, when equipped with the present disclosure and the methods detailed herein, can prepare high-titers of antibodies from a camelid species. As an example, the production of antibodies in mammals is detailed in such references as Harlow et al., (1989, Antibodies: A Laboratory Manual, Cold Spring Harbor, N.Y.). Camelid species for the production of antibodies and sundry other uses are available from various sources, including but not limited to, Camello Fataga S. L. (Gran Canaria, Canary Islands) for Old World camelids, and High Acres Llamas (Fredricksburg, Tex.) for New World camelids.

The isolation of camelid antibodies from the serum of a camelid species can be performed by many methods well known in the art, including but not limited to ammonium sulfate precipitation, antigen affinity purification, Protein A and Protein G purification, and the like. As an example, a camelid species may be immunized to a desired antigen, for example, an epitope of an antigen of the invention, or fragment thereof, using techniques well known in the art. The whole blood can them be drawn from the camelid and sera can be separated using standard techniques. The sera can then be absorbed onto a Protein G-Sepharose column (Pharmacia, Piscataway, N.J.) and washed with appropriate buffers, for example 20 mM phosphate buffer (pH 7.0). The camelid antibody can then be eluted using a variety of techniques well known in the art, for example 0.15M NaCl, 0.58% acetic acid (pH 3.5). The efficiency of the elution and purification of the camelid antibody can be determined by various methods, including SDS-PAGE, Bradford Assays, and the like. The fraction that is not absorbed can be bound to a Protein A-Sepharose column (Pharmacia, Piscataway, N.J.) and eluted using, for example, 0.15M NaCl, 0.58% acetic acid (pH 4.5). The skilled artisan will readily understand that the above methods for the isolation and purification of camelid antibodies are exemplary, and other methods for protein isolation are well known in the art and are encompassed in the present invention.

The present invention further contemplates the production of camelid antibodies expressed from nucleic acid. Such methods are well known in the art, and are detailed in, for example U.S. Pat. Nos. 5,800,988; 5,759,808; 5,840,526, and 6,015,695, which are incorporated herein by reference in their entirety. Briefly, cDNA can be synthesized from camelid spleen mRNA. Isolation of RNA can be performed using multiple methods and compositions, including TRIZOL (Gibco/BRL, La Jolla, Calif.) further, total RNA can be isolated from tissues using the guanidium isothiocyanate method detailed in, for example, Sambrook et al. (2001, Molecular Cloning, A Laboratory Manual, Cold Spring Harbor, N.Y.). Methods for purification of mRNA from total cellular or tissue RNA are well known in the art, and include, for example, oligo-T paramagnetic beads. cDNA synthesis can then be obtained from mRNA using mRNA template, an oligo dT primer and a reverse transcriptase enzyme, available commercially from a variety of sources, including Invitrogen (La Jolla, Calif.). Second strand cDNA can be obtained from mRNA using RNAse H and E. coli DNA polymerase I according to techniques well known in the art.

Identification of cDNA sequences of relevance can be performed by hybridization techniques well known by one of ordinary skill in the art, and include methods such as Southern blotting, RNA protection assays, and the like. Probes to identify variable heavy immunoglobulin chains ($V_{HH}$) are available commercially and are well known in the art, as detailed in, for example, Sastry et al., (1989, Proc. Nat'l. Acad. Sci. USA, 86:5728). Full-length clones can be produced from cDNA sequences using any techniques well known in the art and detailed in, for example, Sambrook et al. (2001, Molecular Cloning, A Laboratory Manual, Cold Spring Harbor, N.Y.).

The clones can be expressed in any type of expression vector known to the skilled artisan. Further, various expression systems can be used to express the $V_{HH}$ peptides of the present invention, and include, but are not limited to eukaryotic and prokaryotic systems, including bacterial cells, mammalian cells, insect cells, yeast cells, and the like. Such methods for the expression of a protein are well known in the art and are detailed elsewhere herein.

The $V_{HH}$ immunoglobulin proteins isolated from a camelid species or expressed from nucleic acids encoding such proteins can be used directly in the methods of the present invention, or can be further isolated and/or purified using methods disclosed elsewhere herein.

The present invention is not limited to $V_{HH}$ proteins isolated from camelid species, but also includes $V_{HH}$ proteins isolated from other sources such as animals with heavy chain disease (Seligmann et al., 1979, Immunological Rev. 48:145-167, incorporated herein by reference in its entirety). The present invention further comprises variable heavy chain immunoglobulins produced from mice and other mammals, as detailed in Ward et al. (1989, Nature 341:544-546, incorporated herein by reference in its entirety). Briefly, $V_H$ genes were isolated from mouse splenic preparations and expressed in E. coli. The present invention encompasses the use of such heavy chain immunoglobulins in the treatment of various autoimmune disorders detailed herein.

As used herein, the term "heavy chain antibody" or "heavy chain antibodies" comprises immunoglobulin molecules derived from camelid species, either by immunization with an peptide and subsequent isolation of sera, or by the cloning and expression of nucleic acid sequences encoding such antibodies. The term "heavy chain antibody" or "heavy chain antibodies" further encompasses immunoglobulin molecules isolated from an animal with heavy chain disease, or prepared by the cloning and expression of $V_H$ (variable heavy chain immunoglobulin) genes from an animal.

Once expressed, whole antibodies, dimers derived therefrom, individual light and heavy chains, or other forms of antibodies can be purified according to standard procedures known in the art.

In one embodiment of the invention, a phage antibody library may be generated, as described in detail elsewhere herein. To generate a phage antibody library, a cDNA library is first obtained from mRNA which is isolated from cells, e.g., peripheral blood lymphocytes, which express the desired protein to be expressed on the phage surface, e.g., the desired antibody. cDNA copies of the mRNA are produced using reverse transcriptase. cDNA which specifies immunoglobulin fragments are obtained by PCR and the resulting DNA is cloned into a suitable bacteriophage vector to generate a bacteriophage DNA library comprising DNA specifying immunoglobulin genes. The procedures for making a bacteriophage library comprising heterologous DNA are well known in the art and are described, for example, in Sambrook et al., supra.

Bacteriophage which encode the desired antibody, may be engineered such that the protein is displayed on the surface thereof in such a manner that it is available for binding to its corresponding binding protein, e.g., the antigen against which the antibody is directed, such as an antigen of interest. Thus, when bacteriophage which express a specific antibody are incubated in the presence of the corresponding antigen, the bacteriophage will bind to the antigen. Bacteriophage which do not express the antibody will not bind to the antigen. Such panning techniques are well known in the art and are described for example, in Wright et al. (supra).

Processes such as those described above, have been developed for the production of human antibodies using M13 bacteriophage display (Burton et al., 1994, Adv. Immunol. 57:191-280). Essentially, a cDNA library is generated from mRNA obtained from a population of antibody-producing cells. The mRNA encodes rearranged immunoglobulin genes and thus, the cDNA encodes the same. Amplified cDNA is cloned into M13 expression vectors creating a library of phage which express human Fab fragments on their surface. Phage which display the antibody of interest are selected by antigen binding and are propagated in bacteria to produce soluble human Fab immunoglobulin. Thus, in contrast to conventional monoclonal antibody synthesis, this procedure immortalizes DNA encoding human immunoglobulin rather than cells which express human immunoglobulin.

The procedures just presented describe the generation of phage which encode the Fab portion of an antibody molecule. However, the invention should not be construed to be limited solely to the generation of phage encoding Fab antibodies. Rather, phage which encode single chain antibodies (scFv/phage antibody libraries) are also included in the invention. Fab molecules comprise the entire Ig light chain, that is, they comprise both the variable and constant region of the light chain, but include only the variable region and first constant region domain (CH1) of the heavy chain. Single chain antibody molecules comprise a single chain of protein comprising the Ig Fv fragment. An Ig Fv fragment includes only the variable regions of the heavy and light chains of the antibody, having no constant region contained therein. Phage libraries comprising scFv DNA may be generated following the procedures described in Marks et al. (1991, J. Mol. Biol. 222: 581-597). Panning of phage so generated for the isolation of a desired antibody is conducted in a manner similar to that described for phage libraries comprising Fab DNA.

The invention should also be construed to include synthetic phage display libraries in which the heavy and light chain variable regions may be synthesized such that they include nearly all possible specificities (Barbas, 1995, Nature Medicine 1:837-839; de Kruif et al. 1995, J. Mol. Biol. 248:97-105).

In another embodiment of the invention, phage-cloned antibodies derived from immunized animals can be humanized by known techniques.

Chimeric Molecule Production

Following the isolation of a desirable antibody or antigen-binding region thereof, the antibody or fragment thereof can be fused with a protein to generate a chimeric molecule comprising a targeting moiety and a therapeutic peptide (e.g., a cytotoxic moiety, an apoptosis-inducing moiety, laser absorbing moiety, and the like). The chimeric molecule of the present invention may be produced in any suitable manner available in the art, although in particular embodiments, the chimeric molecule is generated as a fusion polypeptide or is chemically conjugated, such as by use of a linker.

A. Chimeric Chemical Conjugates/Chimeric Conjugates with Linkers

In embodiments wherein the chimeric molecule is produced by conjugation, such as chemical conjugation or by use of a linker, the singular components are provided or obtained and are then associated by a chemical conjugation or linking method.

For example, the chimeric molecule components may be joined via a biologically-releasable bond, such as a selectively-cleavable linker or amino acid sequence. For example, peptide linkers that include a cleavage site for an enzyme preferentially located or active within a tumor environment are contemplated. Exemplary forms of such peptide linkers are those that are cleaved by urokinase, plasmin, thrombin, Factor IXa, Factor Xa, or a metallaproteinase, such as collagenase, gelatinase, or stromelysin. Alternatively, peptides or polypeptides may be joined to an adjuvant.

Additionally, any other linking/coupling agents and/or mechanisms known to those of skill in the art can be used to combine the components of the present invention, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

It is contemplated that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is 4-succinimdyloxycarbonyl-methyl-x-[2-pyridyldithio]-toluene (SMPT), which is a bifunctional cross-linker containing a disulfide bond that is "sterically hindered" by an adjacent benzene ring and methyl groups. It is believed that steric hindrance of the disulfide bond serves the function of protecting the bond from attack by thiolate anions such as glutathione which can be present in tissues and blood, and thereby aids in preventing decoupling of the conjugate prior to the delivery of the attached agent to the target site.

The SMPT cross-linking reagent, as with many other known cross-linking reagents, facilitates cross-linking of functional groups such as the SH of cysteine or primary amines (e.g., the epsilon amino group of lysine). Another type of cross-linker includes the hetero-bifunctional photoreactive phenylazides containing a cleavable disulfide bond such as sulfosuccinimidyl-2-(p-azido salicylamido)ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include succinimidyl acetylthioacetate (SATA), N-succinimidyl3-(2-pyridyldithio) propionate SPDP and 2-iminothiolane (Wawrzynczak & Thorpe, 1987). The use of such cross-linkers is well understood in the art.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Preferred uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

Another embodiment involves the use of flexible linkers.

B. Chimeric Fusion Molecules

In embodiments wherein the chimeric molecule comprises a fusion protein, a polynucleotide that encodes a chimeric protein, mutant polypeptide, biologically active fragment of chimeric protein, or functional equivalent thereof, may be used to generate recombinant DNA molecules that direct the expression of the chimeric protein, chimeric peptide fragments, or a functional equivalent thereof, in appropriate host cells.

Due to the inherent degeneracy of the genetic code, other DNA sequences that encode substantially the same or a functionally equivalent amino acid sequence, may be used in the practice of the invention of the cloning and expression of the chimeric protein. Such DNA sequences include those capable of hybridizing to the chimeric sequences or their complementary sequences under stringent conditions.

In one embodiment, the phrase "stringent conditions" as used herein refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with a 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS.

Altered DNA sequences that may be used in accordance with the invention include deletions, additions or substitutions of different nucleotide residues resulting in a sequence that encodes the same or a functionally equivalent fusion gene product. The gene product itself may contain deletions, additions or substitutions of amino acid residues within a chimeric sequence, which result in a silent change thus producing a functionally equivalent chimeric protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The DNA sequences of the invention may be engineered in order to alter a chimeric coding sequence for a variety of ends, including but not limited to, alterations that modify'processing and expression of the gene product. For example, mutations may be introduced using techniques which are well known in the art, e.g., site-directed mutagenesis, to insert new restriction sites, to alter glycosylation patterns, phosphorylation, etc.

In an alternate embodiment of the invention, the coding sequence of the chimeric protein could be synthesized in whole or in part, using chemical methods well known in the art. (See, for example, Matteucci and Caruthers et al., 1980 Tetrahedron Letter 21: 719; Crea and Horn, 1980 Nucleic Acids Res. 8: 2331-2348; Chow and Kempe, 1981 Nuc. Acids Res. 9: 2807-2817). For example, active domains of the moieties can be synthesized by solid phase techniques, cleaved from the resin, and purified by preparative high performance liquid chromatography followed by chemical linkage to form a chimeric protein. (e.g., see Creighton, 1983, Proteins Structures And Molecular Principles, W.H. Freeman and Co., N.Y. pp. 50-60). The composition of the synthetic peptides may be confirmed by amino acid analysis or sequencing (e.g., the Edman degradation procedure; see Creighton, 1983, Proteins, Structures and Molecular Principles, W.H. Freeman and Co., N.Y. pp. 34-49). Alternatively, the two moieties of the chimeric protein produced by synthetic or recombinant methods may be conjugated by chemical linkers according to methods well known in the art (Brinkmann and Pastan, 1994 Biochem. Biophys. Acta. 1198: 27-45).

In order to express a biologically active chimeric protein, the nucleotide sequence encoding for a chimeric protein, or a functional equivalent, is inserted into an appropriate expression vector, i.e., a vector which contains the necessary elements for the transcription and translation of the inserted coding sequence. The chimeric gene products as well as host cells or cell lines transfected or transformed with recombinant chimeric expression vectors can be used for a variety of purposes. These include but are not limited to generating antibodies (i.e., monoclonal or polyclonal) that bind to epitopes of the proteins to facilitate their purification.

Methods that are well known to those skilled in the art can be used to construct expression vectors containing the chimeric protein coding sequence and appropriate transcriptional/translational control signals. These methods include in vitro recombinant DNA techniques, synthetic techniques and in vivo recombination/genetic recombination. See, for example, the techniques described in Sambrook et al., 2001, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the chimeric protein coding sequence. These include but are not limited to microorganisms such as bacteria transformed with recombinant bacteriophage DNA, plasmid DNA or cosmid DNA expression vectors containing the chimeric protein coding sequence; yeast transformed with recombinant yeast expression vectors containing the chimeric protein coding sequence; insect cell systems infected with recombinant virus expression vectors (e.g., baculovirus) containing the chimeric protein coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the chimeric protein coding sequence; or animal cell systems. It should be noted that since most apoptosis-inducing proteins cause programmed cell death in mammalian cells, it is preferred that the chimeric protein of the invention be expressed in prokaryotic or lower eukaryotic cells.

The expression elements of each system vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage lambda, plac, ptrp, ptac (ptrp-lac hybrid promoter; cytomegalovirus promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll alpha/beta binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the chimeric DNA, SV40-, BPV- and EBV-based vectors may be used with an appropriate selectable marker.

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. The presence of consensus N-glycosylation sites in a chimeric protein may require proper modification for optimal chimeric protein function. Different host cells have characteristic and specific mechanisms for the post-translational processing and modification of proteins. Appropriate cell lines or host systems can be chosen to ensure the correct modification and processing of the chimeric protein. To this end, eukaryotic host cells that possess the cellular machinery for proper processing of the primary transcript, glycosylation, and phosphorylation of the chimeric protein may be used. Such mammalian host cells include but are not limited to CHO, VERO, BHK, HeLa, COS, MDCK, 293, W138, and the like.

Therapeutic Moiety

In some aspects of the present invention, the antibody can be engineered to comprise an anti-tumor agent including but not limited to a chemotherapeutic agent, an anti-cell proliferation agent or any combination thereof. The chimeric antibody comprising an anti-tumor agent may act additively or synergistically against the cancer. The term "synergistically" as used herein refers to the combined effect of the antibody and anti-tumor agent being greater than the sum of their individual effects.

The invention should not limited to any particular chemotherapeutic agent. Rather, any chemotherapeutic agent can be linked to the antibodies of the invention. For example, any conventional chemotherapeutic agents of the following non-limiting exemplary classes are included in the invention: alkylating agents; nitrosoureas; antimetabolites; antitumor antibiotics; plant alkyloids; taxanes; hormonal agents; and miscellaneous agents.

Alkylating agents are so named because of their ability to add alkyl groups to many electronegative groups under conditions present in cells, thereby interfering with DNA replication to prevent cancer cells from reproducing. Most alkylating agents are cell cycle non-specific. In specific aspects, they stop tumor growth by cross-linking guanine bases in DNA double-helix strands. Non-limiting examples include busulfan, carboplatin, chlorambucil, cisplatin, cyclophosphamide, dacarbazine, ifosfamide, mechlorethamine hydrochloride, melphalan, procarbazine, thiotepa, and uracil mustard.

Anti-metabolites prevent incorporation of bases into DNA during the synthesis (S) phase of the cell cycle, prohibiting normal development and division. Non-limiting examples of antimetabolites include drugs such as 5-fluorouracil, 6-mercaptopurine, capecitabine, cytosine arabinoside, floxuridine, fludarabine, gemcitabine, methotrexate, and thioguanine.

There are a variety of antitumor antibiotics that generally prevent cell division by interfering with enzymes needed for cell division or by altering the membranes that surround cells. Included in this class are the anthracyclines, such as doxorubicin, which act to prevent cell division by disrupting the structure of the DNA and terminate its function. These agents are cell cycle non-specific. Non-limiting examples of antitumor antibiotics include dactinomycin, daunorubicin, doxorubicin, idarubicin, mitomycin-C, and mitoxantrone.

Plant alkaloids inhibit or stop mitosis or inhibit enzymes that prevent cells from making proteins needed for cell growth. Frequently used plant alkaloids include vinblastine, vincristine, vindesine, and vinorelbine. However, the invention should not be construed as being limited solely to these plant alkaloids.

The taxanes affect cell structures called microtubules that are important in cellular functions. In normal cell growth, microtubules are formed when a cell starts dividing, but once the cell stops dividing, the microtubules are disassembled or destroyed. Taxanes prohibit the microtubules from breaking down such that the cancer cells become so clogged with microtubules that they cannot grow and divide. Non-limiting exemplary taxanes include paclitaxel and docetaxel.

Hormonal agents and hormone-like drugs are utilized for certain types of cancer, including, for example, leukemia, lymphoma, and multiple myeloma. They are often employed with other types of chemotherapy drugs to enhance their effectiveness. Sex hormones are used to alter the action or production of female or male hormones and are used to slow the growth of breast, prostate, and endometrial cancers. Inhibiting the production (aromatase inhibitors) or action (tamoxifen) of these hormones can often be used as an adjunct to therapy. Some other tumors are also hormone dependent. Tamoxifen is a non-limiting example of a hormonal agent that interferes with the activity of estrogen, which promotes the growth of breast cancer cells.

Miscellaneous agents include chemotherapeutics such as bleomycin, hydroxyurea, L-asparaginase, and procarbazine that are also useful in the invention.

An anti-cell proliferation agent can further be defined as an apoptosis-inducing agent or a cytotoxic agent. The apoptosis-inducing agent may be a granzyme, a Bcl-2 family member, cytochrome C, a caspase, or a combination thereof. Exemplary granzymes include granzyme A, granzyme B, granzyme C, granzyme D, granzyme E, granzyme F, granzyme G, granzyme H, granzyme I, granzyme J, granzyme K, granzyme L, granzyme M, granzyme N, or a combination thereof. In other specific aspects, the Bcl-2 family member is, for example, Bax, Bak, Bcl-Xs, Bad, Bid, Bik, Hrk, Bok, or a combination thereof.

In additional aspects, the caspase is caspase-1, caspase-2, caspase-3, caspase-4, caspase-5, caspase-6, caspase-7, caspase-8, caspase-9, caspase-10, caspase-11, caspase-12, caspase-13, caspase-14, or a combination thereof. In specific aspects, the cytotoxic agent is TNF-α, gelonin, Prodigiosin, a ribosome-inhibiting protein (RIP), *Pseudomonas exotoxin*, *Clostridium difficile* Toxin 13, *Helicobacter pylori* VacA, *Yersinia enterocolitica* YopT, Violacein, diethylenetriamine-pentaacetic acid, irofulven, Diptheria Toxin, mitogillin, ricin, botulinum toxin, cholera toxin, saporin 6, or a combination thereof.

Labeling of Antibodies.

The antibodies of the invention can be fused to a labeling agent for the detection of the antibody or chimeric molecule. Detection proceeds by any known method, including immunoblotting, western analysis, gel-mobility shift assays, tracking of radioactive or bioluminescent markers, nuclear magnetic resonance, electron paramagnetic resonance, stopped-flow spectroscopy, column chromatography, capillary electrophoresis, or other methods which track a molecule based upon an alteration in size and/or charge. The particular label or detectable group used in the assay is not a critical aspect of the invention. The detectable group can be any material having a detectable physical or chemical property. Such detectable labels have been well-developed in the field of immunoassays and, in general, any label useful in such methods can be applied to the present invention. Thus, a label is any composition detectable by spectroscopic, photochemical, biochemical, immunochemical, electrical, optical or chemical means. Useful labels in the present invention include magnetic beads (e.g. Dynabeads™.), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., LacZ, CAT, horse radish peroxidase, alkaline phosphatase and others, commonly used as detectable enzymes, either as marker gene products or in an ELISA), and colorimetric labels such as colloidal gold or colored glass or plastic (e.g. polystyrene, polypropylene, latex, etc.) beads.

The label may be coupled directly or indirectly to the desired component of the assay according to methods well known in the art. As indicated above, a wide variety of labels may be used, with the choice of label depending on the sensitivity required, ease of conjugation of the compound, stability requirements, available instrumentation, and disposal provisions.

The molecules can also be conjugated directly to signal generating compounds, e.g., by conjugation with an enzyme or fluorophore. Enzymes of interest as labels include hydrolases, particularly phosphatases, esterases and glycosidases, or oxidoreductases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems which may be used, see, U.S. Pat. No. 4,391,904, which is incorporated herein by reference.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence, e.g., by microscopy, visual inspection, via photographic film, by the use of electronic detectors such as charge coupled devices (CCDs) or photomultipliers and the like. Similarly, enzymatic labels may be detected by providing appropriate substrates for the enzyme and detecting the resulting reaction product. Finally, simple colorimetric labels may be detected simply by observing the color associated with the label.

Administration of the Chimeric Molecules

In some embodiments, an effective amount of the chimeric molecule of the present invention is administered to a cell. In other embodiments, a therapeutically effective amount of the chimeric molecules of the present invention are administered to an individual for the treatment of disease.

The term "effective amount" as used herein is defined as the amount of the chimeric molecules of the present invention that is necessary to result in a physiological change in the cell or tissue to which it is administered.

The term "therapeutically effective amount" as used herein is defined as the amount of the chimeric molecules of the present invention that eliminates, decreases, delays, or minimizes adverse effects of a disease, such as cancer. A skilled artisan readily recognizes that in many cases the chimeric molecules may not provide a cure but may only provide partial benefit, such as alleviation or improvement of at least one symptom of the disease. In some embodiments, a physiological change having some benefit is also considered therapeutically beneficial. Thus, in some embodiments, an amount of chimeric molecules that provides a physiological change is considered an "effective amount" or a "therapeutically effective amount."

In some embodiments of the present invention and as an advantage over known methods in the art, the chimeric molecules are delivered as proteins and not as nucleic acid molecules to be translated to produce the desired polypeptides. As an additional advantage, in some embodiments human sequences are utilized in the chimeric polypeptides of the present invention to circumvent any undesirable immune responses from a foreign polypeptide.

The chimeric proteins of the invention may be administered to a subject per se or in the form of a pharmaceutical composition for the treatment of cancer, autoimmunity, transplantation rejection, post-traumatic immune responses and infectious diseases, for example by targeting viral antigens, such as gp120 of HIV. More specifically, the chimeric polypeptides may be useful in eliminating cells involved in immune cell-mediated disorder, including lymphoma; autoimmunity, transplantation rejection, graft-versus-host disease, ischemia and stroke. Pharmaceutical compositions comprising the proteins of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries that facilitate processing of the proteins into preparations which can be used pharmaceutically. Proper formulation is dependent upon the route of administration chosen.

For topical administration the proteins of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, inhalation, oral or pulmonary administration.

For injection, the proteins of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents.

Alternatively, the proteins may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the proteins can be readily formulated by combining the proteins with pharmaceutically acceptable carriers well known in the art. Such carriers enable the proteins of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

Alternatively, other pharmaceutical delivery systems may be employed. Liposomes and emulsions are well-known examples of delivery vehicles that may be used to deliver proteins of the invention. Certain organic solvents such as dimethylsulfoxide also may be employed, although usually at the cost of greater toxicity. Additionally, the molecules may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the molecules for a few weeks up to over 100 days. Depending on the chemical nature and the biological stability of the chimeric molecules, additional strategies for molecule stabilization may be employed.

The protein embodiments of the chimeric molecules of the invention may contain charged side chains or termini. Thus, they may be included in any of the above-described formulations as the free acids or bases or as pharmaceutically acceptable salts. Pharmaceutically acceptable salts are those salts that substantially retain the biologic activity of the free bases and which are prepared by reaction with inorganic acids. Pharmaceutical salts tend to be more soluble in aqueous and other protic solvents than are the corresponding free base forms.

The chimeric molecules of the invention will generally be used in an amount effective to achieve the intended purpose. For use to treat or prevent a disease condition, the molecules of the invention, or pharmaceutical compositions thereof, are administered or applied in a therapeutically effective amount.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the molecules which are sufficient to maintain therapeutic effect. Usual patient dosages for administration by injection range from about 0.001 to 100 mg/kg/day, preferably from about 0.5 to 1 mg/kg/day and any and all whole or partial integers there between. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of molecules administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Materials and Methods

Phage display Library construction.

All human and animal studies were approved by the Institutional Review Board of the University of Pennsylvania. Using previously described methods (protocol 9.2, Barbas, C. F. I., Burton, D. R., Scott, J. K., and Silverman, G. J. 2001. Phage display: a laboratory manual. Cold Spring Harbor Laboratory Press. Cold Spring Harbor, N.Y., USA.), separate IgGκ and IgGλ phage libraries were constructed using the phagemid vector pComb3X (Scripps Research Institute) from $4 \times 10^7$ mononuclear cells isolated from 25 ml of peripheral blood from a patient with active acute mucocutaneous PV. The phagemid library was electroporated into the XL1-Blue suppressor strain of E. coli (Stratagene) together with VCSM13 helper phages (Stratagene). Recombinant phages were purified from culture supernatants by polyethylene glycol precipitation and resuspended in PBS, pH 7.4, containing 1% BSA. The diversity of the unselected library was evaluated by sequencing of 42 randomly selected clones to determine the usage of $V_H$ and $V_L$ gene segments. Recombinant phagemids were purified with a plasmid preparation system (QIAGEN Inc.), and the $V_H$ and $V_L$ inserts were sequenced using pComb3X-specific primers previously described (protocol 11.24, Barbas, C. F. I., Burton, D. R., Scott, J. K., and Silverman, G. J. 2001. Phage display: a laboratory manual. Cold Spring Harbor Laboratory Press. Cold Spring Harbor, N.Y., USA.). Sequences were analyzed for homology to known human V, D, and J genes using the V BASE database (http://vbase.mrc-cpe.cam.ac.uk. Medical Research Council Centre for Protein Engineering, University of Cambridge, Cambridge, United Kingdom).

Library Selection.

IgGκ and IgGλ antibody phage display libraries were combined in equal amounts and panned by solid-phase selection on ELISA plates coated with Dsg3 or Dsg1 (RhiGene Inc.). Briefly, freshly amplified phage library (approximately $1 \times 10^{11}$ to $5 \times 10^{11}$ phages) was incubated for 2 hours at 37° C. on ELISA plate wells in PBS plus 2 mM CaCl2. After washing of wells with 0.1% (vol/vol) Tween-20 in PBS plus calcium, adherent phages were eluted with 78 mM citrate buffer, pH 2.4. After neutralization with 2 M Tris, pH 7.4, eluted phages were used to transform a fresh culture of XL1-Blue E. coli, which was amplified overnight as previously described (Siegel et al., 1997 J. Immunol. Methods. 206:73-85). Phages were harvested from culture supernatants and then repanned against desmoglein substrate for 3 subsequent rounds as described for the original library. Individual phage clones were isolated from each round of panning, and binding to Dsg1 and Dsg3 was confirmed by ELISA using HRP-conjugated anti-M13 antibody as the developing reagent (Roche Diagnostics Corp.). The heavy and light chain variable-region nucleic acid sequences were determined for positive clones in order to establish the cohort of unique anti-Dsg-specific mAbs.

Production of Soluble scFvs.

In order to produce scFv monoclonal preparations unlinked to phages, the TOP10F' nonsuppressor strain of *E. coli* (Invitrogen Corp.) was infected with an individual phage clone (protocol 11.6, Barbas, C. F. I., Burton, D. R., Scott, J. K., and Silverman, G. J. 2001. Phage display: a laboratory manual. Cold Spring Harbor Laboratory Press. Cold Spring Harbor, N.Y., USA). Soluble scFv molecules were then purified from the bacterial periplasmic space using sucrose shock and nickel-chelation affinity chromatography as previously described (Chang et al., 1998, Blood, 91:3066-3078.). ScFvs were dialyzed against PBS and concentrated by Amicon ultrafiltration (Millipore Corp.) for some experiments. Various preparations of scFvs were normalized for approximate scFv concentrations by SDS-PAGE at different dilutions followed by immunoblotting with HRP-conjugated anti-HA antibodies (Roche Diagnostics Corp.).

Gel-Filtration HPLC.

Size exclusion chromatography was performed on a 30-cm×8-mm G2000SW TSK-GEL column (Tosoh Bioscience LLC) equilibrated with 0.15 M NaCl, 0.01 M Mops, pH 6.8. Bovine transferrin (75 kDa; Sigma-Aldrich) and bovine erythrocyte carbonic anhydrase (30 kDa; Sigma-Aldrich), 50 µg/ml in equilibration buffer, served as protein standards. 0.1 M Mops solution was added to all solutions as a marker of the total volume of the column. Approximately 5 µg of scFvs (200 µg/ml in PBS, pH 7.4) was injected into the column, eluted at 0.5 ml/min, and detected by OD230 nm absorbance using a PerkinElmer Inc. LC235 diode array detector. Data were analyzed with IGOR Pro software (WaveMetrics).

ELISA Binding and Inhibition Studies.

ScFv preparations were diluted in sample diluent (RhiGene Inc.) and incubated on Dsg3 and Dsg1 ELISA plates according to the manufacturer's directions for use with human sera. After washing, plates were developed with HRP-conjugated anti-HA antibody (Roche Diagnostics Corp.) and tetramethylbenzidine substrate. Absorbance was read at 450 nm. Irrelevant scFvs (E1M2, a human anti-red blood cell antibody [Chang and Siegel, 1998. Blood. 91:3066-3078] and AM3-13 [D. L. Siegel, unpublished observations]) were used at similar concentrations as negative controls. For some experiments, ELISA plate wells coated with the BP180 antigen substrate (RhiGene Inc.) were also used as negative controls. Inhibition ELISA was performed by incubation of pemphigus or normal control sera (1:6.25 to 1:25) with scFvs on desmoglein ELISA plates. ScFvs were used at dilutions that result in OD readings (in the absence of putative blocking serum) of approximately 0.4 to 2.0 (linear range in plot of OD versus negative log of dilution). Inhibition was calculated according to the following formula: Equation 1;

$$\% \text{ Inhibition} = (1-(OD_{S/B}-OD_{Sc/B})/(OD_{S/Bc}-OD_{Sc/Bc})) \times 100$$

where S is the scFv being tested, Sc is scFv negative control, B is blocking pemphigus serum, and Bc is normal human serum.

Direct and Indirect Immunofluorescence.

Immunofluorescence using scFvs was performed on mouse tail, neonatal mouse skin, and human skin as previously described (Wu, H., et al., 2000, N. Engl. J. Med. 343: 31-35; Mahoney et al., 1999, J. Clin. Invest, 103:461-468; Amagai et al., 2000, Nat. Med. 6:1275-127751; Hanakawa et al., 2003, J. Invest. Dermatol. 121:383-389) except for the detecting reagent, which comprised rat monoclonal anti-HA antibody (3F10; Roche Diagnostics Corp.) followed by Alexa Fluor 568—conjugated anti-rat IgG (Invitrogen Corp.).

Immunoblotting.

Primary human keratinocytes were cultured in defined keratinocyte-serum-free media (keratinocyte-SFM; Invitrogen Corp.) supplemented with 1.2 mM calcium chloride for 24 hours before harvesting. Cells were lysed with Laemmli sample buffer, and extracts were separated on denaturing SDS-PAGE and either stained with Coomassie reagent or transferred to nitrocellulose. Membranes were incubated with human scFvs or murine anti-Dsg3 mAb 5G11 (Zymed Laboratories Inc.) or anti-Dsg1 mAb P124 (Research Diagnostics Inc.) diluted in PBS/5% milk. Blots were washed with PBS containing 0.1% (wt/vol) Tween-20 and then incubated with either HRP-conjugated anti-HA antibodies or HRP-conjugated goat antimouse antibodies (Bio-Rad Laboratories) diluted in PBS/5% milk. Blots were developed using ECL Plus reagent (Amersham Biosciences Corp.).

Neonatal Mouse Injection.

Injection of scFvs into neonatal mice was performed as previously described (Wu et al., 2000, N. Engl. J. Med. 343: 31-35; Mahoney et al., 1999, J. Clin. Invest. 103:461-468; Amagai et al., 1992, J. Clin. Invest. 90:919-926). In some experiments, ETA was also injected into neonatal mice to cleave Dsg1 to determine whether anti-Dsg3 scFvs were pathogenic (Tsunoda et al., 2003, J. Immunol. 170:2170-2178). Recombinant ETA with a 6×-histidine tag was produced and purified on Ni-NTA columns (QIAGEN Inc.) as previously described (Hanakawa et al., 2002, J. Clin. Invest., 110:53-60). In preliminary experiments, neonatal mice were injected with various doses (0.5-10 µg) of ETA to determine a dose that did not cause blistering alone (approximately 1 µg). ScFvs (approximately 20-100 µg) diluted in PBS were injected s.c. along the back into 1- to 2-day-old neonatal C57BL/6J mice weighing 1.2-1.8 g, with or without concomitant injection of ETA. Mice were sacrificed at 6-8 hours, 10 minutes after another injection with 25 units of heparin (Sigma-Aldrich). Skin was harvested for direct immunofluorescence by freezing in OCT (Electron Microscopy Sciences), and for histology by fixation in 10% PBS-buffered formalin (Sigma-Aldrich). Blood was collected, and the plasma was used for BF on normal mouse tail to determine the titer of circulating scFvs for each injection.

Epitope Mapping of scFvs Against Domain-Swapped Mouse Desmoglein Produced in Baculovirus.

Domain-swapped desmoglein molecules comprising the extracellular domain of Dsg1 and Dsg3 were produced in baculovirus as previously described (Futei, Y., et al., 2000, J. Invest. Dermatol., 115:829-834). ScFvs were incubated with 300 µl of baculovirus culture supernatant containing the recombinant proteins for 30 minutes at room temperature. The proteins were immunoprecipitated with anti-HA agarose (Sigma-Aldrich) at 4° C. overnight and separated by SDS-PAGE. After transfer to polyvinyl difluoride membrane (Millipore Corp.), immunoblots were probed with antibody against E tag (Amersham Biosciences Corp.), which was engineered at the carboxy terminus of all recombinant desmoglein molecules.

Dispase Assay of Cultured Keratinocytes.

Primary human keratinocytes were seeded onto 12-well plates in defined keratinocyte-SFM (Invitrogen Corp.) containing less than 0.1 mM calcium. After reaching confluence, cells were incubated for 6 hours with scFvs at varying dilutions in defined keratinocyte-SFM supplemented with 0.4 mM calcium chloride. For scFvs reactive to Dsg3 only, cells were also incubated with 0.5 µg/ml exfoliative toxin for the last 2 hours to inactivate Dsg1. Cultures were washed twice with PBS and then incubated with 1.2 units of dispase (Roche Diagnostics Corp.) for 30 minutes at 37° C. Released monolayers were washed twice with PBS and gently pipetted through a 1-ml pipette tip 5 times to mechanically dissociate nonadherent cells. Cell sheet fragments were stained with crystal violet (Sigma-Aldrich) and quantitated with IPLab software (Scanalytics Inc.).

Example 1

Isolation of Human Anti-Dsg3 and Anti-Dsg1 mAbs from a Phage Display Library Constructed from Lymphocytes from a Mucocutaneous PV Patient RT-PCR was used to amplify mRNA for the Ig variable-region heavy chain ($V_H$) and variable-region light chain ($V_L$) fragments from peripheral blood lymphocytes isolated from a patient with active acute mucocutaneous PV. The resulting cDNA was then cloned into a phagemid vector, which facilitated the creation of an antibody phage display library, comprising approximately $4 \times 10^8$ independent transformants. Phage particles, each displaying a particular $V_H$ and $V_L$ pair on their surface (folded into a single monovalent antigen-binding site) with the corresponding cDNA encoding the pair within the particle, were selected by panning against the extracellular domain of desmoglein substrate immobilized on ELISA plates. Four rounds of panning were conducted with scFvs selected against only Dsg3 (D3), only Dsg1 (D1), or both Dsg3 and Dsg1 (D31). Phage clones that expressed desmoglein-specific antibodies were identified after the second through fourth rounds of panning and were subsequently confirmed by ELISA, using enzyme-conjugated anti-M13 phage antibody to detect antigen-binding phage particles. 26 D3 clones, 24 D1 clones, and 13 D31 clones were randomly selected for nucleotide sequencing (see FIG. 1A for nomenclature). Of these, 16, 22, and 5 were identified as unique mAbs, respectively, based on combinations of distinct heavy and light chain variable-region sequences. To perform functional studies for this cohort of mAbs, a nonsuppressor strain of *E. coli* was used to express the recombinant human mAbs as soluble scFv molecules unlinked to phages. Soluble scFvs, which were engineered with a 6x-histidine tag and an HA peptide tag on their carboxy termini, were purified by nickel-chelation chromatography. The purity of the scFv preparation was evaluated by Coomassie staining after SDS-PAGE, which showed a single predominant protein band (FIG. 1B). Gel-filtration HPLC indicated that soluble scFvs were 92-98% monomeric (FIG. 1C). These data show that the scFvs can be easily purified and consist almost completely of monomers with little, if any, aggregation.

Example 2

Figure 2:
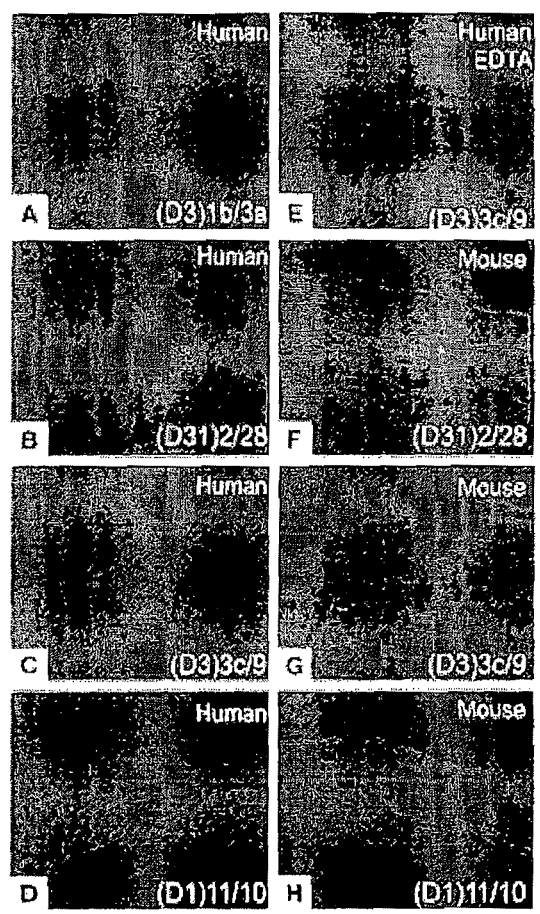
FIG. 2, comprising
Figure 3:
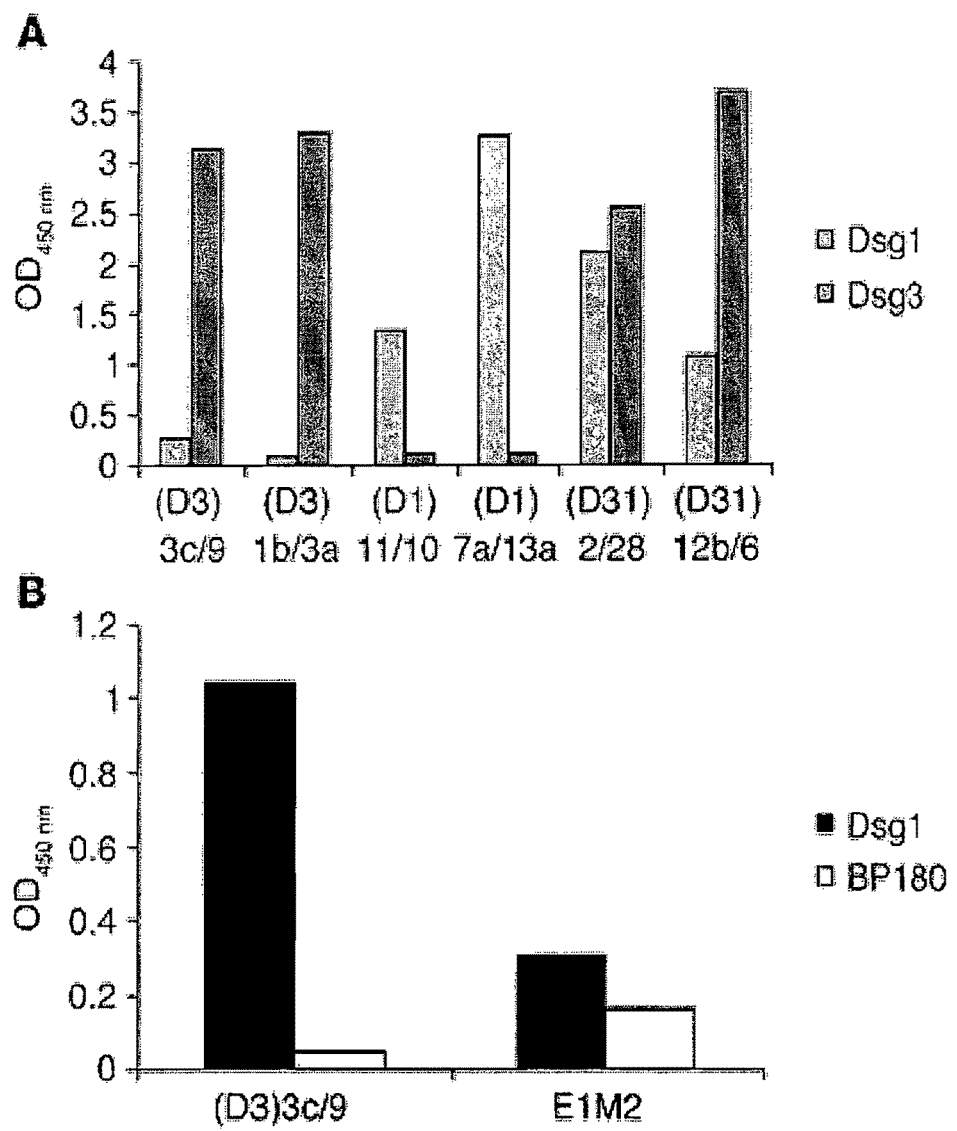
FIG. 3 comprising

The Repertoire of Human PV scFv mAbs Shows Various Patterns of Desmoglein-Specific Binding as Determined by Indirect Immunofluorescence and ELISA ScFvs were tested by indirect immunofluorescence (IIF) on normal human skin using anti-HA antibodies for detection in order to evaluate the ability of recombinant mAbs to bind native desmogleins in human tissue. In general, scFvs derived from phage libraries panned on Dsg3 showed the expected binding to the keratinocyte cell surface in the basal and immediate suprabasal layers, where Dsg3 is expressed (FIG. 2A), and those derived from libraries panned on Dsg3 and Dsg1 bound throughout the epidermis (FIG. 2B). However, 2 clones panned only on Dsg3, (D3)3c/9 and (D3)3a/9, bound throughout the epidermis (FIG. 2C and data not shown). As discussed below, by ELISA these scFv mAbs showed not only binding to Dsg3 but also slight binding to Dsg1. Interestingly, only 1 of the scFv mAbs derived from a phage library selected on Dsg1 stained human epidermis by IIF, but that antibody bound in the expected, predominantly superficial, cell surface pattern (FIG. 2D). The cohort of recombinant scFv mAbs was tested by ELISA to more precisely determine their desmoglein-binding specificities. In general, antibodies derived from libraries panned on Dsg3 bound Dsg3 but not Dsg1 [e.g., clone (D3)1b/3a; FIG. 3A]. However, clones (D3)3c/9 and (D3)3a/9, although selected for binding against only Dsg3, also demonstrated weak binding to Dsg1 (FIG. 3, A and B, and data not shown), consistent with their IIF binding throughout human epidermis (FIG. 2C). This binding to Dsg1 was specific, as a higher concentration of (D3)3c/9 bound strongly to Dsg1 but not to an irrelevant autoantigen (bullous pemphigoid 180 [BP180] antigen), and an irrelevant scFv (E1M2, a human red blood cell mAb; ref. 25) did not bind Dsg1 when used at an equivalent scFv protein concentration (FIG. 3B). As would be expected, scFvs from D1 clones bound Dsg1 by ELISA, while D31 clones that were derived from a phage library alternately panned on Dsg1 and Dsg3 bound both desmogleins (FIG. 3A). These data demonstrate isolation of anti-Dsg scFv mAbs from a patient with mucocutaneous PV, and that a single mAb can bind both Dsg3 and Dsg1. These recombinant antibodies reproduce binding of desmogleins by both ELISA and immunohistochemical assays. In order to test for pathogenicity of selected scFv mAbs in the neonatal mouse model of pemphigus, it was needed to demonstrate scFv binding to mouse epidermis by IIF. Five D31 mAbs demonstrated binding throughout mouse epidermis, with more superficial staining (FIG. 2F). Interestingly, most of the D3 scFv mAbs did not bind to mouse epidermis. However, clone (D3)3c/9 did bind to mouse epidermis, but, unlike in human epidermis, in which it bound throughout, it bound predominantly to the cell surface in the basal layer (FIG. 2G), suggesting that, in mice, it only binds to Dsg3. Similar to findings with human epidermis, most D1 scFv mAbs did not bind mouse epidermis, with the exception of (D1)11/10, which bound throughout (FIG. 2H). Therefore, not all human autoantibodies bind to mouse skin, and some of those that do may bind in differing patterns. Thus, the results presented herein indicate that there may be limitations in interpreting pathogenicity (especially the lack of pathogenicity) of serum-derived polyclonal human antibodies in the neonatal mouse model.

Example 3

Figure 4:
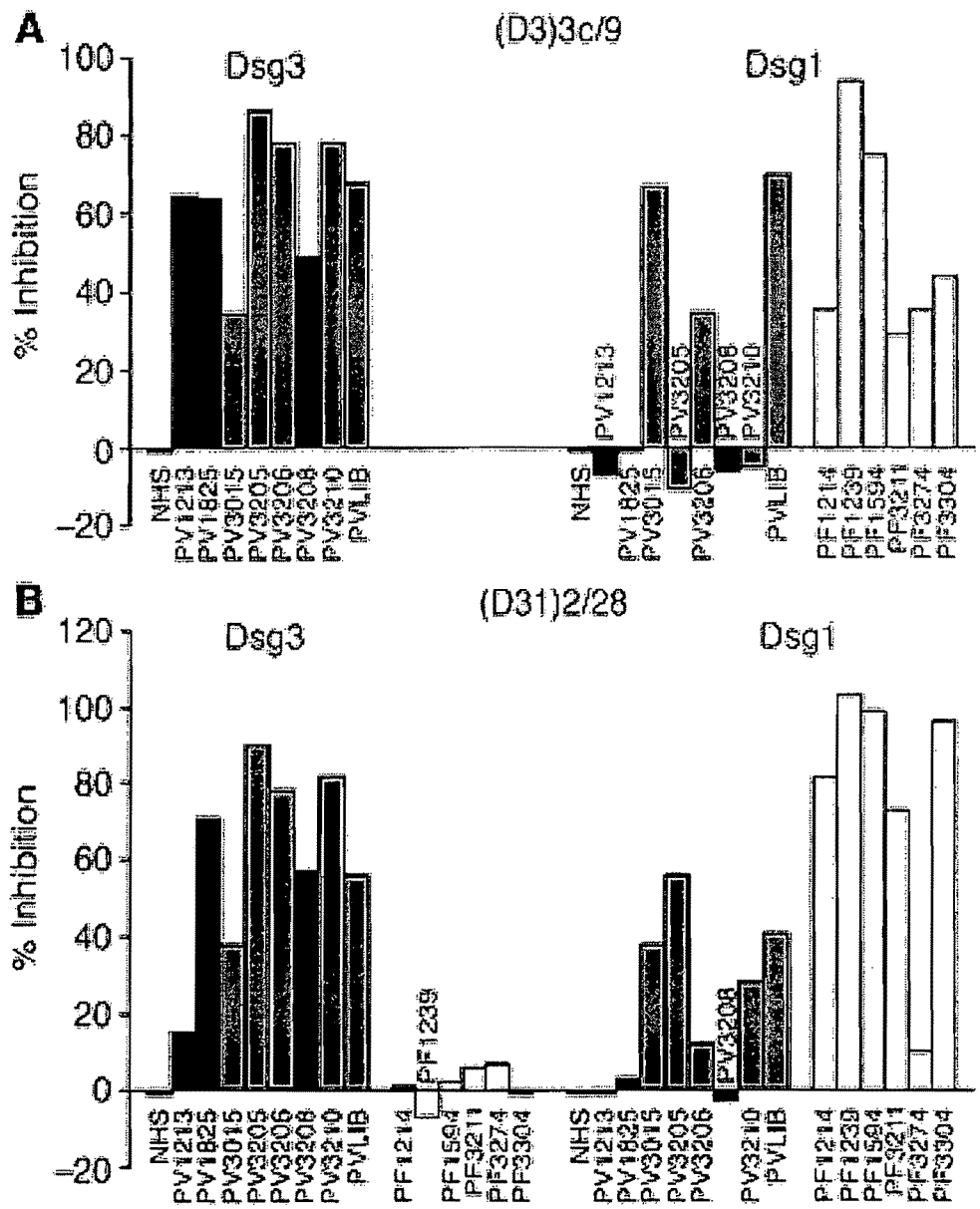
FIG. 4 comprising

Sera from PV and PF Patients Block Binding of scFv mAbs to Desmogleins in Inhibition ELISA Studies To determine whether sera from different pemphigus patients bind similar or identical epitopes to those defined by the scFv mAbs cloned from selected PV patient, inhibition ELISA assays were performed. PF sera containing anti-Dsg1 antibodies, PV sera containing anti-Dsg3 antibodies [PV(3) sera], or PV sera containing both anti-Dsg3 and anti-Dsg1 antibodies [PV(3+1) sera] were evaluated for their ability to inhibit binding of scFv mAbs to desmoglein substrates. FIG. 4 shows representative inhibition ELISA studies with scFvs (D3)3c/9 (FIG. 4A) and (D31)2/28 (FIG. 4B). Inhibition greater than 20% was scored as positive. All 8 PV sera tested (including the PV patient sera used to make the phage display library [PVLIB]) inhibited binding of (D3)3c/9 to Dsg3 (FIG. 4A, left). All 6 of the PF sera tested, 3 of 5 PV(3+1) sera (including PVLIB), and none of the 3 PV(3) sera inhibited binding of (D3)3c/9 to Dsg1 (FIG. 4A, right). The 2 PV(3+1) sera that did not inhibit (D3)3c/9 binding to Dsg1 demonstrated low (less than 1:20) ELISA titers against Dsg1, potentially accounting for the lack of inhibition. Seven of 8 PV sera (including PVLIB) and 0 of 6 PF sera inhibited (D31)2/28 binding to Dsg3 (FIG. 4B, left). Five of 6 PF sera, 4 of 5 PV(3+1) sera (including PVLIB), and 0 of 3 PV(3) sera inhibited binding of (D31)2/28 to Dsg1 (FIG. 4B, right). The number of PV patient- or PF patient-derived sera that blocked binding of each scFv to Dsg3 or Dsg1 was tabulated, with inhibition greater than 20% scored as positive (Table 1). D31 and D1 clones were inhibited from binding to Dsg1 by both PF sera and PV(3+1) sera, but not by normal human control or PV(3) sera, which indicates that the inhibition of scFv binding is due to the presence of anti-Dsg1 antibodies in pemphigus sera. These data suggest that epitopes defined by the scFv mAbs derived from selected mucocutaneous PV patient are also bound or blocked by sera from most pemphigus patients.

TABLE 1

Summary of inhibition ELISA studies

| ScFv | PV sera | | PF sera | |
|---|---|---|---|---|
| | Dsg3 | Dsg1 | Dsg3 | Dsg1 |
| (D1)5b/16a | — | 4/4 | — | 6/6 |
| (D1)6b/14 | — | 1/5[A] | — | 6/6 |
| (D1)7a/13a | — | 2/4 | — | 6/6 |
| (D1)8/12a | — | 1/5[A] | — | 6/6 |
| (D1)11/10 | — | 0/5[B] | — | 0/6[B] |
| (D3)1b/3a | 7/8 | — | — | — |
| (D3)1d/2c | 7/7 | — | — | — |
| (D3)1g/2e | 7/7 | — | — | — |
| (D3)1i/4d | 8/8 | — | — | — |
| (D3)3a/9 | 8/8 | 3/5 | — | 6/6 |
| (D3)3b/8 | 8/8 | — | — | — |
| (D3)3c/9 | 8/8 | 3/5 | 0/2 | 6/6 |
| (D3)4/30 | 7/7 | — | — | — |
| (D31)12a/5 | 8/8 | 1/5[A] | 0/6 | 6/6 |
| (D31)12b/6 | 8/8 | 1/5[A] | 0/6 | 6/6 |
| (D31)2/28 | 7/8 | 4/5 | 0/6 | 5/6 |
| (D31)2/29 | 7/7 | 4/4 | — | 6/6 |

[A]Reactions in which sera were used at a standard dilution of 1:25 instead of 1:6.25. In these cases, lack of inhibition may reflect lower titers of blocking antibody during ELISA inhibition, since in inhibition studies of PV(3 + 1) sera against Dsg1-reactive scFvs, higher concentrations of sera resulted in higher levels of inhibition.
[B]Paradoxically, PF and PV(3 + 1) sera potentiated binding of (D1)11/10 to Dsg1.
—, not tested.

Example 4

Phage Display Isolates Both Pathogenic and Nonpathogenic scFv Antibodies

Figure 5:
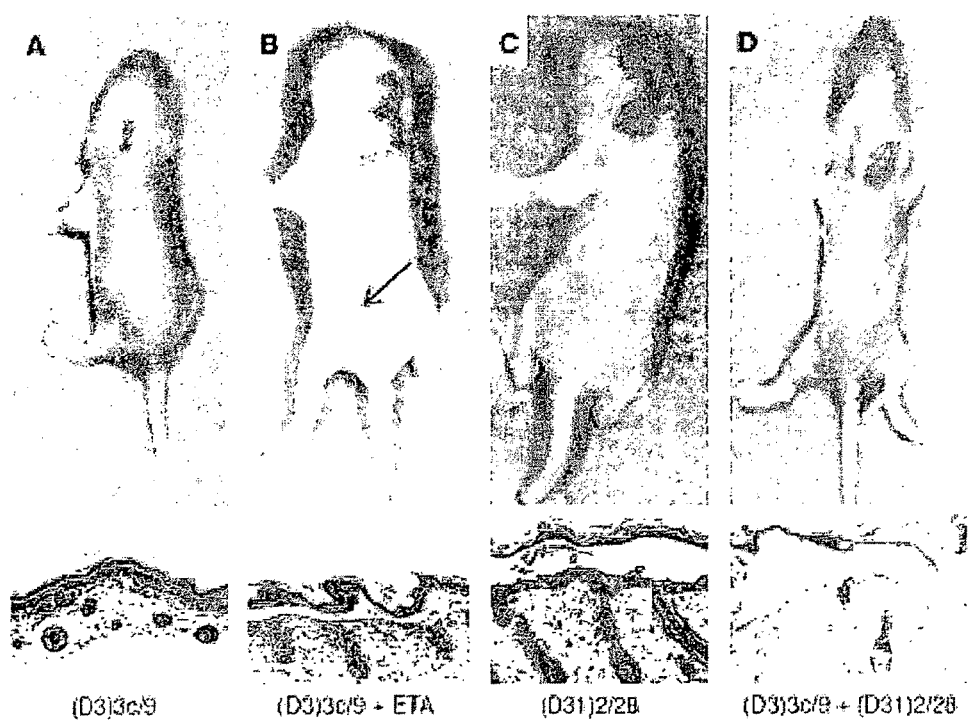
FIG. 5 comprising
Figure 6:
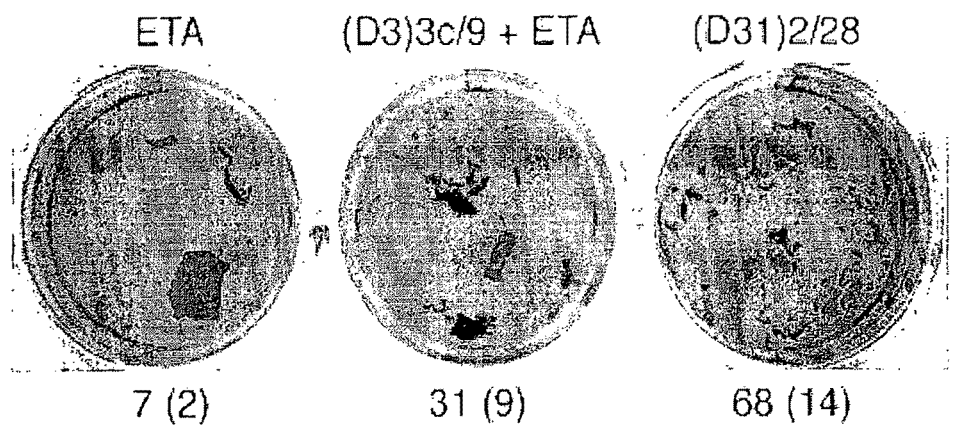
FIG. 6 is an image illustrating ScFv mAbs that can cause dissociation of cultured human epidermal keratinocytes. Cultured human keratinocytes were incubated with ETA with or without scFvs and then treated with dispase to release cell monolayers. Released cell sheets were exposed to mechanical shear stress to evaluate intercellular adhesion. The total number of cell sheet fragments for each treatment is shown as a mean (SD).

ScFv polypeptides consist of a single monovalent variable-region antigen-binding site. To evaluate the ability of anti-Dsg scFvs to disrupt keratinocyte adhesion in vivo, scFvs that bound mouse skin by IIF were administered to neonatal mice by s.c. injection. To determine whether anti-Dsg3 scFvs were pathogenic, in some cases low-dose exfoliative toxin A (ETA) was co-injected to inactivate Dsg1 in the deep epidermis, since induction of typical PV suprabasilar blistering requires inactivation of both desmogleins. Injection of PBS, lowdose ETA alone, or (D3)3c/9 alone did not result in skin blistering of neonatal mice (FIG. 5A and data not shown). However, concomitant injection of (D3)3c/9 with low-dose ETA to cleave Dsg1 caused blistering of the skin within 2-6 hours (FIG. 5B). Indirect and direct immunofluorescence on mouse epidermis confirmed the presence of scFvs in the serum and skin of injected mice, with IIF titers ranging from 1:1,600 to 1:4,000. Histologic analysis of skin sections from mice injected with (D3)3c/9 and low-dose ETA demonstrated suprabasilar acantholysis characteristic of PV blisters (FIG. 5B, lower panel). Subcutaneous injection of (D31)2/28 (without ETA) into neonatal mice resulted in blistering of the skin within 3 hours, with histology demonstrating superficial acantholysis similar to lesions seen in PF (FIG. 5C). Clinical blistering was observed with BF titers of mouse sera as low as 1:20. In contrast, injection of (D31)12a15, (D31)12b/6, and (D31)12c/7 into neonatal mice did not result in skin blisters, despite IIF experiments detecting scFvs in mouse sera at titers ranging from 1:50 to 1:4,000 (data not shown). Because the patterns of histologic blistering implied recognition of murine Dsg3 (mDsg3) by (D3)3c/9 and murine Dsg1 (mDsg1) by (D31)2/28, injection of both scFvs into neonatal mice was performed. IIF titers after scFv injection ranged from 1:400 to 1:4,000. Mice developed gross blisters within 2 hours, which on histologic examination demonstrated suprabasilar blistering identical to what is observed in lesions of mucocutaneous PV (FIG. 5D). These data show that some, but not all, scFv monovalent antibodies are pathogenic in mice and presumably have the ability to disrupt adhesion by their target desmogleins. However, given that anti-Dsg scFv binding patterns appear to be species-specific, mouse models may not allow for accurate evaluation of pathogenicity of human autoantibodies for human desmogleins. To evaluate pathogenicity of scFvs against human keratinocytes, an assay for dissociation of cultured human keratinocytes was used (Ishii et al., 2005, J. Invest. Dermatol. 124: 939-46). Cultured primary human epidermal keratinocytes express Dsg1 and Dsg3 with minimal levels of Dsg2 (Ishii et al., 2005, J. Invest. Dermatol. 124: 939-46). Incubation of cultured keratinocytes with ETA alone did not cause significant dissociation (FIG. 6, left). However, incubation of keratinocytes with (D3)3c/9 in the presence of ETA resulted in cell sheet dissociation (FIG. 6, middle). (D31)2/28 was able to induce cell sheet dissociation in the absence of ETA (FIG. 6, right). These data suggest that (D3)3c/9 can interfere with adhesion mediated by human Dsg3 and that (D31)2/28 can disrupt both human Dsg3 and human Dsg1. Incubation of cultured keratinocytes with (D3) 1b/3a, (D3)1d/2c, (D3)1g/2e, (D3)1i/4d, (D31)12a/5, and (D31)12b/6 did not result in cell sheet dissociation, providing further evidence that both pathogenic and nonpathogenic pemphigus antibodies were isolated.

The observation that some of the antibodies tested were nonpathogenic led to experiments to test whether these antibodies could be used for targeted therapy. As set forth below, experiments were conducted to develop a system of delivering a biologically active protein to the epidermis using cloned scFv that bind epidermis without causing pathology. (See below for e.g., Examples 7 and 8).

Example 5

Epitope Mapping on Domain-Swapped Desmogleins Shows that Pathogenic Epitopes Defined by scFv mAbs are on the Amino Termini of Dsg1 and Dsg3

Figure 7:
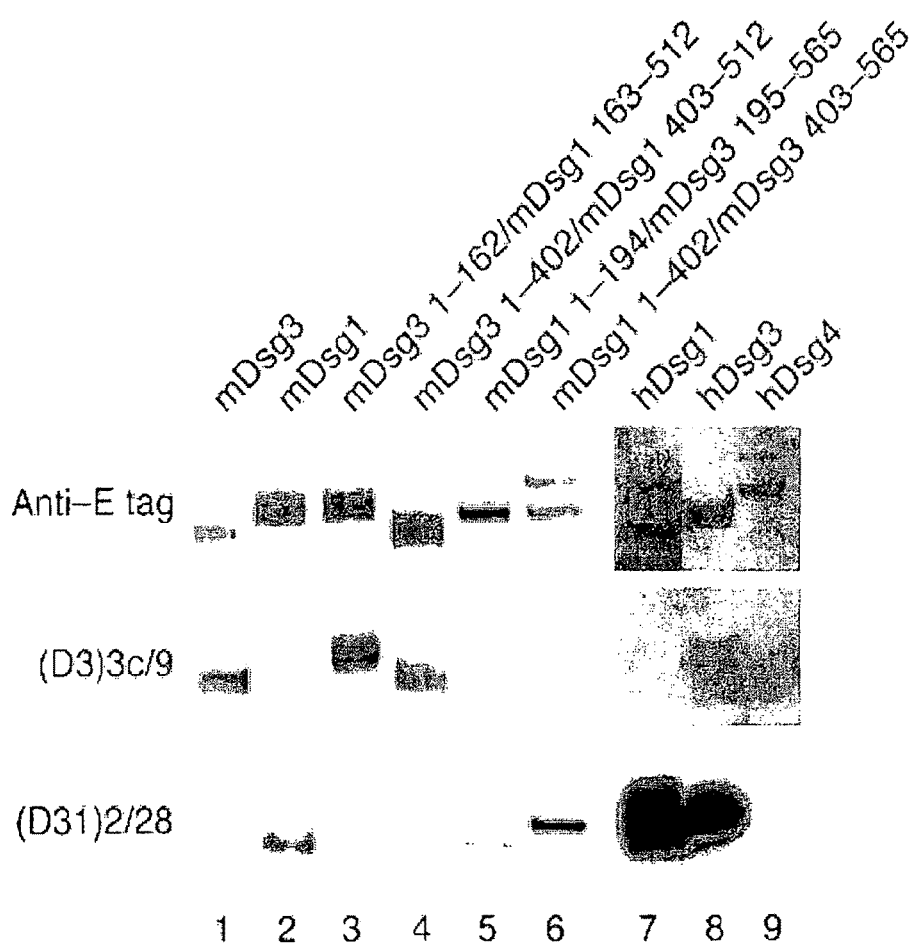
FIG. 7 is an image depicting Epitope mapping of (D3)3c/9 and (D31)2/28 against mouse and human desmogleins. Wild-type and domain-swapped extracellular domains of mDsg1 and mDsg3 (lanes 1-6) or wild-type extracellular domains of human desmogleins (hDsgs) 1,3, and 4 (lanes 7-9) were produced in baculovirus and immunoprecipitated with scFv mAbs. Desmoglein proteins bound by human scFv mAbs were detected by immunoblot analysis using antibody against E tag, which was engineered onto the carboxyterminal domain of recombinant desmoglein molecules. The top panel shows the immunoblot of the recombinant and chimeric desmogleins detected with anti-E tag. The bottom 2 panels show the results of the immunoprecipitation-immunoblotting studies.
Figure 8:
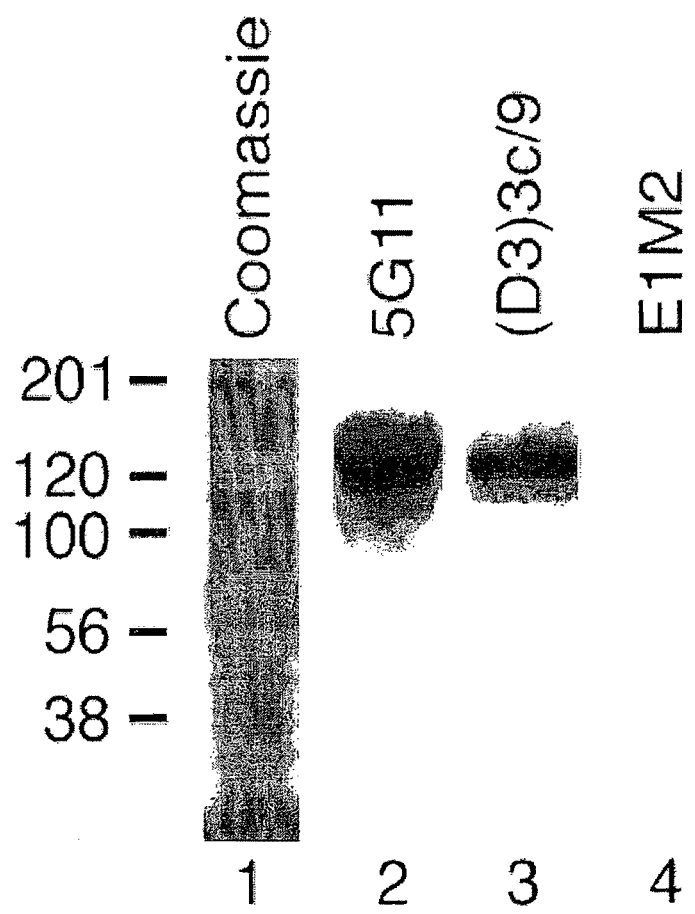
FIG. 8 is an image depicting an aspect of the invention in which PV scFv mAbs recognize primarily but not exclusively conformational epitopes on desmogleins. Immunoblot analysis of human keratinocyte extract using (D3)3c/9. Lane 1, Coomassie blue-stained human keratinocyte extract. Lane 2, murine anti-Dsg3 mAb 5G11. Lane 3, (D3)3c/9. Lane 4, E1M2 (control anti-human red blood cell scFv).

The different binding patterns of scFvs on mouse and human epidermis, together with the neonatal mouse pathogenicity data, suggested that (D3)3c/9 recognized only mDsg3 and not mDsg1, and that (D31)2/28 recognized only mDsg1 and not mDsg3. To confirm these empirical observations and further delineate the site of scFv binding, epitope mapping of (D3)3c/9 and (D31)2/28 on domain swapped mouse desmogleins was performed. FIG. 7 (lanes 1-6) shows that (D3)3c/9 binds an epitope on mDsg3 contained within the amino-terminal 162 amino acids. No binding of (D3)3c/9 to mDsg1 was detected. Conversely, (D31)2/28 recognized epitopes in the 194-amino acid amino-terminal domain of mDsg1 with no detectable binding to mDsg3. Therefore, consistent with previously published studies of polyclonal human sera and a pathogenic mouse anti-Dsg mAb (Sekiguchi et al., 2001, J. Immunol., 167:5439-5448; Li et al., 2003 J. Exp. Med., 197: 1501-1510; Tsunoda et al., 2003, J. Immunol., 170:2170-2178), pathogenic recombinant human scFvs presented herein bind epitopes on the amino termini of desmogleins. The finding of such intense superficial staining of human epidermis with (D3)3c/9 (FIG. 2C), which demonstrated only weak ELISA binding to Dsg1 (FIG. 3B), led to the investigation of whether this scFv might also bind Dsg4, which has previously been reported to be expressed in the superficial layers of interfollicular human epidermis (Kljuic et al., 2003, Cell., 113:249-260). However, neither (D3)3c/9 nor (D31)2/28, which also stains superficial epidermis, bound to human Dsg4 (FIG. 7, lane 9).

Example 6

Figure 9:
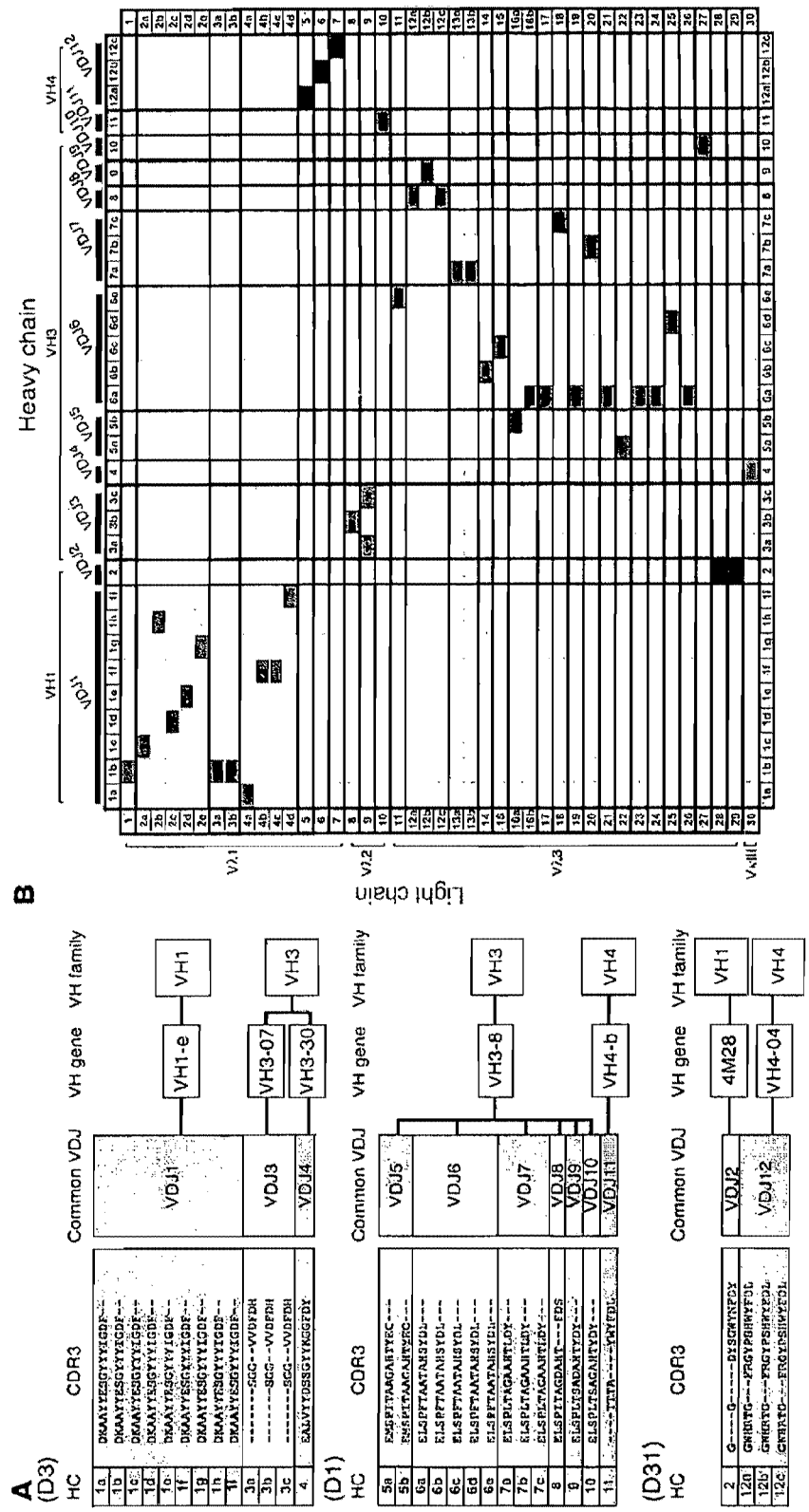
FIG. 9 comprising

PV mAbs with Different Desmoglein-Binding Specificities Demonstrate Different Patterns of Heavy and Light Chain Gene Restriction The third complementarity-determining region (CDR3) comprises the unique genetic sequence spanning the VDJ recombinatory junctions of the Ig heavy chain (Collins et al., 2003, Pharmacol. Ther., 100:157-170). This region defines a particular B lymphocyte and all of its clonal progeny. To determine the genetic interrelatedness of antibodies captured by phage display, a total of 63 mAbs (26 D3, 24 D1, and 13 D31) were randomly selected for nucleotide sequencing of the heavy and light chain variable regions. Several mAbs shared identical CDR3 sequences, indicating derivation from a common parental B cell clone. Twelve unique CDR3 sequences, designated as VDJ1-VDJ12, were identified among the 63 desmoglein-reactive clones. FIG. 9A shows the CDR3 alignments for D3, D1, and D31 heavy chain sequences, together with the $V_H$ gene and gene family usage. Both the heavy and the light chain utilization for each unique anti-Dsg mAb is depicted in FIG. 9B. Of the 26 D3 mAbs, there were 13 unique heavy chain sequences represented, which could be grouped into 3 common VDJ families based on their CDR3 sequence, with each VDJ family representing a clonal population derived from a common B cell parental clone (FIG. 9A, upper panel). Restriction of D and JH gene segments was also observed, with exclusive utilization of only 2 D gene segments and JH4b for all D3 clones. D3 clones displayed preferential usage of the VH1/Vλ1 gene families (FIG. 9B). However, clone (D3)3c/9, which demonstrates binding of Dsg1 in addition to Dsg3, used VH3Nκ2. (D3)3a/9, with the same desmoglein-binding specificity as (D3)3c/9, had heavy and light chain gene usage identical to that of (D3)3c/9 but different heavy chain somatic mutations. These data suggest that heavy and light chain gene family usage may determine the binding specificity of autoantibodies against desmogleins. The 24 D1 mAbs derived from 7 different parental B cell clones (identified as VDJ5-VDJ11) (FIG. 9A, middle panel). All but 1 of the 14 unique D1 heavy chain sequences were encoded by the VH3-8 gene. D1 clones showed preferential usage of VH3/Vλ3 (FIG. 9B), with the exception of clone (D1)11/10, which used VH4/Vλ2. Interestingly, (D1)11/10 was also unique among D1 clones in its binding of human epidermis by BT. Analysis of 13 D31 clones revealed 4 unique heavy chain sequences derived from 2 different VDJ rearrangements (FIG. 9A, lower panel). D31 clones showed restricted but distinct $V_H$ (VH1 and VH4) and $V_L$ (Vλ1 and Vλ3) gene family usage (FIG. 9B). Of the 26 D3, 24 D1, and 13 D31 sequenced clones, 16, 22, and 5 unique heavy and light chain combinations were identified, respectively. As shown in FIG. 9B, D3, D1, and D31 clones demonstrated restricted and nonoverlapping usage of both heavy and light chain genes. In some cases, multiple antibodies of the same heavy and light chain gene family were identified, differing only by somatic mutation from germ-line $V_H$ and $V_L$ Ig genes (e.g., VDJ1 with light chain family 2). That these mutations are not the result of PCR errors in library construction but more likely reflect a somatic mutation process in vivo is supported by the fact that Taq polymerase under the conditions used in these studies is associated with less than 1 error per 9,000 nucleotides (Tindall et al., 1988, Biochemistry., 27:6008-6013). PCR with such a low error rate could not account for the number of mutations detected in the clones described herein (i.e., as many as 20 or more per $V_H$ or $V_L$, each comprising approximately 350 bp) or their position (concentrated in CDRs).

Example 7

Injection of Cloned Anti-Dsg3 non-Pathogenic scFv into Adult Mice

ScFv, cloned from patients with pemphigus, were tested for pathogenicity (i.e. ability to cause blisters or pathology in the epidermis) in neonatal mice and by injection in human skin organ culture. Many of these cloned scFv did not cause any detectable pathology, even though they bind strongly to the cell surface of keratinocytes.

One of these non-pathogenic scFv anti-Dsg3 cloned from a pemphigus patient was injected intraperitoneally into adult mice. Mice were sacrificed at one and two days after injection. The HA-tag on the scFv was detected by immunofluorescence with anti-HA in various parts of the skin. FIG. 10A-10D and 10G show that the scFv bound the cell surface of the keratinocytes in the thin epidermis, in the hair follicle, in the eccrine glands of the paw, and in the keratinocytes deep in the paw epidermis (i.e. the site of Dsg3); and persisted for 2 to 3 days without apparent change in distribution or pathology. These data suggest that such non-pathogenic scFv can be used to target epidermis and its adnexal structures.

The next set of experiments were designed to demonstrate that an anti-Dsg3 scFv cloned from a PV patient binds in vivo without causing pathology. Preliminary results demonstrate that most cloned scFv from a PV patient by phage display did not cause pathology when injected into neonatal mice or human skin organ culture.

Figure 10A:
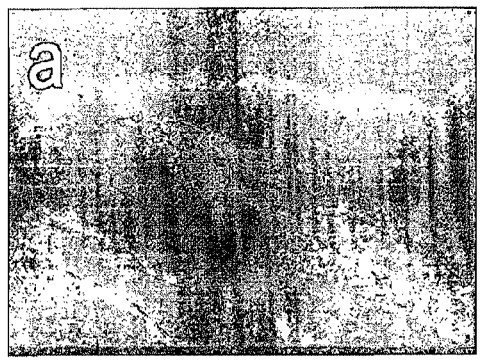
FIGS. 10A-10G, is a series of images depicting skin after injection of scFv Px4-4 (also termed D(31)12b/6) and Px4-3 (also termed D(31)2/29), scFvs that bind both human and mouse Dsg3 and were derived by phage display from a pemphigus vulgaris patient. The scFvs have an HA tag that is detected by immunofluorescence with anti-HA antibodies. 10A-D: mice were injected intraperitoneally with scFv Px4-4 at time 0 and 6 hours; 10A-10B, flank skin with hair follicles; 10C and 10D, paw skin (with eccrine duct in 10D). 10A and 10C, time=1 day; 10B and 10D, time=2 days. ScFv Px4-4 localizes to epithelium and remains there for at least 2 days with no apparent change or pathology.
Figure 10B:
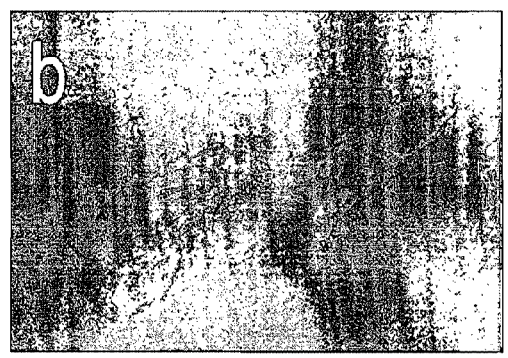
Figure 10C:
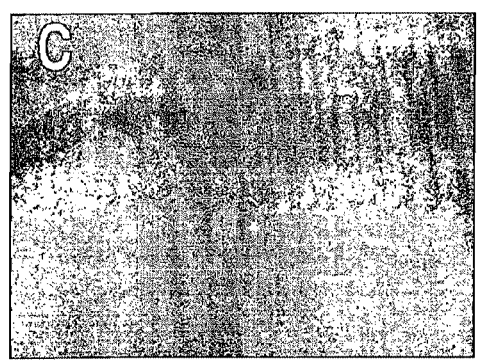
Figure 10D:
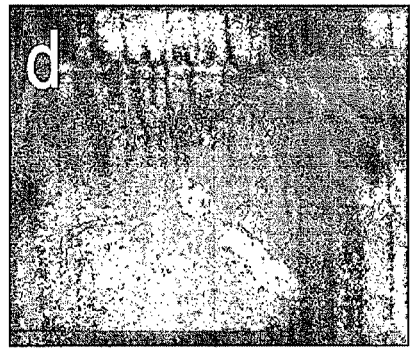
Figure 10E:
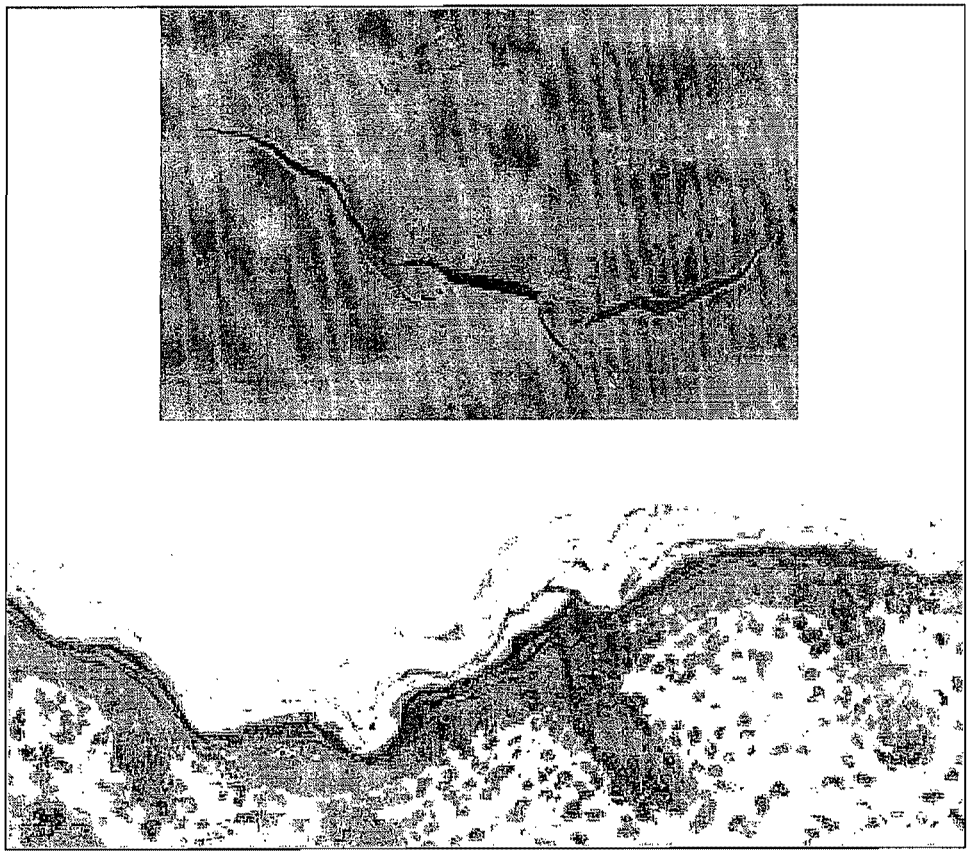
Figure 10F:
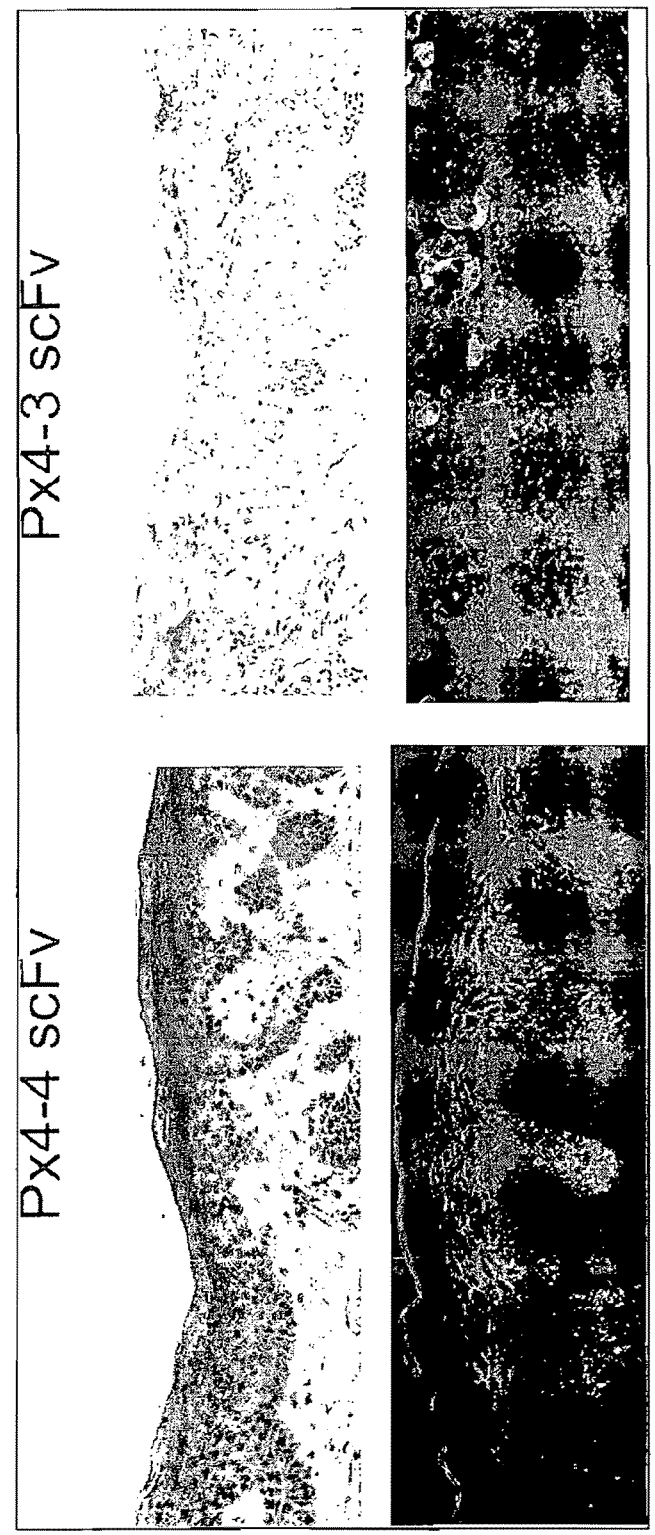

As a non-limiting example, scFv Px4-4 (also termed 12b/6), an scFv that binds both human and mouse Dsg3, containing an HA tag, was injected intraperitoneally into adult mice. It was observed that Px4-4 bound to Dsg3 (which is localized on the cell surface of the epidermal basal cells) and did not cause any gross or histologic pathology (e.g., microscopic blister) (FIG. 10E). When normal human skin in organ culture was injected with Px4-4 scFv, pathology was also not detected even though Px4-4 scFv was present in the skin as measured by direct immunofluorescence with anti-HA. Positive control Px4-3 shows acantholysis with antibody binding (FIG. 10F).

Figure 10G:
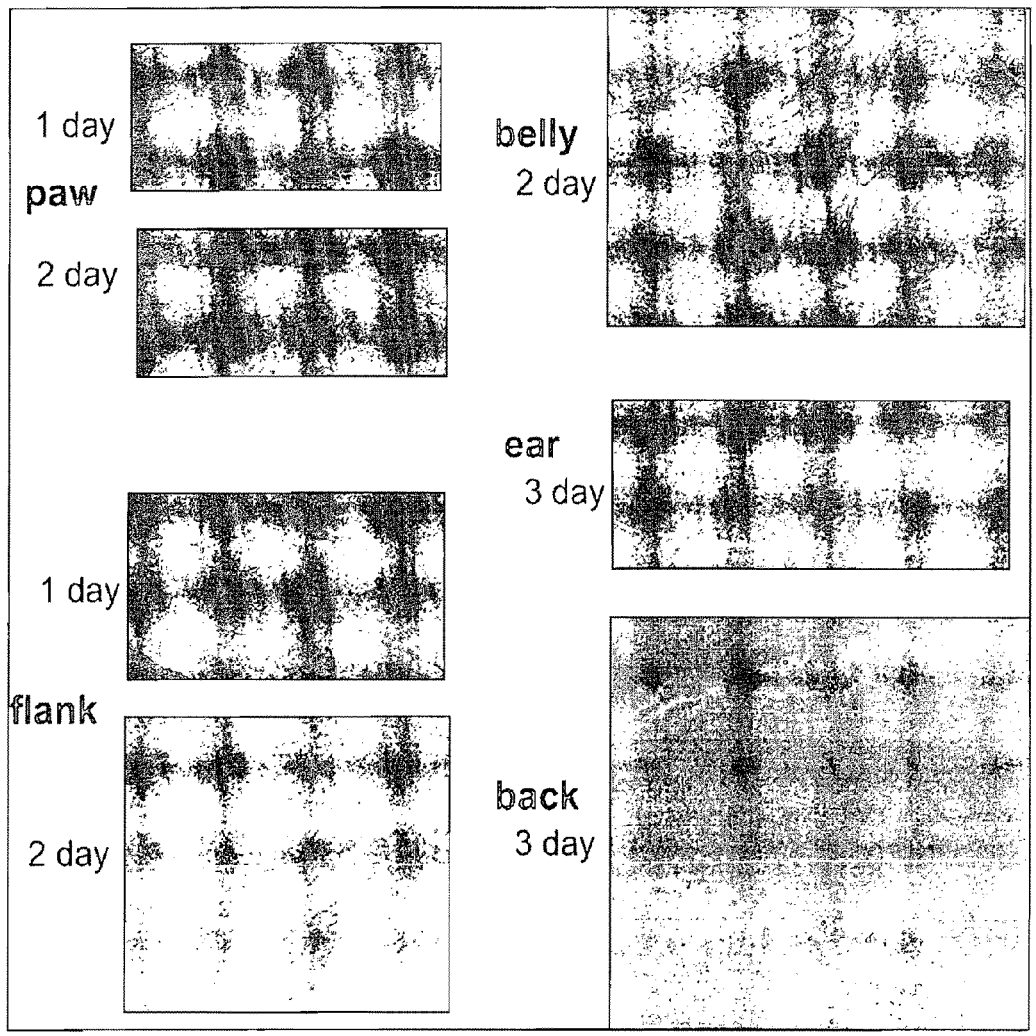

Direct immunofluorescence with anti-HA shows that Px4-4 scFv injected intraperitoneally into adult mice locates to the cell surface of keratinocytes and persists for at least 3 days. Staining was observed on basal keratinocytes in paw (statum corneum shows non-specific staining) and on keratinocytes in outer root sheath of hair follicles. Epidermis in flank, belly and back is only one cell layer, making staining difficult to appreciate, but ear epidermis was cut en face to better show staining in epidermis (FIG. 10G).

Example 8

Targeting of Proteins Using scFv Isolated from Patients with Autoimmune Disease

The next set of experiments were designed to develop a system for delivering biologically active proteins to the epidermis using cloned scFv that bind epidermis without causing pathology as a means for targeted therapy. Without wishing to be bound by any particular theory, it is believed that a desirable protein such as a pro-apoptotic or an immuno-inhibitory protein can be delivered to the epidermis and would act as an "immunological gate", inactivating disease-causing lymphocytes that migrate into epidermis.

As discussed elsewhere herein, a non-pathogenic anti-Dsg3 scFv was obtained using the technique of phage display to clone a group of monoclonal scFv from a pemphigus patient (most of these antibodies were not pathogenic as they did not cause blistering or loss of adhesion of keratinocytes as seen in pemphigus) when injected into neonatal mice or normal human skin (FIGS. 10E-10G).

The non-pathogenic antibodies are candidates for targeted drug delivery. For example, such antibodies bind Dsg3 on the cell surface of keratinocytes in the basal layer of the epidermis and can deliver agents that can interact with lymphocytes migrating into the epidermis after they traverse the basement membrane.

Figure 11:
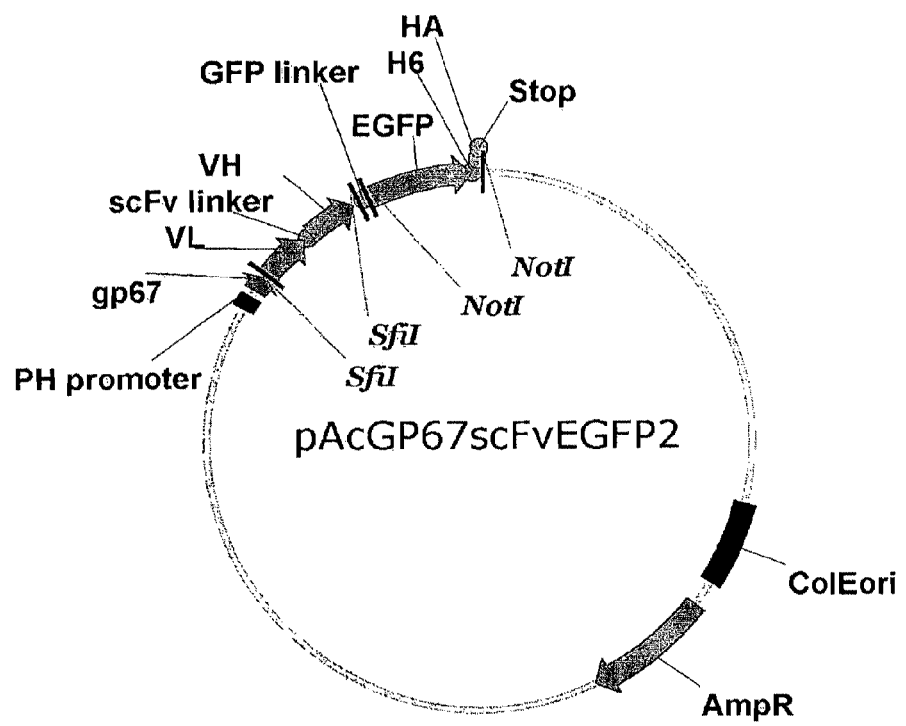
FIG. 11 is an image depicting the baculovirus transfer vector used to produce chimeric scFv-EGFP protein. Standard phage display isolates scFv that can be directionally cloned into SfiI sites. EGFP coding sequence can be excised with NotI and another cDNA can be cloned into the NotI site to make a chimeric protein with the scFv. EGFP is used as an easily visualized test protein to determine if scFv can deliver proteins to the normal epidermis or epithelium.

To test whether such scFv could target a protein to epithelia, a baculovirus transfer vector was constructed that contained DNA encoding an anti-Dsg3 scFv attached by a linker to enhanced green fluorescence protein (EGPF) with a carboxy-terminal His tag (for purification on a nickel column) and hemagglutinin epitope (HA) tag (for detection with anti-HA antibodies) (FIG. 11) based on a published protocol (Ding et al., 1997, J. Invest. Dermatol., 109:592-5963). This vector was used to create baculovirus, which was used to infect insect cells which secreted the encoded chimeric scFv-EGFP protein. The vector contains a highly efficient signal peptide (gp67) to allow secretion of the protein into the insect cell media. The scFv cDNA is cloned into a restriction site (SfiI) that allows other phage cloned scFv cDNAs, which are isolated from the phagemid vector with the same SfiI enzyme, to be easily substituted. Any protein can be cloned after a short linker into a NotI enzyme site. A coding sequence for 6 histidines (H6) is added for purification of the chimeric protein and for a hemagglutination peptide (HA) epitope for detection of the protein product with anti-HA antibodies.

Figure 12:
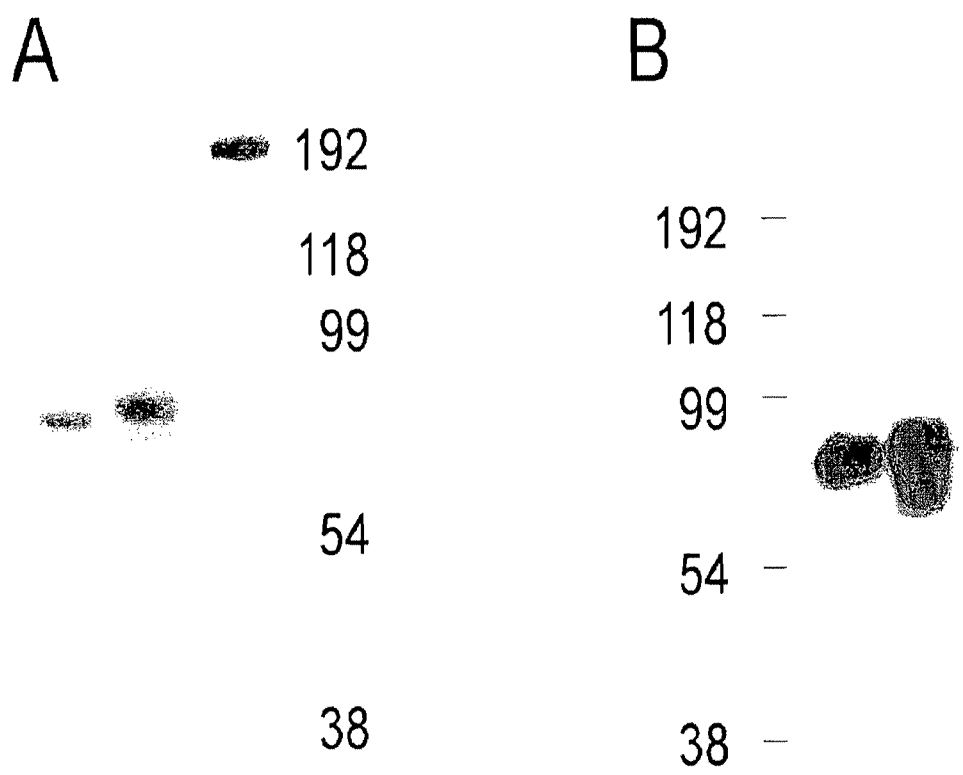
FIG. 12, comprising
Figure 13:
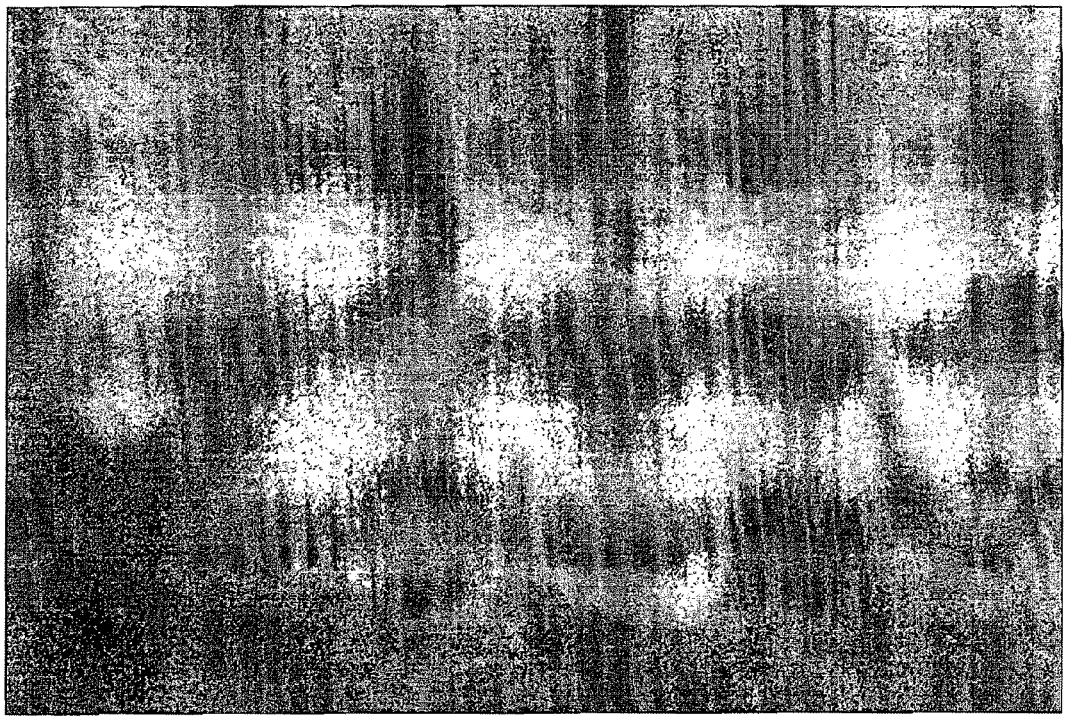
FIG. 13 is a image depicting immunofluorescence of EGFP on monkey esophagus after incubation with scFv 4B3-EGFP recombinant protein produced by insect cells. Media of cells was diluted 1:256. ScFv-EGFP binds to the cell surface of the keratinocytes in the esophagus, illustrating that the scFv can localize the EGFP protein to the expected part of the tissue.

The medium containing such insect cells can be monitored by fluorimetry to detect the amount of secretion of EGFP. Western blotting with anti-HA of the media demonstrated that there was one major HA-labelled protein with minimal degradation, and this protein could be purified on a nickel column as shown by Coomassie Blue staining of the purified protein on SDS-PAGE (FIG. 12). Finally, the chimeric protein bound to the cell surface of keratinocytes, as demonstrated by positive EGFP immunoflourescence after it was incubated on sections of monkey esophagus (FIG. 13). Similar preliminary studies show that the chimeric scFv-EGFP protein can be injected in mice or human skin organ culture and binds the keratinocytes cell surfaces. Thus, it is shown herein that scFv can deliver the EGFP protein to its target (Dsg3) on the cell surface of keratinocytes.

Anti-desmoglein scFv derived from patients having pemphigus vulgaris have also been developed. These antibodies were linked to an enhanced green fluorescent protein (EGFP) that is known to localize to epidermal cells.

Figure 14A:
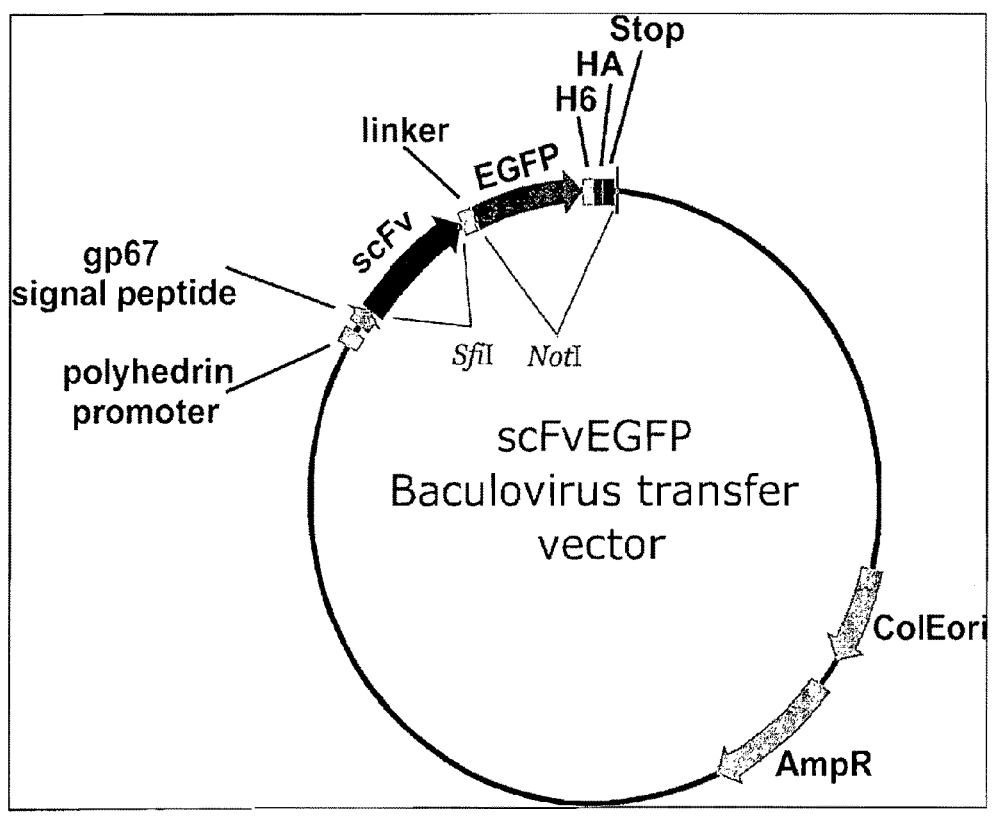
FIGS. 14A through 14E, is a series of images that demonstrate the production of recombinant scFv-EGFP chimeric protein, its purification, and injection in mice. 4B3 (also called D(3)3c/9) and Px4-4 (also termed D(31)12b/6) are both anti-Dsg scFv derived from a PV patient.
Figure 14B:
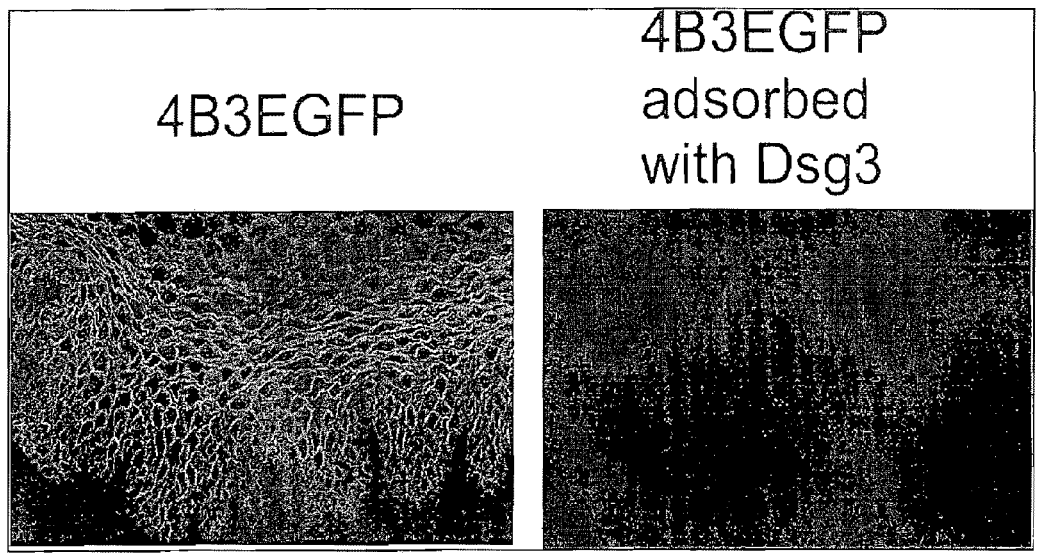
Figure 14C:
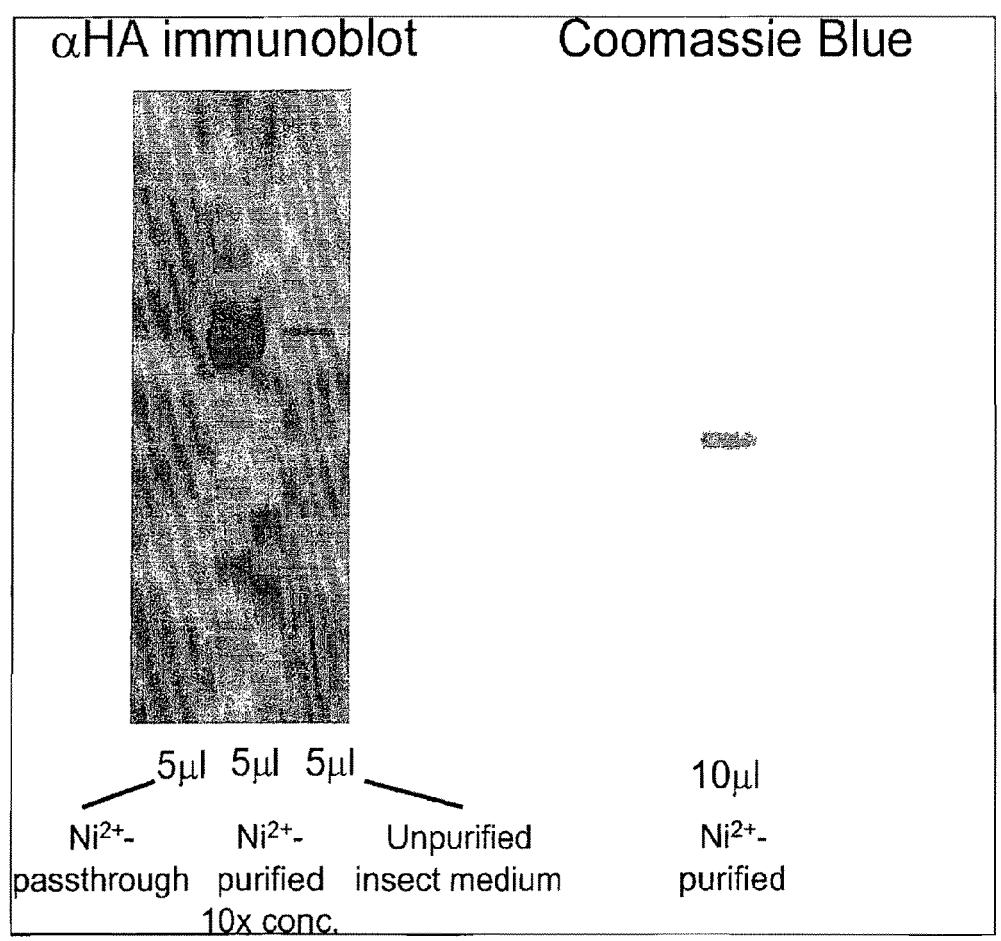

As a non-limiting example of baculovirus produced recombinant scFv-EGFP chimeric protein, 4B3 (an anti-Dsg3 scFv) was cloned into the modular baculovirus transfer vector (FIG. 14A), and produced 4B3-EGFP chimeric protein with the H6 and HA tags. As determined by EGFP fluorescence of frozen sections of monkey esophagus incubated with the media of baculovirus-infected insect cells, the chimeric protein was secreted and bound Dsg3 on the epithelial cells at titers of approximately 1:200 (FIG. 14B). The chimeric protein was purified from the insect cell media and concentrated by affinity purification on a nickel column, as shown by Coomassie Blue staining on SDS-PAGE and by Western blotting (FIG. 14C). Approximately 400 µg of nickel-purified chimeric protein was obtained from 10 ml of insect cell supernatant. Fluorimetry for GFP fluorescence of the chimeric protein indicated that essentially all the EGFP bound to a nickel column, and affinity chromatography on a recombinant Dsg3 showed that essentially all GFP was linked to functional anti-Dsg3 antibody (FIG. 14D).

Figure 14D:
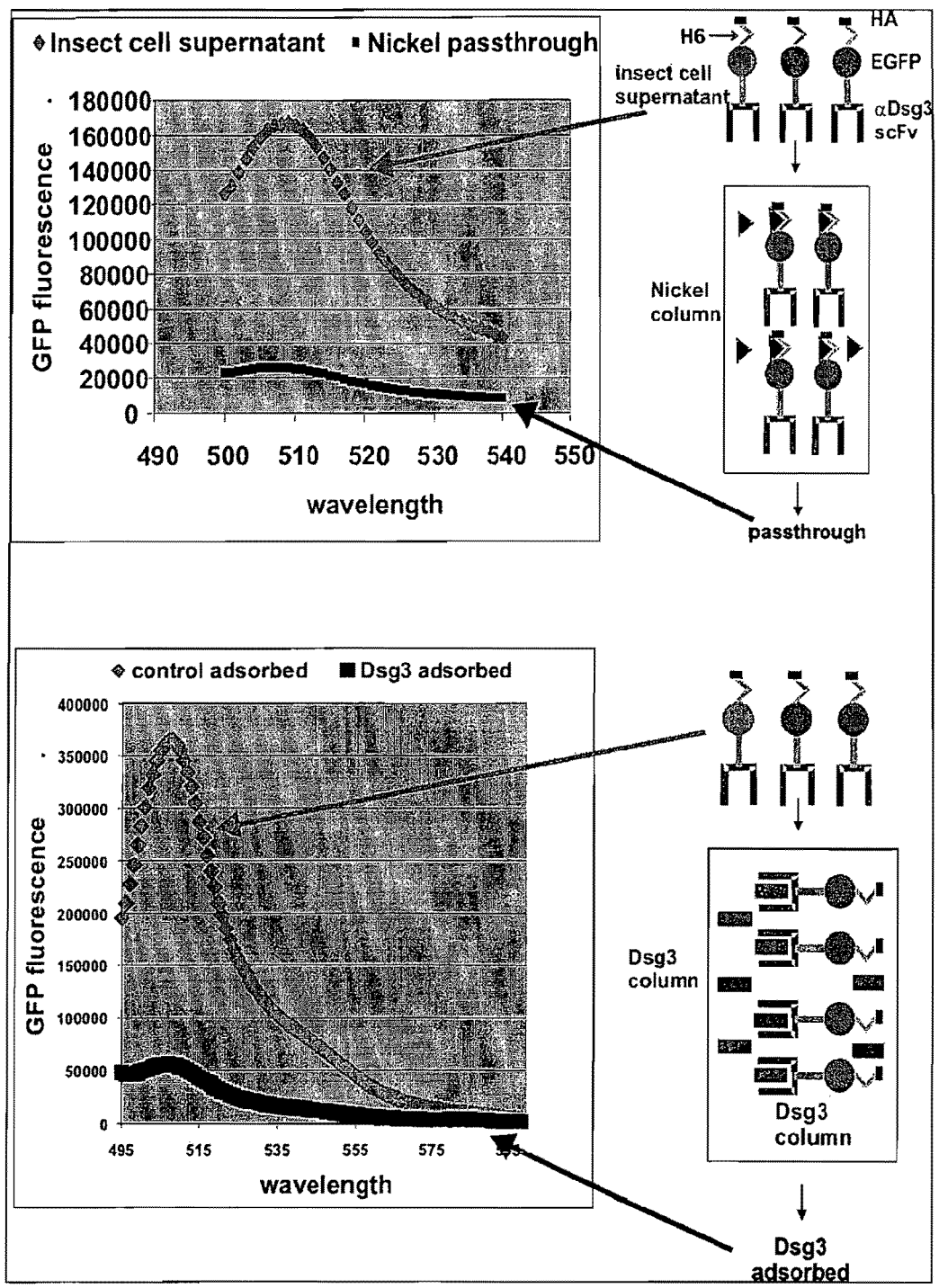

Immunofluorescence (of EGFP) on monkey esophagus showed binding of the purified chimeric protein to the cell surface of keratinocytes, which was totally adsorbed out by recombinant Dsg3 (FIG. 14D).

Figure 14E:
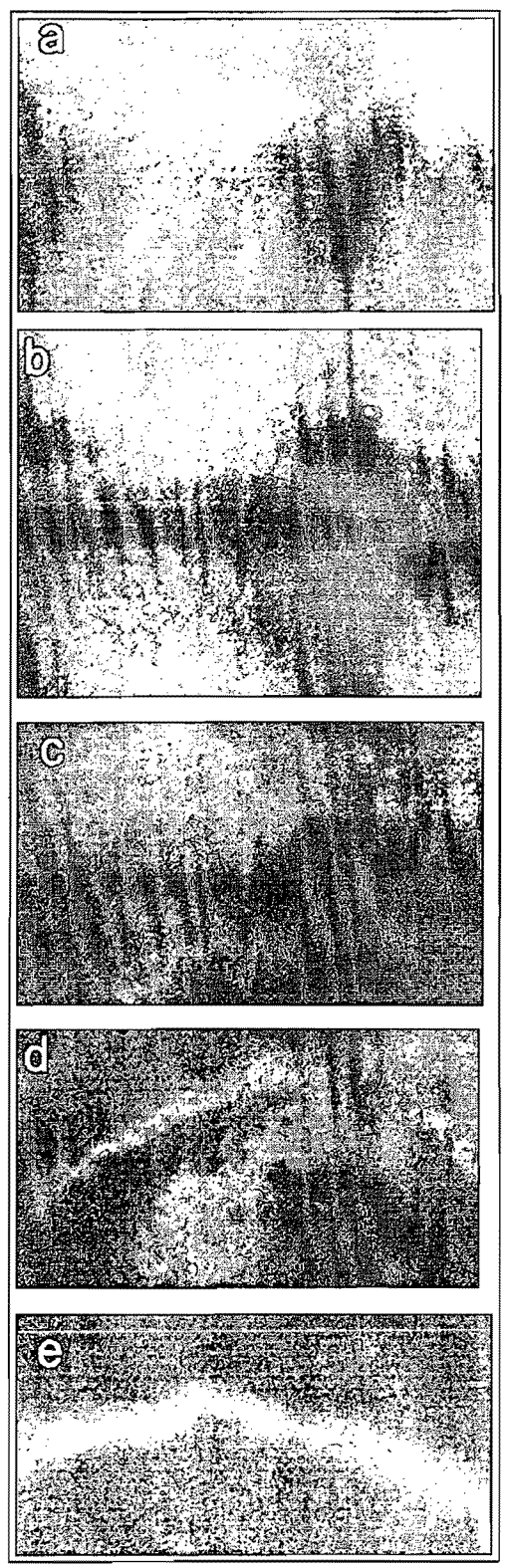

The next set of experiments were designed to show that anti-Dsg3 scFv can deliver a protein (EGFP) to epidermis in vivo. Purified anti-Dsg3 scFvEGFP was injected into neonatal and adult mice. The use of both 4B3EGFP and another anti-Dsg3 scFv, Px4-4 (non-pathogenic), that was cloned into the baculovirus transfer vector which was used to produce and purify the chimeric scFv-EGFP protein as described above, demonstrated the feasibility of substituting different scFv in this system. These anti-Dsg3-EGFP chimeric proteins bound keratinocytes when injected intradermally or intravenously, showing that a protein of about 25 kD, EGFP, could be targeted to epidermis (FIG. 14E).

Discussion of Experimental Results

Using phage display, a repertoire of human monoclonal anti-Dsg autoantibodies was cloned, both pathogenic and nonpathogenic, from a patient with active mucocutaneous PV. These mAbs bind to recombinant desmogleins by ELISA and native desmogleins in human tissue by immunofluorescence analysis. ScFv binding to desmogleins can be blocked by sera from multiple pemphigus patients. These antibodies bind to Dsg3, Dsg1 or both Dsg3 and Dsg1, and, thus, bind to normal or diseased tissue that express these molecules. The observation of non-pathogenic scFv that bind to epidermis, suggested to us that such scFv could be used to target various agents to normal and diseased tissue through binding to normal tissue antigens.

ScFvs are monovalent polypeptides comprising a single antigen binding domain, which is devoid of Fc effector function. The finding that some scFv mAbs can induce blisters in mice clinically and histologically similar to those observed in pemphigus patients and also interfere with the adhesive function of Dsg1 and Dsg3 in cultured human keratinocytes is consistent with direct disruption of desmoglein interactions by pemphigus autoantibodies, as shown in previous studies using serum-derived Fab' fragments (Rock et al., 1990, J. Clin. Invest., 85:296-299; Mascaro et al., 1997, Clin. Immunol. Immunopathol., 85:90-96). Epitope mapping data using pemphigus IgG or pathogenic mAbs isolated from an adoptive transfer mouse model of pemphigus show that almost all pathogenic autoantibodies bind conformational epitopes in the desmoglein amino-terminal extracellular domain that is predicted to form the intercellular trans-adhesive interface (Li et al., 2003, J. Exp. Med., 197:1501-1510; Tsunoda et al., 2003, J. Immunol., 170:2170-2178; Futei et al., 2000, J. Invest. Dermatol., 115:829-834).

With respect to the fine specificity and functional properties of anti-Dsg autoantibodies, the ability to isolate and characterize human mAbs has provided insight into the immunobiology of PV, which is difficult to discern with studies of polyclonal patient sera. ScFv mAbs bind to human epidermis with immunofluorescence patterns that are mostly consistent with their desmoglein-binding patterns by ELISA.

To further define the epitopes that are bound by pemphigus mAbs, inhibition ELISA assays with pemphigus patients' sera were performed. These experiments suggest that the epitopes bound by the mAbs derived from the patient are similar or identical to those recognized by other pemphigus patients' sera, for both pathogenic and nonpathogenic antibodies. Furthermore, scFv mAbs from D1 clones were inhibited by sera from patients with both mucocutaneous PV and PF, suggesting that anti-Dsg1 antibodies from PV patients recognize similar epitopes to those recognized by PF antibodies generated during a primary autoimmune response to Dsg1. These data suggest that patterns of epitope recognition may be conserved between PF and PV patients. Although these scFvs were isolated from a single patient, the ELISA inhibition data indicate that the recombinant mAbs are biochemically representative of autoantibodies from multiple pemphigus patients in regard to immunologic epitopes. Genetic analysis of pemphigus mAbs reveals both heavy and light chain gene restriction, with mAbs of different heavy and light chain families demonstrating different antigen-binding characteristics. The human Ig $V_H$ repertoire consists of approximately 50 functional gene segments, which are divided into 7 gene families (VH1-VH7) based on nucleic acid identity (Collins et al., 2003, Pharmacol. Ther. 100:157-170; Cook et al., 1995, Immunol. Today., 16:237-242). The majority of $V_H$ genes fall into the VH3 gene family (22 members, or 43%), with VH1, VH3, and VH4 gene families collectively comprising 86% of all $V_H$ gene sequences. Restricted patterns of heavy and light chain gene usage have been described for a number of autoimmune and naturally occurring immune responses, including idiopathic thrombocytopenic purpura, systemic lupus erythematosus, rheumatoid arthritis, Sjögren syndrome, and *Haemophilus influenzae* type b infection, among others (Roark et al., 2002, Blood., 100:1388-1398; Roben et al., 1996, J. Clin. Invest., 98:2827-2837; Newkirk et al., 1993, Mol. Immunol., 30:255-263; Dörner et al., 2002, Autoimmun. Rev., 1:119-124; Adderson et al., 1991, J. Immunol., 147:1667-1674). However, nonstochastic utilization of $V_H$ gene segments has been reported to occur in the normal human antibody repertoire as well, with overrepresentation of VH3-23 and VH4-34, possibly due to mechanisms of both preferential rearrangement of $V_H$ gene loci and receptor-dependent selection (Suzuki et al., 1995, J. Immunol., 154:3902-3911; Kraj et al., 1997, J. Immunol., 158:5824-5832). The data presented herein demonstrate restricted patterns of $V_H$ gene usage for pemphigus antibodies, with preferential usage of VH1 family genes (notably VH1-e) and VH3 family genes for D3 clones, and VH3 family genes for D1 clones. D31 cloned antibodies that bound both Dsg3 and Dsg1 used both VH1 and VH4 gene segments.

The populations of scFv mAbs displaying varying desmoglein binding specificities were classified into groups derived from common B cell precursors by virtue of their distinct CDR3 signatures (indicated by the VDJ rearrangement number in FIG. 9B). These findings indicate that autoantibodies that bind Dsg3, Dsg1, or both derive from different parental B cell clones. Although R/S mutational analysis demonstrated genetic evidence of antigen-driven somatic mutation in D3 clones, no examples were found in which somatic mutation of anti-Dsg mAbs changed desmoglein-binding specificity (i.e., epitope migration; Chang and Siegel, 1998 Blood 91:3066-3078). A significant implication of these data is that autoimmunity to Dsg1 likely does not derive from somatic hypermutation of antibody molecules reactive to Dsg3, and vice versa. Instead, the results presented herein shows that antibodies against Dsg3, compared with those that bind Dsg1 or both Dsg3 and Dsg1, come from genetically distinct B cell populations.

The finding of a predominant (although not exclusive) use of λ light chain sequences was unexpected, as pemphigus sera (including the one used to construct this library) contain autoantibodies comprising both λ and κ light chains (data not shown). This λ predominance may reflect an actual increase in efficiency of binding of anti-Dsg antibodies with λ chains in vivo or alternatively may reflect a selection bias during the panning of antibodies on ELISA plates. The lack of a specific light chain gene segment restriction in the D1 scFvs suggests that binding to Dsg1 is determined primarily by the heavy chain. Further studies, such as light chain shuffling experiments (Roark et al., 2002, Blood, 100:1388-1398; Roben et al., 1996, J. Clin. Invest. 98:2827-2837) and screening of separate λ and κ phage libraries, will be necessary to fully delineate the light and heavy chain contributions to binding of desmogleins.

The above observations regarding $V_H$ gene segment restriction in anti-Dsg antibodies and possible shared epitopes among patients suggest several approaches that might be taken for novel, and more targeted, therapy of pemphigus patients. For example, in mice, infusions of microgram amounts of the B cell superantigen Staphylococcal protein A have been shown to cause apoptosis of B lymphocytes expressing antibodies of clan III gene-encoded $V_H$ segments, the murine homologs for human VH3 genes (Goodyear et al., 2003, J. Exp. Med., 197:1125-1139; Silverman et al., 2005, Transfusion, 45:274-280). If certain $V_H$ gene segments predominate in pathogenic antibodies, then therapy could be directed against B cells that express those segments. Additionally, if pathogenic mAbs define shared epitopes among patients, then these antibodies could be used to screen peptide phage display libraries for molecules that structurally mimic those epitopes. Such molecules could be used to block pathogenic antibodies in disease, an approach that has previously been successful for the inhibition of factor VIII autoantibodies in hemophilia (Villard et al., 2003, Blood, 102:949-952). Furthermore, anti-idiotypic antibodies specific for autoantibodies from a pemphigus patient have shown promising results in blocking pathogenicity of autoantibodies from other patients (Alvarado-Flores et al., 2001, Scand. J. Immunol., 53:254-258). The data presented herein show that pathogenic mAbs define shared epitopes among patients are also consistent with the idea that the pathogenic antibodies share idiotypes. In this regard, scFvs could be used to raise specific anti-idiotype antibodies that in turn could be used to block pathogenic idiotypes in disease.

Finally, the phage display technique used here could also be useful for isolating antibodies against previously proposed non-desmoglein pemphigus antigens (Grando et al., 2001, J. Invest. Dermatol., 117:990-994) to evaluate whether they are significant contributors to the pathophysiology of pemphigus. Taken together, these studies describe the first successful cloning and characterization of pathogenic human monoclonal PV autoantibodies. These mAbs reproduce disease in both animal and human keratinocyte models and offer exciting opportunities for the development of novel biologic and clinical reagents to study, diagnose, and treat this potentially fatal disease.

Example 9

System to Deliver Biologically Active Proteins to Epidermis

Although an anti-Dsg3 scFv might be able to deliver a drug to the epidermis, it may be desirable to deliver biologically active agents, not within, but just outside, the epidermis at the basement membrane. Therefore, it is desirable to use scFv derived from bullous pemphigoid patients. These patients have an autoimmune blistering disease mediated by an antibody against BP180, a transmembrane protein of the basal cell, located in the basement membrane (Diaz et al., 1990 J. Clin. Invest. 86: 1088-1094; Giudice et al., 1992 J. Invest. Dermatol. 99:243-250).

Using the same phage display method as discussed elsewhere herein for cloning scFv from pemphigus vulgaris and pemphigus foliaceus patients, human antibodies from bullous pemphigoid patients can be obtained. Such human scFv would be used for drug delivery in humans. However, these antibodies would not be expected to cross react with mouse basement membrane, because the major BP180 antigen, called NC-16A, has a different amino acid sequence in mouse and human (Liu et al., 1993 J. Clin. Invest. 92: 2480-2488). Therefore, to test drug delivery by an anti-BP180 scFv in mouse models, it is desirable to use phage display to isolate anti-mouse BP180 antibodies generated by immunization of rabbits (see below).

Without wishing to be bound by any particular theory, it is believed that such anti-basement membrane scFv linked to pro-apoptotic proteins could form an "immunological gate" that could inactivate lymphocytes as they attempt to migrate into epidermis. The experiments are designed to test persistence of an anti-BP180 scFv in mouse basement membrane and determine if such an antibody can deliver biological proteins to that area. It is believed that because induction of blister formation by antibodies in bullous pemphigoid is thought to require the effector region of IgG to activate complement, scFv would not be expected to cause blistering or pathology (Gammon et al., 1982 J. Invest. Dermatol. 78: 285-290; Liu et al., 1995 J. Clin. Invest 95: 1539-1544).

Figure 15:
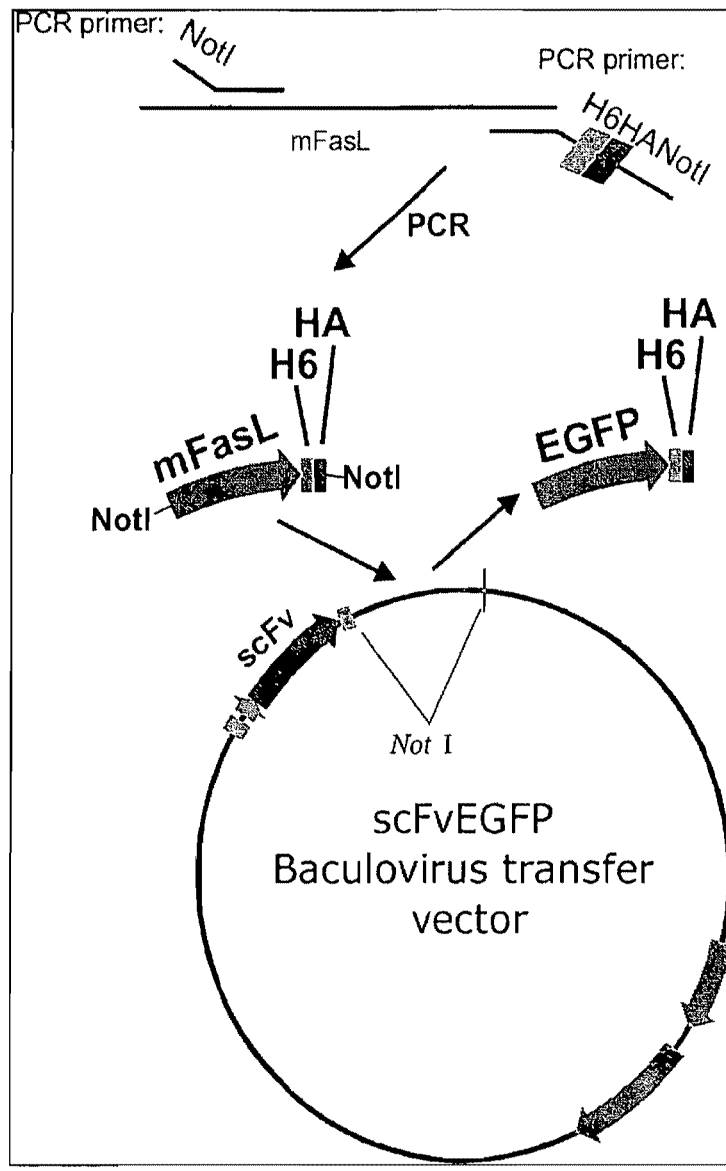
FIG. 15 is an image depicting the baculovirus transfer vector used to produce chimeric scFv-mFasL protein. The cloning strategy involves replacing EGFP with a biologically active agent, for example mFasL.

Various proteins have been described that under certain circumstances can cause apoptosis and/or inhibit proliferation of activated lymphocytes, and in some cases other leukocytes. These proteins may also induce tolerance to the activating antigen. As a non-limiting example, it is believed that pro-apoptotic proteins, such as mFasL, mPD-L1, and mTRAIL, can be beneficial to a mammal when administered to the epidermis of the mammal in need thereof in the context of a chimeric protein with anti-epidermal scFv. These chimeric molecules can be tested in mouse disease models in which activated lymphocytes or other leukocytes infiltrate epidermis. For example, chimeric scFv-mFasL protein can be produced using a baculovirus transfer vector. The cloning strategy to produce scFv-mFasL can involve replacing EGFP with mFasL (FIG. 15).

Once these anti-epidermal scFv-immunoinhibitory chimeric reagents are developed, they are tested in mouse models of human diseases that are thought to be mediated by activated T cells and leukocytes that traffic into the epidermis. Such human diseases include psoriasis, graft versus host disease, vitiligo, and the like. In addition, melanoma in situ is a disease in which melanoma cells bordering on keratinocytes may express TRAIL receptors and therefore might be a target for TRAIL delivered to the epidermis (Gardnerova et al., 2000 Curr. Drug Targets 1: 327-364). Mouse models of psoriasis (Gudjonsson et al., 2007 J. Invest Dermatol 127: 1292-1308; Nestle et al., 2006 J. Eur. Acad. Dermatol. Venerol. 20: 24-27), the epidermal component of graft versus host disease (Shibaki et al., 2004 J. Invest. Dermatol. 123: 109-115), and vitiligo (Antony et al., 2005 J. Immunol. 174: 2591-2601) are available. If successful in animal models, the reagents developed will be considered for human therapy. The advantage is that scFv derived from pemphigus or pemphigoid patients are human and would not be expected to generate an immune response.

Example 10

Cloning of Monoclonal scFv Anti-Mouse BP180 NC16A Domain Antibodies

The following experiments were designed to clone antibodies that target the basement membrane of epidermis rather than keratinocytes so that inflammatory cells could be targeted before they enter the epidermis. As an exemplary target protein, BP180 was chosen because the technique can be applied to humans by screening for scFv by phage display of antibodies cloned from bullous pemphigoid patients. However, since a mouse model of drug delivery is being used to test the feasibility of targeting the basement membrane, it is desirable to obtain scFv that bind mouse BP antigen. Because the pathogenic antibodies from human BP do not cross react well with the mouse pathogenic epitope (called NC16A), it is advantageous to clone by phage display antibodies from rabbits immunized with mouse NC16A. NC16A is the major epitope domain of bullous pemphigoid (BP) autoantibodies.

The phage display system to clone anti-desmoglein scFv from pemphigus vulgaris and pemphigus foliaceus patients discussed elsewhere herein can be adopted to bullous pemphigoid patients. The same technique can be applied to clone scFv from immunized rabbits. The only difference is that the primers for the rabbit variable heavy and light chains are different.

Rabbits were immunized with the mouse NC16A domain of BP180 cloned as a chimeric molecule with maltose binding protein (MBP). The chimeric protein was successfully cloned into the pMAL-c2x vector (FIG. 16A) and the construct was able to express the fusion protein. The fusion protein was shown to contain immunoreactive NC16A by reactivity with rabbit antisera, raised against the mouse NC 16A domain linked to glutathione S-transferase (GST) (Table 2).

TABLE 2

ELISA optical density (OD) against indicated substrate.
Rabbits were immunized against GST-mouse NC16A

|  | MBP + mNC16A | MBP (without NC16A) | GST + mNC16A |
|---|---|---|---|
| Immunized rabbit 1 | 2.058 | 0.356 | 1.45 |
| Immunized rabbit 2 | 1.844 | 0.261 | 2.496 |
| Normal rabbit | 0.212 | 0.208 | 0.373 |

Figure 16:
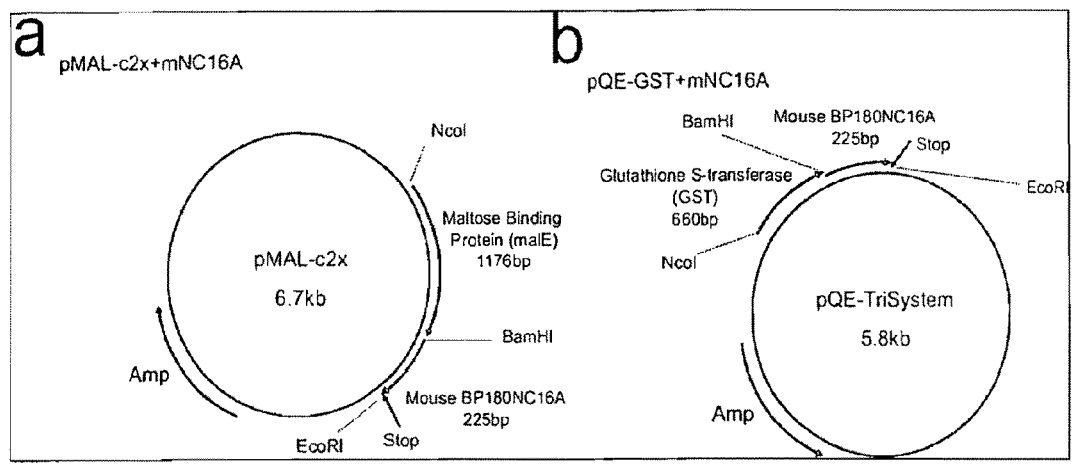
FIG. 16, comprising

To ensure that the rabbit anti-NC16A-MBP antibodies actually bound the NC16A part of the immunogen, the mouse BP180 NC16A domain linked to glutathione S-transferase (GST) was cloned (FIG. 16B). The NC16A-GST chimeric protein was used as an ELISA substrate to test the MBP-NC16A-immunized rabbit sera for reactivity against NC16A.

As discussed elsewhere herein, bone marrow, spleen and blood lymphocytes from immunized rabbits producing anti-NC 16A antibodies are extracted for mRNA which will be used for RT-PCR to clone variable heavy and light chains into the phagemid vector to produce a phage library for screening on GST-mNC16A ELISA plates. The scFv derived from this library can be tested, by anti-HA immunofluorescence, for binding to the basement membrane of epidermis after intraperitoneal injection into adult mice.

The experiments conducted using anti-Dsg3 scFv-EGFP to demonstrate localization of the scFv can be adapted to assess whether anti-BP180 molecules can deliver a protein (EGFP) to the epidermis in adult mice. Anti-BP180 scFv is cloned into the baculovirus transfer vector described elsewhere herein to produce a chimeric protein with EGFP. The chimeric molecule is injected intraperitoneally, intravenously, and intradermally into adult mice and detection of the molecule is by way of immunofluorescence of EGFP (or with anti-HA). The distribution and persistence of binding of anti-BP180 scFv and the kinetics of its disappearance from blood can be assess using the same methods used to assess anti-Dsg3 scFv localization and binding characteristics.

Without wishing to be bound by any particular theory, it is believed that anti-BP180 scFv can deliver a protein to the epidermis. Immuno-inhibitory proteins are exemplary proteins that can be delivered to the epidermis using an anti-BP180 scFv molecule. Examples of immuno-inhibitory proteins include but are not limited to Fas ligand (FasL), TRAIL, and PD-L1. The idea is that if these proteins can be delivered to epidermis they may be able to inactivate activated lymphocytes that cause epidermal disease.

The chimeric proteins can be purified on a nickel column and concentrated with Amicon filters. About 100 µl of various concentrations can be injected IV, then mice will be sacrificed at various time points for anti-HA indirect immunofluouresence of various parts of the skin, mucous membranes and internal organs to detect binding. In addition, chimeric molecules will be injected intradermally into the ear, as the ear is an important area for many immunological assays, e.g. transgenic ovalbumin model of graft vs. host disease and vitiligo. The persistence of binding over time will then be determined by anti-HA indirect immunofluorescence.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A composition comprising an antibody-protein fusion molecule, wherein said antibody is non-pathogenic to its target tissue and binds to a target molecule, wherein said target molecule is BP180, and said protein is a therapeutic protein.

2. The composition of claim 1, wherein said antibody binds to a target molecule located in the epidermis.

3. The composition of claim 1, wherein said antibody binds to a target molecule located in the basement membrane.

4. The composition of claim 1, wherein said antibody is an scFv.

5. The composition of claim 1, wherein said antibody is obtained by cloning a nucleic acid isolated from a mammal having an autoimmune disease.

6. The composition of claim 5, wherein said autoimmune disease is selected from the group consisting of pemphigus vulgaris, pemphigus foliaceus, and bullous pemphigoid.

7. The composition of claim 1, wherein said antibody is obtained by cloning a nucleic acid isolated from a mammal that is not afflicted with an autoimmune disease.

8. The composition of claim 1, wherein said therapeutic protein is an enzyme.

9. The composition of claim 1, wherein said therapeutic protein is a pro-apoptoic protein.

10. A composition comprising an antibody-protein fusion molecule, wherein said antibody is non-pathogenic to its target tissue and binds to a target molecule selected from the group consisting of desmoglein 1 (Dsg1), Dsg3, and any combination thereof, and said protein is a therapeutic protein.

11. The composition of claim 10, wherein said antibody binds to a target molecule located in the epidermis.

12. The composition of claim 10, wherein said antibody binds to a target molecule located in the basement membrane.

13. The composition of claim 10, wherein said antibody is an scFv.

14. The composition of claim 10, wherein said antibody is obtained by cloning a nucleic acid isolated from a mammal having an autoimmune disease.

15. The composition of claim 14, wherein said autoimmune disease is selected from the group consisting of pemphigus vulgaris, and pemphigus foliaceus.

16. The composition of claim 10, wherein said antibody is obtained by cloning a nucleic acid isolated from a mammal that is not afflicted with an autoimmune disease.

17. The composition of claim 10, wherein said therapeutic protein is an enzyme.

18. The composition of claim 10, wherein said therapeutic protein is a pro-apoptoic protein.

* * * * *

SEQUENCE LISTING

```
<160> NUMBER OF SEQ ID NOS: 24

<210> SEQ ID NO 1
<211> LENGTH: 413
<212> TYPE: DNA
<213> ORGANISM: Homo sapiens

<400> SEQUENCE: 1
caggtgcagc tggtgcagtc tggggctgag atgaagaagc ctgggtcctc ggtgagggtc      60
tcctgcaagg cttctggagg caccttcgac aaatatgctg tcagttgggt gcgacaggcc     120
ccaggacgag ggcttgagtg ggtgggaggg atcatcccta tgcttggtgc tccacactac     180
gcacagaagt tccagggcag agtcacgatc accgcggaca aatccacgag cacagtctac     240
atggaactga gcagcctggg atctgaggac acagccgtgt attactgtgc gagagataaa     300
gcggcttact atgaaagtgg ttattactat atcggtgact tctggggcca ggggaccctg     360
gtcaccgtct cctcagcctc caccaagggc ccatcggtca ctagtggcca ggc            413

<210> SEQ ID NO 2
<211> LENGTH: 413
<212> TYPE: DNA
<213> ORGANISM: Homo sapiens

<400> SEQUENCE: 2
caggtgcagc tggtgcagtc tggggctgag atgaagaagc ctgggtcctc ggtgagggtc      60
tcctgcaagg cttctggagg caccttcgac aaatatgctg tcagctgggt gcgacaggcc     120
```

```
ccaggacgag ggcttgagtg ggtgggaggg atcatccta tgcttggtgc tccacactac    180
gcacagaagt tccagggcag agtcacgatc accgcggaca atccacgag cacaatctac    240 atggaactga gcagcctggg atctgaggac acagccgtgt attactgtgc gagagataaa   300
gcggcttact atgaaagtgg ttattactat atcggtgact tctggggcca gggaaccctg   360
gtcaccgtct cctcagcttc caccaagggc ccatcggtca ctagtggcca ggc          413
```

<210> SEQ ID NO 3
<211> LENGTH: 413
<212> TYPE: DNA
<213> ORGANISM: Homo sapiens

<400> SEQUENCE: 3

```
gaggtgcagc tggtggagtc tggggctgag atgaagaagc ctgggtcctc ggtgagggtc    60
tcctgcaagg cttctggagg caccttcgac aaatatggtg tcagttgggt gcgacaggcc   120
ccaggacgag ggcttgagtg ggtgggaggg atcatccta tgcttggtgc tccacactac    180
gcacagaagt tccagggcag agtcacgatc accgcggaca atccacgag cacagtctat    240 atggaactga gcagcctggg atctgaggac acagccgtgt attactgcgc gagagataaa   300
gcggcttact atgaaagtgg ttattactat atcggtgact tctggggcca gggaaccctg   360
gtcaccgtct cctcagcctc caccaagggc ccatcggtca ctagtggcca ggc          413
```

<210> SEQ ID NO 4
<211> LENGTH: 413
<212> TYPE: DNA
<213> ORGANISM: Homo sapiens

<400> SEQUENCE: 4

```
caggtgcagc tggtgcagtc tggggctgag atgaagaggc ctgggtcctc ggtgagggtc    60
tcctgcaagg cttctggagg caccttcgac aaatatgctg tcagttgggt gcgacaggcc   120
ccaggacgag ggcttgagtg ggtgggggg atcatcctc tgcttggtgc tccacactac    180
gcacagaagt tccagggcag agtcacgatc accgcggaca atccacgag cacagtctac    240 atggaactga gcagcctggg atctgaggac acagccgtgt attactgcgc gagagataaa   300
gcggcttact atgaaagtgg ttattactat atcggtgact tctggggcca gggaaccctg   360
gtcaccgtct cctcagcctc caccaagggc ccatcggtca ctagtggcca ggc          413
```

<210> SEQ ID NO 5
<211> LENGTH: 419
<212> TYPE: DNA
<213> ORGANISM: Homo sapiens

<400> SEQUENCE: 5

```
gaggtgcagc tgttggagtc tggcccagga ccggtgaagc cttcggggac cctgtccctc    60
acctgtggtg tctctggtgg ctccatcagc actaatcact ggtggacttg ggtccgccag   120
cccccagggc aggggctgga gtggattggg gaaatccatc ataatgggag caccttcttc   180
aacccgtccc tcaagagtcg agtcaccatt tcagtggaca agtccaacaa ccagttctcc   240
ctgaaactga cctctctgac cgccgcggac acggccgtgt atttctgtgc gagagggtgg   300
caccggactg gatttcgtgg ctaccccttc cactggtact cgatctctg ggccgtggc    360 accctggtca ctgtctcctc agcttccacc aagggcccat cggtcactag tggccaggc   419
```

<210> SEQ ID NO 6
<211> LENGTH: 419

```
<212> TYPE: DNA
<213> ORGANISM: Homo sapiens

<400> SEQUENCE: 6
caggtgcagc tgcaggagtc gggcccagga ccggtgaagc cttcggggac cctgtccctc    60
acctgcggtg tctctggtgg ctccattagc agtaatcact ggtggacttg ggtccgccag   120
cccccaggga aggggctgga gtggattgga gaaatctatc ataatgggag caccttcctc   180
aacccgtccc tcaagagtcg agtcaccatt tcagtagaca agtccaacaa ccagttctcc   240
ctgaaactga cttctgtgac cgccgcggac acggccgtgt attactgtgc gagagggtgg   300
caccggactg gatttcgtgg ctacccttcc cactggtact tcgatctctg gggccgtggc   360
accctggtct ctgtctcctc agcctccacc aagggcccat cggtcactag tggccaggc    419

<210> SEQ ID NO 7
<211> LENGTH: 334
<212> TYPE: DNA
<213> ORGANISM: Homo sapiens

<400> SEQUENCE: 7
gccgagctcg tgctgactca gccaccttca gcgtctgaga ccccgggca gagggtcacc     60 atctcctgtt ctggaagcag ctccaacatc gcaggtaata ctgtgtactg gtaccagcag   120
ctcccaggag cggcccccaa gctcctcatc tattacaatg atcagcggcc ctcaggggtc   180
cctgaccgat tctctggctc caagtctggc acctcctcct ccttggccat cagtgggctc   240
cagtctgagg atgaggctta ttattactgt gcaacatggg atgaagatgt gaatggttgg   300
gtgttcggcg gagggaccaa gctgaccgtc ctag                               334

<210> SEQ ID NO 8
<211> LENGTH: 334
<212> TYPE: DNA
<213> ORGANISM: Homo sapiens

<400> SEQUENCE: 8
gccgagctcg agctgactca gccaccctca gtgtctggga ccccgggca gagggtcacc     60 atctcctgtt ctggaagcag ctccaacatc gcaggtaata ctgtgtactg gtaccaacag   120
ctcccaggag cggcccccaa gctcctcatc tattacaatg atcagcggcc ctcaggggtc   180
cctgaccgat tctctggctc caagtctggc acctcctcct ccttgaccat cagtgggctc   240
cagtctgagg atgaggctta ttattactgt gcaacatggg atgaagatgt gaatggttgg   300
gtgttcggcg gaggcaccaa gctgaccgtc ctag                               334

<210> SEQ ID NO 9
<211> LENGTH: 334
<212> TYPE: DNA
<213> ORGANISM: Homo sapiens

<400> SEQUENCE: 9
gccgagctca tgctgactca gccccactca gcgtctgaga ccccgggca gagggtcacc     60 atctcctgtt ctggaagcag ctccaacatc gcaggtaata ctgtgtactg gtaccagcag   120
ctcccaggag cggcccccaa gctcctcatc tattacaatg atcagcggcc ctcaggggtc   180
cctgaccgat tctctggctc caagtctggc acctcctcct ccttggccat cagtgggctc   240
cagtctgagg atgaggctta ttattactgt gcaacatggg atgaagatgt gaatggttgg   300
gtgttcggcg gagggaccga gctgaccgtc ctcg                               334
```

<210> SEQ ID NO 10
<211> LENGTH: 334
<212> TYPE: DNA
<213> ORGANISM: Homo sapiens

<400> SEQUENCE: 10

```
gccgagctcg tgctgactca atcgccctca gcgtctgaga ccccccgggca gagggtcacc      60
atctcctgtt ctggaagcag ctccaacatc gcaggtaata ctgtatactg gtaccagcag     120
ctcccaggag cggcccccaa gctcctcatc tattacaatg atcagcggcc ctcaggggtc     180
cctgaccgat tctctggctc caagtctggc acctcctcct ccttggccat cagtgggctc     240
cagtctgagg atgaggctta ttattactgt gcgacatggg atgaagatgt gaatggttgg     300
gtgttcggcg agggaccaa ggtgaccgtc ctag                                   334
```

<210> SEQ ID NO 11
<211> LENGTH: 331
<212> TYPE: DNA
<213> ORGANISM: Homo sapiens

<400> SEQUENCE: 11

```
gccgagctcg tgttgacgca gccgccctca gtgtctggga ccccccgggca gagggtcacc      60
atctcttgtt ctggaagcag ctcccacatc ggaaataatt atgtatactg gtaccagcat     120
ctcccaggaa cggcccccaa actcctcatc tacagtaatg atcagcggcc ctcaggggtc     180
cctgaccgat tctctgcctc caagtctgcc acctcagcct ccctggccat cagtgggctc     240
cggtccgagg atgaggctga ttattactgt gcagcatggg atgacagcca gggggagtg     300
ttcggcggag ggaccaaggt gaccgtccta g                                     331
```

<210> SEQ ID NO 12
<211> LENGTH: 331
<212> TYPE: DNA
<213> ORGANISM: Homo sapiens

<400> SEQUENCE: 12

```
gccgagctcg tgctgactca gccaccttca gtgtctggga ccccccgggca gagggtcacc      60
atctcttgtt ctggaagcag ctcccacatc ggaagtaatt atgtgtactg gtaccagcag     120
ctcccaggaa cggcccccaa aatcctcatc tacagtaatg atcagcggcc cgcaggggtc     180
cctgaccgat tctctgcctc caagtctggc acctcagcct ccctggccat cagtgggctc     240
cggtccgagg atgaggctga ttattactgt gcagcatggg atgacggcca ggggggggtc     300
ttcggcggag ggaccaagct gaccgtccta g                                     331
```

<210> SEQ ID NO 13
<211> LENGTH: 137
<212> TYPE: PRT
<213> ORGANISM: Homo sapiens

<400> SEQUENCE: 13

Gln Val Gln Leu Val Gln Ser Gly Ala Glu Met Lys Lys Pro Gly Ser
1               5                   10                  15

Ser Val Arg Val Ser Cys Lys Ala Ser Gly Gly Thr Phe Asp Lys Tyr
            20                  25                  30

Ala Val Ser Trp Val Arg Gln Ala Pro Gly Arg Gly Leu Glu Trp Val
        35                  40                  45

Gly Gly Ile Ile Pro Met Leu Gly Ala Pro His Tyr Ala Gln Lys Phe
    50                  55                  60

Gln Gly Arg Val Thr Ile Thr Ala Asp Lys Ser Thr Ser Thr Val Tyr

```
                65                  70                  75                  80
Met Glu Leu Ser Ser Leu Gly Ser Glu Asp Thr Ala Val Tyr Tyr Cys
                    85                  90                  95

Ala Arg Asp Lys Ala Ala Tyr Tyr Glu Ser Gly Tyr Tyr Tyr Ile Gly
                100                 105                 110

Asp Phe Trp Gly Gln Gly Thr Leu Val Thr Val Ser Ser Ala Ser Thr
                115                 120                 125

Lys Gly Pro Ser Val Thr Ser Gly Gln
            130                 135

<210> SEQ ID NO 14
<211> LENGTH: 137
<212> TYPE: PRT
<213> ORGANISM: Homo sapiens

<400> SEQUENCE: 14

Gln Val Gln Leu Val Gln Ser Gly Ala Glu Met Lys Lys Pro Gly Ser
1               5                   10                  15

Ser Val Arg Val Ser Cys Lys Ala Ser Gly Gly Thr Phe Asp Lys Tyr
                20                  25                  30

Ala Val Ser Trp Val Arg Gln Ala Pro Gly Arg Gly Leu Glu Trp Val
            35                  40                  45

Gly Gly Ile Ile Pro Met Leu Gly Ala Pro His Tyr Ala Gln Lys Phe
        50                  55                  60

Gln Gly Arg Val Thr Ile Thr Ala Asp Lys Ser Thr Ser Thr Ile Tyr
65                  70                  75                  80

Met Glu Leu Ser Ser Leu Gly Ser Glu Asp Thr Ala Val Tyr Tyr Cys
                    85                  90                  95

Ala Arg Asp Lys Ala Ala Tyr Tyr Glu Ser Gly Tyr Tyr Tyr Ile Gly
                100                 105                 110

Asp Phe Trp Gly Gln Gly Thr Leu Val Thr Val Ser Ser Ala Ser Thr
                115                 120                 125

Lys Gly Pro Ser Val Thr Ser Gly Gln
            130                 135

<210> SEQ ID NO 15
<211> LENGTH: 137
<212> TYPE: PRT
<213> ORGANISM: Homo sapiens

<400> SEQUENCE: 15

Glu Val Gln Leu Val Gln Ser Gly Ala Glu Met Lys Lys Pro Gly Ser
1               5                   10                  15

Ser Val Arg Val Ser Cys Lys Ala Ser Gly Gly Thr Phe Asp Lys Tyr
                20                  25                  30

Gly Val Ser Trp Val Arg Gln Ala Pro Gly Arg Gly Leu Glu Trp Val
            35                  40                  45

Gly Gly Ile Ile Pro Met Leu Gly Ala Pro His Tyr Ala Gln Lys Phe
        50                  55                  60

Gln Gly Arg Val Thr Ile Thr Ala Asp Lys Ser Thr Ser Thr Val Tyr
65                  70                  75                  80

Met Glu Leu Ser Ser Leu Gly Ser Glu Asp Thr Ala Val Tyr Tyr Cys
                    85                  90                  95

Ala Arg Asp Lys Ala Ala Tyr Tyr Glu Ser Gly Tyr Tyr Tyr Ile Gly
                100                 105                 110

Asp Phe Trp Gly Gln Gly Thr Leu Val Thr Val Ser Ser Ala Ser Thr
                115                 120                 125
```

```
Lys Gly Pro Ser Val Thr Ser Gly Gln
    130                 135
```

<210> SEQ ID NO 16
<211> LENGTH: 137
<212> TYPE: PRT
<213> ORGANISM: Homo sapiens

<400> SEQUENCE: 16

```
Gln Val Gln Leu Val Gln Ser Gly Ala Glu Met Lys Arg Pro Gly Ser
1               5                   10                  15

Ser Val Arg Val Ser Cys Lys Ala Ser Gly Thr Phe Asp Lys Tyr
            20                  25                  30

Ala Val Ser Trp Val Arg Gln Ala Pro Gly Arg Gly Leu Glu Trp Val
            35                  40                  45

Gly Gly Ile Ile Pro Leu Leu Gly Ala Pro His Tyr Ala Gln Lys Phe
    50                  55                  60

Gln Gly Arg Val Thr Ile Thr Ala Asp Lys Ser Thr Ser Thr Val Tyr
65                  70                  75                  80

Met Glu Leu Ser Ser Leu Gly Ser Glu Asp Thr Ala Val Tyr Tyr Cys
                85                  90                  95

Ala Arg Asp Lys Ala Ala Tyr Tyr Glu Ser Gly Tyr Tyr Tyr Ile Gly
            100                 105                 110

Asp Phe Trp Gly Gln Gly Thr Leu Val Thr Val Ser Ser Ala Ser Thr
        115                 120                 125

Lys Gly Pro Ser Val Thr Ser Gly Gln
    130                 135
```

<210> SEQ ID NO 17
<211> LENGTH: 139
<212> TYPE: PRT
<213> ORGANISM: Homo sapiens

<400> SEQUENCE: 17

```
Glu Val Gln Leu Leu Glu Ser Gly Pro Gly Pro Val Lys Pro Ser Gly
1               5                   10                  15

Thr Leu Ser Leu Thr Cys Gly Val Ser Gly Gly Ser Ile Ser Thr Asn
            20                  25                  30

His Trp Trp Thr Trp Val Arg Gln Pro Pro Gly Gln Gly Leu Glu Trp
            35                  40                  45

Ile Gly Glu Ile His His Asn Gly Ser Thr Phe Phe Asn Pro Ser Leu
    50                  55                  60

Lys Ser Arg Val Thr Ile Ser Val Asp Lys Ser Asn Asn Gln Phe Ser
65                  70                  75                  80

Leu Lys Leu Thr Ser Leu Thr Ala Ala Asp Thr Ala Val Tyr Phe Cys
                85                  90                  95

Ala Arg Gly Trp His Arg Thr Gly Phe Arg Gly Tyr Pro Ser His Trp
            100                 105                 110

Tyr Phe Asp Leu Trp Gly Arg Gly Thr Leu Val Thr Val Ser Ser Ala
        115                 120                 125

Ser Thr Lys Gly Pro Ser Val Thr Ser Gly Gln
130                 135
```

<210> SEQ ID NO 18
<211> LENGTH: 139
<212> TYPE: PRT
<213> ORGANISM: Homo sapiens -continued

```
<400> SEQUENCE: 18

Gln Val Gln Leu Gln Glu Ser Gly Pro Gly Val Lys Pro Ser Gly
1               5                   10                  15

Thr Leu Ser Leu Thr Cys Gly Val Ser Gly Gly Ser Ile Ser Ser Asn
            20                  25                  30

His Trp Trp Thr Trp Val Arg Gln Pro Pro Gly Lys Gly Leu Glu Trp
        35                  40                  45

Ile Gly Glu Ile Tyr His Asn Gly Ser Thr Phe Leu Asn Pro Ser Leu
    50                  55                  60

Lys Ser Arg Val Thr Ile Ser Val Asp Lys Ser Asn Asn Gln Phe Ser
65                  70                  75                  80

Leu Lys Leu Thr Ser Val Thr Ala Ala Asp Thr Ala Val Tyr Tyr Cys
                85                  90                  95

Ala Arg Gly Trp His Arg Thr Gly Phe Arg Gly Tyr Pro Ser His Trp
            100                 105                 110

Tyr Phe Asp Leu Trp Gly Arg Gly Thr Leu Val Ser Val Ser Ser Ala
        115                 120                 125

Ser Thr Lys Gly Pro Ser Val Thr Ser Gly Gln
    130                 135

<210> SEQ ID NO 19
<211> LENGTH: 111
<212> TYPE: PRT
<213> ORGANISM: Homo sapiens

<400> SEQUENCE: 19

Ala Glu Leu Val Leu Thr Gln Pro Pro Ser Ala Ser Glu Thr Pro Gly
1               5                   10                  15

Gln Arg Val Thr Ile Ser Cys Ser Gly Ser Ser Ser Asn Ile Ala Gly
            20                  25                  30

Asn Thr Val Tyr Trp Tyr Gln Gln Leu Pro Gly Ala Ala Pro Lys Leu
        35                  40                  45

Leu Ile Tyr Tyr Asn Asp Gln Arg Pro Ser Gly Val Pro Asp Arg Phe
    50                  55                  60

Ser Gly Ser Lys Ser Gly Thr Ser Ser Ser Leu Ala Ile Ser Gly Leu
65                  70                  75                  80

Gln Ser Glu Asp Glu Ala Tyr Tyr Tyr Cys Ala Thr Trp Asp Glu Asp
                85                  90                  95

Val Asn Gly Trp Val Phe Gly Gly Gly Thr Lys Leu Thr Val Leu
            100                 105                 110

<210> SEQ ID NO 20
<211> LENGTH: 111
<212> TYPE: PRT
<213> ORGANISM: Homo sapiens

<400> SEQUENCE: 20

Ala Glu Leu Glu Leu Thr Gln Pro Pro Ser Val Ser Gly Thr Pro Gly
1               5                   10                  15

Gln Arg Val Thr Ile Ser Cys Ser Gly Ser Ser Ser Asn Ile Ala Gly
            20                  25                  30

Asn Thr Val Tyr Trp Tyr Gln Gln Leu Pro Gly Ala Ala Pro Lys Leu
        35                  40                  45

Leu Ile Tyr Tyr Asn Asp Gln Arg Pro Ser Gly Val Pro Asp Arg Phe
    50                  55                  60

Ser Gly Ser Lys Ser Gly Thr Ser Ser Ser Leu Thr Ile Ser Gly Leu
65                  70                  75                  80
```

```
Gln Ser Glu Asp Glu Ala Tyr Tyr Cys Ala Thr Trp Asp Glu Asp
                85                  90                  95

Val Asn Gly Trp Val Phe Gly Gly Gly Thr Lys Leu Thr Val Leu
            100                 105                 110

<210> SEQ ID NO 21
<211> LENGTH: 111
<212> TYPE: PRT
<213> ORGANISM: Homo sapiens

<400> SEQUENCE: 21

Ala Glu Leu Met Leu Thr Gln Pro His Ser Ala Ser Glu Thr Pro Gly
1               5                   10                  15

Gln Arg Val Thr Ile Ser Cys Ser Gly Ser Ser Ser Asn Ile Ala Gly
            20                  25                  30

Asn Thr Val Tyr Trp Tyr Gln Gln Leu Pro Gly Ala Ala Pro Lys Leu
        35                  40                  45

Leu Ile Tyr Tyr Asn Asp Gln Arg Pro Ser Gly Val Pro Asp Arg Phe
    50                  55                  60

Ser Gly Ser Lys Ser Gly Thr Ser Ser Ser Leu Ala Ile Ser Gly Leu
65                  70                  75                  80

Gln Ser Glu Asp Glu Ala Tyr Tyr Cys Ala Thr Trp Asp Glu Asp
                85                  90                  95

Val Asn Gly Trp Val Phe Gly Gly Gly Thr Glu Leu Thr Val Leu
            100                 105                 110

<210> SEQ ID NO 22
<211> LENGTH: 111
<212> TYPE: PRT
<213> ORGANISM: Homo sapiens

<400> SEQUENCE: 22

Ala Glu Leu Val Leu Thr Gln Ser Pro Ser Ala Ser Glu Thr Pro Gly
1               5                   10                  15

Gln Arg Val Thr Ile Ser Cys Ser Gly Ser Ser Ser Asn Ile Ala Gly
            20                  25                  30

Asn Thr Val Tyr Trp Tyr Gln Gln Leu Pro Gly Ala Ala Pro Lys Leu
        35                  40                  45

Leu Ile Tyr Tyr Asn Asp Gln Arg Pro Ser Gly Val Pro Asp Arg Phe
    50                  55                  60

Ser Gly Ser Lys Ser Gly Thr Ser Ser Ser Leu Ala Ile Ser Gly Leu
65                  70                  75                  80

Gln Ser Glu Asp Glu Ala Tyr Tyr Cys Ala Thr Trp Asp Glu Asp
                85                  90                  95

Val Asn Gly Trp Val Phe Gly Gly Gly Thr Lys Val Thr Val Leu
            100                 105                 110

<210> SEQ ID NO 23
<211> LENGTH: 110
<212> TYPE: PRT
<213> ORGANISM: Homo sapiens

<400> SEQUENCE: 23

Ala Glu Leu Val Leu Thr Gln Pro Pro Ser Val Ser Gly Thr Pro Gly
1               5                   10                  15

Gln Arg Val Thr Ile Ser Cys Ser Gly Ser Ser Ser His Ile Gly Asn
            20                  25                  30

Asn Tyr Val Tyr Trp Tyr Gln His Leu Pro Gly Thr Ala Pro Lys Leu
```

```
                35                  40                  45
Leu Ile Tyr Ser Asn Asp Gln Arg Pro Ser Gly Val Pro Asp Arg Phe
    50                  55                  60

Ser Ala Ser Lys Ser Ala Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Ser
                85                  90                  95

Gln Gly Gly Val Phe Gly Gly Gly Thr Lys Val Thr Val Leu
                100                 105                 110

<210> SEQ ID NO 24
<211> LENGTH: 110
<212> TYPE: PRT
<213> ORGANISM: Homo sapiens

<400> SEQUENCE: 24

Ala Glu Leu Val Leu Thr Gln Pro Pro Ser Val Ser Gly Thr Pro Gly
1               5                   10                  15

Gln Arg Val Thr Ile Ser Cys Ser Gly Ser Ser Ser His Ile Gly Ser
                20                  25                  30

Asn Tyr Val Tyr Trp Tyr Gln Gln Leu Pro Gly Thr Ala Pro Lys Ile
            35                  40                  45

Leu Ile Tyr Ser Asn Asp Gln Arg Pro Ala Gly Val Pro Asp Arg Phe
    50                  55                  60

Ser Ala Ser Lys Ser Gly Thr Ser Ala Ser Leu Ala Ile Ser Gly Leu
65                  70                  75                  80

Arg Ser Glu Asp Glu Ala Asp Tyr Tyr Cys Ala Ala Trp Asp Asp Gly
                85                  90                  95

Gln Gly Gly Val Phe Gly Gly Gly Thr Lys Leu Thr Val Leu
                100                 105                 110
```